(12) United States Patent
Craig et al.

(10) Patent No.: US 6,800,750 B1
(45) Date of Patent: Oct. 5, 2004

(54) MC1-1 GENE REGULATORY ELEMENTS AND A PRO-APOPTOTIC MC1-1 VARIANT

(75) Inventors: Ruth W. Craig, West Lebanon, NH (US); Colin D. Bingle, Yorkshire (GB); Moira Whyte, Yorkshire (GB)

(73) Assignees: Dartmouth College, Hanover, NH (US); University of Sheffield, Sheffield (GB)

( * ) Notice: Subject to any disclaimer, the term of this patent is extended or adjusted under 35 U.S.C. 154(b) by 0 days.

(21) Appl. No.: 09/483,184

(22) Filed: Jan. 14, 2000

Related U.S. Application Data

(60) Provisional application No. 60/166,113, filed on Nov. 16, 1999.

(51) Int. Cl.$^7$ .................. C07H 21/04; C21N 15/63; C21N 1/19; C21N 1/21; C21N 5/16
(52) U.S. Cl. .................. 536/24.1; 536/23.5; 536/24.31; 435/252.3; 435/254.11; 435/320.1; 435/325
(58) Field of Search ............................... 536/24.1, 23.5, 536/24.31, 23.1, 24.33; 435/325, 252.3, 254.11, 320.1

(56) References Cited

U.S. PATENT DOCUMENTS 5,470,955 A   11/1995   Craig
5,702,897 A   12/1997   Reed et al.

FOREIGN PATENT DOCUMENTS

WO         WO 94/29330         12/1994

OTHER PUBLICATIONS

Hegemeijer, Leukemia, 1992, vol. 6, suppl. 4, pp. 16–18.*
Varmus, in: Oncogenes and the Molecular Origins of Cancer, Weinberg, Ed, 1989, p. 36.*
Raynolds et al, "Mcl–1, a member of the Bcl–2 family, delyas apoptosis induced by c–Myc overexpression in chinese hamster ovary cells", Cancer Research, 1994, vol. 54, pp. 6348–6352.*
abstract of LeCuyer et al (PNAS, 1994, vol. 91, pp. 3373–3377).*
Lopez–Nieto et al (WO 95/31574, abstract).*
abstract of Fisher et al (Nucleic acids Research, 1984, vol. 12, pp. 3295–3302).*
abstract of Saiki et al (New England Journal of Medicine, 1988, vol. 319, pp. 537–541).*
abstract of Ellar et al (US 4,918,006).*
abstract of Cech et al (Nucleosides and Nucletides, 1988, vol. 7, pp. 585–588).*
abstract of Kroeger et al (Nature, 1982, vol. 197, pp. 15–162).*
abstract of Crea et al (PNAS, 1978, vol. 75, pp. 5765–5769).*
Fu et al (CA 2,241,726, abstract).*
Nishina et al (WO 97/38004, abstract).*
Georgopoulos (WO 94/06814, abstract).*
Fioretti et al (WO 95/23237, abstract).*
Verma et al (Nature, 1997, vol. 389, pp. 239–242).*
Eck et al (Gene–Based Therapy, In: The Pharmacological Basis of Therapeutics, Goodman and Gilman, Ed.s, 1996, pp. 77–101).*
Orkin et al, ("Report and Recommendation of the Panel to Assess the NIH Investment in Research on Gene Therapy", NIH, 1995).*
Kozopas et al (PNAS, 1993, vol. 90, pp. 3516–3520).*
Accession No. LO8248, Jul. 26, 1993.*
The New England Biolabs Catalog (1993–1994, p. 91).*
Chao et al., *mcl–1 Is an Immediate–Early Gene Activated by teh Granulocyte–Macrophage Colony–Stimulating Factor (GM–CSF) Signaling Pathway an dIs One Component of teh GM–CSF Viability Response*, Molecular and Cellular Biology, Aug. 1998, pp. 4883–4898.

(List continued on next page.)

*Primary Examiner*—Karen A. Canella
(74) *Attorney, Agent, or Firm*—Gray Cary Ware & Freidenrich, LLP

(57) ABSTRACT

The present invention relates to a human Mcl-1 gene, to nucleotide sequences that act as regulatory elements for expression of an Mcl-1 gene, to polynucleotides encoding a variant Mcl-1s/ΔTM polypeptide, and to oligonucleotides, which contain at least ten nucleotides and can hybridize specifically to a splice junction of the disclosed Mcl-1 gene or to a polynucleotide encoding an Mcl-1 variant polypeptide as disclosed herein. The invention also relates to an Mcl-1s/ΔTM polypeptide, as well as to antibodies that can interact specifically with an epitope of Mcl-1s/ΔTM, but not with an epitope of the full length Mcl-1 polypeptide. In addition, the invention relates to a method of expressing a nucleic acid molecule in a cell by introducing into the cell the Mcl-1 gene regulatory element as disclosed herein, such that a nucleic acid molecule that is operatively linked to the Mcl-1 gene regulatory element is expressed in the cell. Additionally, the present invention relates to a method of identifying an agent that can modulate expression of a nucleic acid molecule from an Mcl-1 gene regulatory element. The present invention also relates to methods of modulating apoptosis of a cell, for example, by introducing an Mcl-1 gene regulatory element as disclosed herein into the cell, by introducing into the cell an Mcl-1 gene sequence as disclosed herein, or by expressing the Mcl-1s/ΔTM polypeptide in the cell. The present invention further relates to a method of identifying a cellular factor that can be involved in splicing of an Mcl-1 gene transcript. In addition, the present invention relates to a method of identifying an agent that induces expression of the Mcl-1s/ΔTM polypeptide in a cell. The present invention also relates to a method of identifying a cell that expresses an Mcl-1s/ΔTM polypeptide. The invention further relates to methods of treating a pathologic condition by inducing apoptosis in cells involved in the pathologic condition or by increasing viability of cells involved in the pathologic condition.

21 Claims, 11 Drawing Sheets

OTHER PUBLICATIONS

Craig et al., *Human and Mouse Chromosomal Mapping of the Myeloid Cell Leukemia–1 Gene: MCL1 Maps to Human Chromosome 1q21, a Region That is Frequenctly Altered in Preneoplastic and Neoplastic Disease*, Genomics 23, pp. 457–463 (1994).

Kozopas et al., *Improved Coupling Between Proliferation–Arrest and Differentiation–Induction in ML–1 Human Myeloblastic Leukemia Cells*, Journal of Cellular Physiology 145, pp. 575–586 (1990).

Kozopas et al., *MCLI, α gene expressed in programmed myeloid cell differentiation, has seqeunce similarity to BCL2*, Proc. Natl. Acad. Sci., vol. 90, pp. 3516–3520, Apr. 1993.

Taylor et al., *Induction of endogenous Bc1–xS through the control of Cbl–x pre–mRNA splicing by antisense oligonucleotides*, Nature Biotechnology, vol. 17, pp. 1097–1100, Nov. 1999.

Townsend et al., *Expression of the antiapoptotic MCL1 gene product is regulated by a mitrogen activated protein kinase–mediated pathway triggered through microtubule disruption and protein kinase C*, Oncogen (1998) 17, pp. 1223–1234.

Townsend et al., *Regulation of MCL1 through a Serum Response Factor/Elk–1–mediated Mechanism Links Expression of a Viability–promoting Member of teh BCL2 Family to teh Induction of Hematopoietic Cell Differentation*, The Journal of Biological Chemistry, vol. 274, No. 3, Issue of Jan. 15, pp. 1801–1813, 1999.

Zhou et al., *Mcl–1 in Transgenic Mice Promotes SUrvival in a Spectrum of Hemotopoietic Cell Types and Immortalization in the Myeloid Lineage*, Blood, vol. 92, No. 9 (Nov. 1), 1998, pp. 3226–3239.

Yang et al., *The Intracellular Distribution and Pattern of Expression of Mcl–1 Overlap with, but Are Not Indentical to, Those of Bcl–2*, The Journal of Cell Biology, vol. 128, No. 6, Mar. 1995, pp. 1173–1184.

Yang et al., *MCL–1, a Member of the BCL–2 Family, Is Induced Rapidly in Response to Signals for Cell Differentiation or Death, But Not to Signals for Cell Proliferation*, Journal of Cellular Physiology 166, pp. 523–536 (1996).

Zhou et al., *Mcl–1, a Bcl–2 Family Member, Delays the Death of Hematopoietic Cells Under a Variety of Apoptosis–Inducing Conditions*, Blood, vol. 89, No. 2 (Jan. 15), 1997, pp. 630–643.

* cited by examiner

FIGURE 1

```
   1 TCTAGAGTCA AATGTGCCTT ATTATCAGTA CAAAAATAAA TGGTGTCAGC
  51 TGGGTGCAGT GACTCACACC TGTAATCCCA GCACTTTAAG AGGCTGAGGC
 101 AGGTGGATCA CCTGAGGCCA GGAGTTTGAG ACCAGCCTGG CCAACATGGT
 151 GAAACCACAT TGTCAGGCCT CTGAGCCCAA GCCAAGCCAT CGCATCCCCT
 201 GTGACTTGCA CGTATACATC CAGATGGCCT GAAGTAACTG AAGATCCACA
 251 AAAGAAGTAA AAATAGCCTT AACTGATGAC ATTCCACCAT TGTGATTTGT
 301 TTCTGCCCCA CCCGAACTGA TCAATGTACT TTGTAATCTC CCCCACCCTT
 351 AAGAAGGTTC TTTGTAATTC TCCCCACCCT TGAGAATGTA CTTTGTGAGA
 401 TCCACCCCTG CCCACAAAAC ATTGCTCTCA ACTTCACCAC CTATCCCAAA
 451 ACCTGTAAGA ACTAATGATA ATCCATCACC CTTTGCTGAC TCTCTTTTCG
 501 GACTCAGCCC GCCTGCACCC AGGTGAAATA AACAGCCATG TTGCTCACAC
 551 AAAGCCTGTT TGGTGGTGTC TTCACACAGA CGCGCATGAA ACACATCTCT
 601 ACTAAAAATA CAATAATCAG CTGGGCGAGG TGGCTCACAG CTGTAATCTC
 651 AGCACTTTGG GAGGCCGAGA CAGGCAGGTC ACTTGAGGCC ATGAGTTCGA
 701 GACCAGCCTG GCCAACATCG TGAAAACCCC ATCTCTACCA AAAATACAAA
 751 AACTAGCCAG ATGTGGTGGC GCACGCCTGT AATCCCAGCT ACTCGGGAGG
 801 CTGAGGTACC GAATCGTCTG AACGTGGGAA GTGGAGCTTG TAGTGAGCCG
 851 AGATCGCCCC ACTGCACTCC AGCCTGGGCA ACAGAGCTAG ACTGTCTCAA
 901 AACAAACAAA AAATGGTGTC AAGACTCTCA GACGAGATTC TAATGGATTA
 951 AGGCCTATAT GTAAATAGCA CCAAAGACTA TGGAACAGAG ATGGGAGAAG
1001 CAAGCAGGGA GGCAGGAATA GTTTAGCTGT GGCAGTTTTA GCTTAGTCCA
1051 CTTACATAAA TGGTTCTTTA GGGTAGCACG TGGAGCATCC TCATTTCCAA
1101 ACATTGGACT GAGAGTAGAG AGCTGTGCAA AATAACCACA AGTCCCCAAC
1151 TATGCCCTCT TAATTATCCC TATCATCTAA GACTGTTGTT CCCATCCATC
1201 ACTGAACTTC CCCGTCCTCT TCCTTCAACC CCTGTGTTAG TCAATGGTTG
```

FIGURE 1 CONT'D

```
1251 AAATTTTGAT TTGGTAAAAA ACCTCTGGCG AAAACCAGCA AAAAGGGCTC
1301 ACAAATCAGG TCTCAGGGAA GCACAGAGGT AGCCACGAGA AGGCCCGAGG
1351 TGCTCATGGA AAGAGCTCGA GCCCAGGAGC TCTGGGAGGA CCCCAGGCGC
1401 TCGGAGCCGC CGTTACGTAA CCGGCACTCA GAGCCTCCGA AGACCGGAAG
1451 GCCCCGCTCA GGCCCGGCC CCGGCCCGG CCCCGCCCCG GCCCGGCCGG
1501 GCAGCTGGTA GGTGCCGTGC GCAACCCTCC GGAAGCTGCC GCCCCTTTCC
1551 CCTTTTATGG GAATACTTTT TTTAAAAAAA AAGAGTTCGC TGGCGCCACC
1601 CCGTAGGACT GGCCGCCCTA AAACCGTGAT AAAGGAGCTG CTCGCCACTT
1651 CTCACTTCCG CTTCCTTCCA GTAAGGAGTC GGGGTCTTCC CCAGTTTTCT
1701 CAGCCAGGCG GCGGCGGCGA CTGGCAatgT TTGGCCTCAA AAGAAACGCG
1751 GTAATCGGAC TCAACCTCTA CTGTGGGGGG GCCGGCTTGG GGGCCGGCAG
1801 CGGCGGCGCC ACCGCCCGG GAGGGCGACT TTTGGCTACG GAGAAGGAGG
1851 CCTCGGCCCG GCGAGAGATA GGGGGAGGGG AGGCCGGCGC GGTGATTGGC
1901 GGAAGCGCCG GCGCAAGCCC CCCGTCCACC CTCACGCCAG ACTCCCGGAG
1951 GGTCGCGCGG CCGCCGCCCA TTGGCGCCGA GGTCCCCGAC GTCACCGCGA
2001 CCCCCGCGAG GCTGCTTTTC TTCGCGCCCA CCCGCCGCGC GGCGCCGCTT
2051 GAGGAGATGG AAGCCCCGGC CGCTGACGCC ATCATGTCGC CGAAGAGGA
2101 GCTGGACGGG TACGAGCCGG AGCCTCTCGG GAAGCGGCCG GCTGTCCTGC
2151 CGCTGCTGGA GTTGGTCGGG GAATCTGGTA ATAACACCAG TACGGACGGG
2201 TCACTACCCT CGACGCCGCC GCCAGCAGAG GAGGAGGAGG ACGACTTGTA
2251 CCGGCAGTCG CTGGAGATTA TCTCTCGGTA CCTTCGGGAG CAGGCCACCG
2301 GCGCCAAGGA CACAAAGCCA ATGGGCAGGT CTGGGGCCAC CAGCAGGAAG
2351 GCGCTGGAGA CCTTACGACG GGTTGGGGAT GGCGTGCAGC GCAACCACGA
2401 GACGGCCTTC CAAGgtaagg gggttcatta atcgccaagg cctcactccc
2451 tttttccat ctctccccgg actcactcgc caagggtggg ttggaaaccg
2501 aaacgagtca gtgttgaaac gtgtctcatc ctattcctga agccagaata
2551 ttctggccat gagtcattgt ttccgcccat cttgattctt ttggaaatgg
```

FIGURE 1 CONT'D

```
2601 cagctcttgt tcaaagaccg gaaagggtgg gatgtcaatt tcaagtgggg 2651 tcaacctgag ttctgtaaat cccagtagcg attttcccgc cgcgggtggg 2701 caggcgaatc ttgcgccggt ttagacaaag gaggccgtga ggacctgcat 2751 gcttttcttt ctcagGCATG CTTCGGAAAC TGGACATCAA AAACGAAGAC

2801 GATGTGAAAT CGTTGTCTCG AGTGATGATC CATGTTTTCA GCGACGGCGT

2851 AACAAACTGG GGCAGGATTG TGACTCTCAT TTCTTTTGGT GCCTTTGTGG

2901 CTAAACACTT GAAGACCATA AACCAAGAAA GCTGCATCGA ACCATTAGCA

2951 GAAAGTATCA CAGACGTTCT CGTAAGGACA AAACGGGACT GGCTAGTTAA

3001 ACAAAGAGGC TGGgtaagtt tgccttaagg atgaaagggg ccttggagtg 3051 gagtggaagt agaatgaagg atttttttta gagaggtggg gatatctaaa 3101 ggttttatg acgcacggct gtttgcaggc tctaactaaa ggaccattgt 3151 ttatttgatt tttaagtagt ggatccttag agatagtggt atggcggtct 3201 tgaattgtat caaaaatctt ggttttctct aggcaatttt ttgttccaat 3251 tcagttgaat actcttcagt ggattcaaac catgaaaaaa taagtcacca 3301 ggggaggata gctgaaataa ttcctaaggc ggtgcctgtt ttaatggaga 3351 agatatgggg tggagcctgc gttttaaaca aacccagatc tgatgcagga 3401 tgtacttaac tacgttgaga aaaactgatc tgcgcaattg aggcgttact 3451 gaaatattag gtggtggaga tttgagaata agggttttcg tcttttacct 3501 catgggaact ctggaagtcc ttttgttagg ataaatccta ataagacctt 3551 gatagtactg taaaatgaag tttaattatc atgggtcccc gcttaagaaa 3601 ctgaagaact tattttcttt ttttgccccg gggtgaataa taattggttt 3651 actattgctt taggggggaaa ccttagatat tttaatttac cttctctctg 3701 gatagtagtg ttgttaagag agcagaaacc cattcttgaa aatgtgcttt 3751 tctttttgt tttctagGAT GGGTTTGTGG AGTTCTTCCA TGTAGAGGAC

3801 CTAGAAGGTG GCATCAGGAA TGTGCTGCTG GCTTTTGCAG GTGTTGCTGG

3851 AGTAGGAGCT GGTTTGGCAT ATCTAATAAG AtagCCTTAC TGTAAGTGCA

3901 ATAGTTGACT TTTAACCAAC CACCACCACC ACCAAAACCA GTTTATGCAG
```

FIGURE 1 CONT'D

```
3951  TTGGACTCCA AGCTGTAACT TCCTAGAGTT GCACCCTAGC AACCTAGCCA
4001  GAAAAGCAAG TGGCAAGAGG ATTATGGCTA ACAAGAATAA ATACATGGGA
4051  AGAGTGCTCC CCATTGATTG AAGAGTCACT GTCTGAAAGA AGCAAAGTTC
4101  AGTTTCAGCA ACAAACAAAC TTTGTTTGGG AAGCTATGGA GGAGGACTTT
4151  TAGATTTAGT GAAGATGGTA GGGTGGAAAG ACTTAATTTC CTTGTTGAGA
4201  ACAGGAAAGT GGCCAGTAGC CAGGCAAGTC ATAGAATTGA TTACCCGCCG
4251  AATTCATTAA TTTACTGTAG TAGTGTTAAG AGAAGCACTA AGAATGCCAG
4301  TGACCTGTGT AAAAGTTACA AGTAATAGAA CTATGACTGT AAGCCTCAGT
4351  ACTGTACAAG GGAAGCTTTT CCTCTCTCTA ATTAGCTTTC CCAGTATACT
4401  TCTTAGAAAG TCCAAGTGTT CAGGACTTTT ATACCTGTTA TACTTTGGCT
4451  TGGTTCCATG ATTCTTACTT TATTAGCCTA GTTTATCACC AATAACACTT
4501  GACGGAAGGC TCAGTAATTA GTTATGAATA TGGATATCCT CAATTCTTAA
4551  GACAGCTTGT AAATGTATTT GTAAAAATTG TATATATTTT TACAGAAAGT
4601  CTATTTCCTT GAAACGAAGG AAGTATCGAA TTTACATTAG TTTTTTTCAT
4651  ACCCTTTTGA ACTTTGCAAC TTCCGTAATT AGGAACCTGT TTCTTACAGC
4701  TTTTCTATGC TAAACTTTGT TCTGTTCAGT TCTAGAGTGT ATACAGAACG
4751  AATTGATGTG TAACTGTATG CAGACTGGTT GTAGTGGAAC AAATCTGATA
4801  ACTATGCAGG TTTAAATTTT CTTATCTGAT TTTGGTAAGT ATTCCTTAGA
4851  TAGGTTTTCT TTGAAAACCT GGGATTGAGA GGTTGATGAA TGGAAATTCT
4901  TTCACTTCAT TATATGCAAG TTTTCAATAA TTAGGTCTAA GTGGAGTTTT
4951  AAGGTTACTG ATGACTTACA AATAATGGGC TCTGATTGGG CAATACTCAT
5001  TTGAGTTCCT TCCATTTGAC CTAATTTAAC TGGTGAAATT TAAAGTGAAT
5051  TCATGGGCTC ATCTTTAAAG CTTTTACTAA AAGATTTTCA GCTGAATGGA
5101  ACTCATTAGC TGTGTGCATA TAAAAAGATC ACATCAGGTG GATGGAGAGA
5151  CATTTGATCC CTTGTTTGCT TAATAAATTA TAAAATGATG GCTTGGAAAA
5201  GCAGGCTAGT CTAACCATGG TGCTATTATT AGGCTTGCTT GTTACACACA
5251  CAGGTCTAAG CCTAGTATGT CAATAAAGCA AATACTTACT GTTTTGTTTC
```

FIGURE 1 CONT'D

```
5301  TATTAATGAT TCCCAAACCT TGTTGCAAGT TTTTGCATTG GCATCTTTGG
5351  ATTTCAGTCT TGATGTTTGT TCTATCAGAC TTAACCTTTT ATTTCCTGTC
5401  CTTCCTTGAA ATTGCTGATT GTTCTGCTCC CTCTACAGAT ATTTATATCA
5451  ATTCCTACAG CTTTCCCCTG CCATCCCTGA ACTCTTTCTA GCCCTTTTAG
5501  ATTTTGGCAC TGTGAAACCC CTGCTGGAAA CCTGAGTGAC CCTCCCTCCC
5551  CACCAAGAGT CCACAGACCT TCATCTTTC ACGAACTTGA TCCTGTTAGC
5601  AGGTGGTAAT ACCATGGGTG CTGTGACACT AACAGTCATT GAGAGGTGGG
5651  AGGAAGTCCC TTTTCCTTGG ACTGGTATCT TTTCAACTAT TGTTTTATCC
5701  TGTCTTTGGG GGCAATGTGT CAAAAGTCCC CTCAGGAATT TTCAGAGGAA
5751  AGAACATTTT ATGAGGCTTT CTCTAAAGTT TCCTTTGTAT AGGAGTATGC
5801  TCACTTAAAT TTACAGAAAG AGGTGAGCTG TGTTAAACCT CAGAGTTTAA
5851  AAGCTACTGA TAAACTGAAG AAAGTGTCTA TATTGGAACT AGGGTCATTT
5901  GAAAGCTTCA GTCTCGGAAC ATGACCTTTA GTCTGTGGAC TCCATTTAAA
5951  AATAGGTATG AATAAGATGA CTAAGAATGT AATGGGGAAG AACTGCCCTG
6001  CCTGCCCATC TCAGAGCCAT AAGGTCATCT TTGCTAGAGC TATTTTTACC
6051  TATGTATTTA TCGTTCTTGA TCATAAGCCG CTTATTTATA TCATGTATCT
6101  CTAAGGACCT AAAAGCACTT TATGTAGTTT TTAATTAATC TTAAGATCTG
6151  GTTACGGTAA CTAAAAGCCT GTCTGCCAAA TCCAGTGGAA ACAAGTGCAT
6201  AGATGTGAAT TGGTTTTTAG GGGCCCCACT TCCCAATTCA TTAGGTATGA
6251  CTGTGGAAAT ACAGACAAGG ACTTAGTTGA TATTTTGGGC TTGGGGCAGT
6301  GAGGGCTTAG GACACCCCAA GTGGTTTGGG AAAGGAGGAG GGAGTGGTGG
6351  GTTTATAGGG GAGGAGGAGG CAGGTGGTCT AAGTGCTGAC TGGCTACGTA
6401  GTTCGGGCAA ATCCTCCAAA AGGGAAAGGG AGGATTTGCT TAGAAGGATG
6451  GGGCTCCCAG TGACTACTTT TTGACTTCTG TTTGTCTTAC GCTTCTCTCA
6501  GGGAAAAACA TGCAGTCCTC TAGTGTTTCA TGTACATTCT GTGGGGGGTG
6551  AACACCTTGG TTCTGGTTAA ACAGCTGTAC TTTTGATAGC TGTGCCAGGA
6601  AGGGTTAGGA CCAACTACAA ATTAATGTTG GTTGTCAAAT GTAGTGTGTT
```

FIGURE 1 CONT'D

6651 TCCCTAACTT TCTGTTTTTC CTGAGAAAAA AAAATAAATC TTTTATTCAA

6701 ATAcagggtg tgatatgggt cttttctcat cgacgcctct ttttccttcc 6751 ctctcttagg caaaccttt agagaagtca gctgagcaaa tatgtacagg 6801 tggaattcaa agcaaaagcc tcacaaagtt gatttgcctt agagcaaagg 6851 acagttcctt cttcaattct aattagaggt gttgggtttt taattaaata 6901 tattactgct gtacttagag gagttcttaa acctccaagt aaaatcaaaa 6951 acctctttaa aatcaaaatt tctgtcttga tttatttatt tattattttt 7001 tttttgagat ggagttttgc tcttgttgtc caggctggag tgcaatggcc 7051 agatctccgc tcaccgcaac ctccgcctcc aggttcaaat gattctcctg 7101 cctcagcctc ctgagtagct gggaatacag gcatgcgcca ccacacccag 7151 ataattttgt attttggta gagatggggt ttctccgtgt tggtcaggct 7201 ggtcttgaac tcccgacctc aggtgattgc ccacctctgc ctcccagagt 7251 gccaggatac aggcgtgagc catcgcaccc agcctctgtc ttgattttt 7301 tgaatcacca ggtgttggta tgttttgttt tgttttgttt tgaggcacag 7351 tctcactctt ttgcccaggc tagagtgcag tggggcaatc tcggctcact 7401 gcaacctcag cctcccgagt agctgggatt acaggtgccc gccaccatgc 7451 ccggctaatt tttctatttt tggtagagac ggggttttgc cgtgttggtc 7501 aggctggttt gaagtcctga cctcagtgat ccactcgcct cagccgaagt 7551 gctgcgatta cagacctgag ccactgcgcc cagccttgat tttgaggtaa 7601 gagggtactt acagcagtta tctatcataa cacctaaata atacctaaag 7651 ttaaagagtt ttgatgaagt tcttggcagc agtgcttttc cccttctgct 7701 ttccaaaagg aggtaaaaag aagccagtca atttcaaaaa ccctatcctg 7751 cttttatttt cagctaccttt gaaagtgagc tgaatcacca tggaaatgtg 7801 caaatgtgag gtttgcatac ttggttttaa gccctgagca ccatatgcta 7851 atcaggcaat caggattctg tgcctccctg cagtcagttg catttctatt 7901 taaagtgca ttttggtttg gaagccccctt ttggagccta actaccaaaa 7951 ggcagcaact ttttgtatca ttacaaagaa agctgtgtaa gtgcactccc

FIGURE 1 CONT'D 8001 aagcaaaggt gtggtaggag agtagcagcc acagaggacc caagcccaag 8051 tcttggcctg agttaagtta gtgctattgc tcccattgac gtgctatgat 8101 gtgaagccgt ttctggtaca gtgttccttt gctcagcacc ttaaaagctt 8151 ggatttaata gtaactgggt aaccttaatc agtagtcaga attatcaaca 8201 ctttgcttta tttgacacaa ccagactttc tcagttcctg ttctgtatct 8251 aga

```
Mcl-1_WT      MFGLKRNAVIGLNLYCGGAGLGAGSGGATRPGGRLLATEKEASARREIGG      50
Mcl-1_s/ΔTM   MFGLKRNAVIGLNLYCGGAGLGAGSGGATRPGGRLLATEKEASARREIGG

_ _ _ _ _PEST_ _ _ _ _
Mcl-1_WT      GEAGAVIGGSAGASPPSTLTPDSRRVARPPPIGAEVPDVTATPARLLFFA      100
Mcl-1_s/ΔTM   GEAGAVIGGSAGASPPSTLTPDSRRVARPPPIGAEVPDYTATPARLLFEA

_ _ _ _ _ _ _ _ _ _PEST_ _ _ _ _ _ _ _ _ _
Mcl-1_WT      PTRRAAPLEEMEAPAADAIMSPEEEELDGYEPEPLGKRPAVLPLLELVGES      150
Mcl-1_s/ΔTM   PTRRAAPLEEMEAPAADAIMSPEEEELDGYEPEPLGKRPAVLPLLELVGES

_ _ _ _PEST_ _ _ _ _ _
Mcl-1_WT      GNNTSTDGSLPSTPPPAEEEEDELYRQSLEIISRYLREQATGAKDTKPMG      200
Mcl-1_s/ΔTM   GNNTSTDGSLPSTPPPAEEEEDELYRQSLEIISRYLREQATGAKDTKPMG

<---exon 1 | exon 2--->
                    BH3          |
Mcl-1_WT      RSGATSRKALETLRRVGDGVQRNHETVFQGMLRKLDIKNEDDVKSLSRVM      250
Mcl-1_s/ΔTM   RSGATSRKALETLRRVGDGVQRNHETVFQGHVCGVLPCRGPRRWHQECAA <---exon 1 | exon 3--->
                    BH1          |
Mcl-1_WT      IHVFSDGVTNWGRIVTLISFGAFVAKHLKTINQESCIEPLAESITDVLVR      300
Mcl-1_s/ΔTM   GFCRCCWSRSWFGISNKIALL                                 271

| exon 3--->        +      TM       +   350
                 BH2|
Mcl-1_WT      TKRDWLVKQRGWDGFVEFFHVEDLEGGIRNVLLAFAGVAGVGAGLAYLIR
```

FIG. 4A

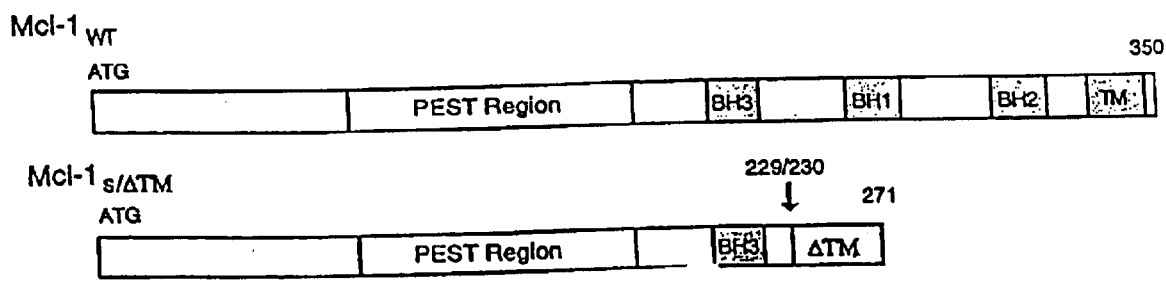

FIG. 4B

SEQUENCE LISTING

<160> NUMBER OF SEQ ID NOS: 31

<210> SEQ ID NO 1
<211> LENGTH: 8253
<212> TYPE: DNA
<213> ORGANISM: Homo sapiens

<400> SEQUENCE: 1

```
tctagagtca aatgtgcctt attatcagta caaaaataaa tggtgtcagc tgggtgcagt      60
gactcacacc tgtaatccca gcactttaag aggctgaggc aggtggatca cctgaggcca     120
ggagtttgag accagcctgg ccaacatggt gaaaccacat tgtcaggcct ctgagcccaa     180
gccaagccat cgcatcccct gtgacttgca cgtatacatc cagatggcct gaagtaactg     240
aagatccaca aaagaagtaa aaatagcctt aactgatgac attccaccat tgtgatttgt     300
ttctgcccca cccgaactga tcaatgtact ttgtaatctc ccccacccct aagaaggttc     360
tttgtaattc tccccaccct tgagaatgta ctttgtgaga tccacccctg cccacaaaac     420
attgctctca acttcaccac ctatcccaaa acctgtaaga actaatgata atccatcacc     480
cttgctgac tctcttttcg gactcagccc gcctgcaccc aggtgaaata acagccatg      540
ttgctcacac aaagcctgtt tggtggtgtc ttcacacaga cgcgcatgaa acacatctct     600
actaaaaata caataatcag ctgggcgagg tggctcacag ctgtaatctc agcactttgg     660
gaggccgaga caggcaggtc acttgaggcc atgagttcga gaccagcctg gccaacatcg     720
tgaaaacccc atctctacca aaaatacaaa aactagccag atgtggtggc gcacgcctgt     780
aatcccagct actcgggagg ctgaggtacc gaatcgtctg aacgtgggaa gtggagcttg     840
tagtgagccg agatcgcccc actgcactcc agcctgggca acagagctag actgtctcaa     900
aacaaacaaa aaatggtgtc aagactctca gacgagattc taatggatta aggcctatat     960
gtaaatagca ccaaagacta tggaacagag atgggagaag caagcaggga ggcaggaata    1020
gtttagctgt ggcagtttta gcttagtcca cttacataaa tggttcttta gggtagcacg    1080
tggagcatcc tcatttccaa acattggact gagagtagag agctgtgcaa aataaccaca    1140
agtccccaac tatgccctct taattatccc tatcatctaa gactgttgtt cccatccatc    1200
actgaacttc cccgtcctct tccttcaacc cctgtgttag tcaatggttg aaattttgat    1260
ttggtaaaaa acctctggcg aaaaccagca aaaagggctc acaaatcagg tctcagggaa    1320
gcacagaggt agccacgaga aggcccgagg tgctcatgga aagagctcga gcccaggagc    1380
tctgggagga cccaggcgc tcggagccgc cgttacgtaa ccggcactca gagcctccga    1440
agaccggaag gccccgctca ggccccggcc ccggccccgg cccgccccg gcccggccgg    1500
gcagctggta ggtgccgtgc gcaaccctcc ggaagctgcc gcccctttcc ccttttatgg    1560
gaatactttt tttaaaaaaa aagagttcgc tggcgccacc ccgtaggact ggccgcccta    1620
aaaccgtgat aaaggagctg ctcgccactt ctcacttccg cttccttcca gtaaggagtc    1680
ggggtcttcc ccagttttct cagccaggcg gcggcggcga ctggcaatgt ttggcctcaa    1740
aagaaacgcg gtaatcggac tcaacctcta ctgtgggggg gccggcttgg gggccggcag    1800
cggcggcgcc acccgcccgg gagggcgact tttggctacg gagaaggagg cctcggcccg    1860
gcgagagata gggggagggg aggccggcgc ggtgattggc ggaagcgccg gcgcaagccc    1920
cccgtccacc ctcacgccag actccgggag ggtcgcgcgg ccgccgccca ttggcgccga    1980
ggtccccgac gtcaccgcga ccccgcgag gctgcttttc ttcgcgccca cccgccgcgc    2040
```

-continued

```
ggcgccgctt gaggagatgg aagccccggc cgctgacgcc atcatgtcgc ccgaagagga    2100
gctggacggg tacgagccgg agcctctcgg gaagcggccg gctgtcctgc cgctgctgga    2160
gttggtcggg gaatctggta ataacaccag tacggacggg tcactaccct cgacgccgcc    2220
gccagcagag gaggaggagg acgagttgta ccggcagtcg ctggagatta tctctcggta    2280
ccttcgggag caggccaccg cgccaaggac acaaagccaa tgggcaggt ctggggccac     2340
cagcaggaag gcgctggaga ccttacgacg ggttggggat ggcgtgcagc gcaaccacga    2400
gacggtcttc caaggtaagg gggttcatta atcgccaagg cctcactccc tttttttccat   2460
ctctccccgg actcactcgc caagggtggg ttggaaaccg aaacgagtca gtgttgaaac    2520
gtgtctcatc ctattcctga agccagaata ttctggccat gagtcattgt ttccgcccat    2580
cttgattctt ttggaaatgg cagctcttgt tcaaagaccg gaaagggtgg gatgtcaatt    2640
tcaagtgggg tcaacctgag ttctgtaaat cccagtagcg attttcccgc cgcgggtggg    2700
caggcgaatc ttgcgccggt ttagacaaag gaggccgtga ggacctgcat gcttttcttt    2760
ctcaggcatg cttcggaaac tggacatcaa aaacgaagac gatgtgaaat cgttgtctcg    2820
agtgatgatc catgttttca gcgacggcgt aacaaactgg ggcaggattg tgactctcat    2880
ttcttttggt gcctttgtgg ctaaacactt gaagaccata aaccaagaaa gctgcatcga    2940
accattagca gaaagtatca cagacgttct cgtaaggaca aaacgggact ggctagttaa    3000
acaaagaggc tgggtaagtt tgccttaagg atgaaagggg ccttggagtg gagtggaagt    3060
agaatgaagg attttttta gagaggtggg gatatctaaa ggttttatg acgcacggct      3120
gtttgcaggc tctaactaaa ggaccattgt ttatttgatt tttaagtagt ggatccttag    3180
agatagtggt atggcggtct tgaattgtat caaaaatctt ggttttctct aggcaatttt    3240
ttgttccaat tcagttgaat actcttcagt ggattcaaac catgaaaaaa taagtcacca    3300
ggggaggata gctgaaataa ttcctaaggc ggtgcctgtt ttaatggaga agatatgggg    3360
tggagcctgc gttttaaaca aacccagatc tgatgcagga tgtacttaac tacgttgaga    3420
aaaactgatc tgcgcaattg aggcgttact gaaatattag gtggtggaga tttgagaata   3480
agggttttcg tcttttacct catgggaact ctggaagtcc ttttgttagg ataaatccta    3540
ataagacctt gatagtactg taaaatgaag tttaattatc atgggtcccc gcttaagaaa    3600
ctgaagaact tattttcttt ttttgccccg gggtgaataa taattggttt actattgctt    3660
taggggggaaa ccttagatat tttaatttac cttctctctg gatagtagtg ttgttaagag   3720
agcagaaacc cattcttgaa aatgtgcttt tcttttttgt tttctaggat gggtttgtgg    3780
agttcttcca tgtagaggac ctagaaggtg gcatcaggaa tgtgctgctg gcttttgcag    3840
gtgttgctgg agtaggagct ggtttggcat atctaataag atagccttac tgtaagtgca    3900
atagttgact tttaaccaac caccaccacc accaaaacca gtttatgcag ttggactcca    3960
agctgtaact tcctagagtt gcaccctagc aacctagcca gaaaagcaag tggcaagagg    4020
attatggcta acaagaataa atacatggga agagtgctcc ccattgattg aagagtcact    4080
gtctgaaaga agcaaagttc agtttcagca acaaacaaac tttgtttggg aagctatgga    4140
ggaggacttt tagatttagt gaagatggta gggtggaaag acttaatttc cttgttgaga    4200
acaggaaagt ggccagtagc caggcaagtc atagaattga ttacccgccg aattcattaa    4260
tttactgtag tagtgttaag agaagcacta agaatgccag tgacctgtgt aaaagttaca    4320
agtaatagaa ctatgactgt aagcctcagt actgtacaag ggaagctttt cctctctcta    4380
```

```
attagctttc ccagtatact tcttagaaag tccaagtgtt caggactttt atacctgtta    4440
tactttggct tggttccatg attcttactt tattagccta gtttatcacc aataatactt    4500
gacggaaggc tcagtaatta gttatgaata tggatatcct caattcttaa gacagcttgt    4560
aaatgtattt gtaaaaattg tatatatttt tacagaaagt ctatttcctt gaaacgaagg    4620
aagtatcgaa tttacattag ttttttttcat acccttttga actttgcaac ttccgtaatt    4680
aggaacctgt ttcttacagc ttttctatgc taaactttgt tctgttcagt tctagagtgt    4740
atacagaacg aattgatgtg taactgtatg cagactggtt gtagtggaac aaatctgata    4800
actatgcagg tttaaatttt cttatctgat tttggtaagt attccttaga taggttttct    4860
ttgaaaacct gggattgaga ggttgatgaa tggaaattct ttcacttcat tatatgcaag    4920
ttttcaataa ttaggtctaa gtggagtttt aaggttactg atgacttaca aataatgggc    4980
tctgattggg caatactcat ttgagttcct tccatttgac ctaatttaac tggtgaaatt    5040
taaagtgaat tcatgggctc atctttaaag cttttactaa aagattttca gctgaatgga    5100
actcattagc tgtgtgcata taaaaagatc acatcaggtg gatggagaga catttgatcc    5160
cttgtttgct taataaatta taaaatgatg gcttggaaaa gcaggctagt ctaaccatgg    5220
tgctattatt aggcttgctt gttacacaca caggtctaag cctagtatgt caataaagca    5280 aatactact gttttgtttc tattaatgat tcccaaacct tgttgcaagt ttttgcattg    5340
gcatctttgg atttcagtct tgatgtttgt tctatcagac ttaacctttt atttcctgtc    5400
cttccttgaa attgctgatt gttctgctcc ctctacagat atttatatca attcctacag    5460 cttttcccctg ccatccctga actctttcta gcccttttag attttggcac tgtgaaaccc    5520
ctgctggaaa cctgagtgac cctccctccc caccaagagt ccacagacct ttcatctttc    5580
acgaacttga tcctgttagc aggtggtaat accatgggtg ctgtgacact aacagtcatt    5640
gagaggtggg aggaagtccc ttttccttgg actggtatct tttcaactat tgttttatcc    5700
tgtctttggg ggcaatgtgt caaaagtccc ctcaggaatt ttcagaggaa agaacatttt    5760
atgaggcttt ctctaaagtt tcctttgtat aggagtatgc tcacttaaat ttacagaaag    5820
aggtgagctg tgttaaacct cagagtttaa aagctactga taaactgaag aaagtgtcta    5880
tattggaact agggtcattt gaaagcttca gtctcggaac atgaccttta gtctgtggac    5940
tccatttaaa aataggtatg aataagatga ctaagaatgt aatggggaag aactgccctg    6000
cctgcccatc tcagagccat aaggtcatct ttgctagagc tattttttacc tatgtattta    6060 tcgttcttga tcataagccg cttatttata tcatgtatct ctaaggacct aaaagcactt    6120
tatgtagttt ttaattaatc ttaagatctg gttacggtaa ctaaaagcct gtctgccaaa    6180
tccagtggaa acaagtgcat agatgtgaat tggttttttag gggccccact tcccaattca    6240
ttaggtatga ctgtggaaat acagacaagg acttagttga tattttgggc ttggggcagt    6300
gagggcttag gacaccccaa gtggtttggg aaggaggag ggagtggtgg gtttataggg    6360
gaggaggagg caggtggtct aagtgctgac tggctacgta gttcgggcaa atcctccaaa    6420
agggaaaggg aggatttgct tagaaggatg gggctcccag tgactacttt ttgacttctg    6480
tttgtcttac gcttctctca gggaaaaaca tgcagtcctc tagtgtttca tgtacattct    6540
gtggggggtg aacaccttgg ttctggttaa acagctgtac ttttgatagc tgtgccagga    6600
agggttagga ccaactacaa attaatgttg gttgtcaaat gtagtgtgtt tccctaactt    6660 tctgttttc ctgagaaaaa aaataaaatc ttttattcaa atacagggtg tgatatgggt    6720
cttttctcat cgacgcctct ttttccttcc ctctcttagg caaaccttt agagaagtca    6780
```

-continued

```
gctgagcaaa tatgtacagg tggaattcaa agcaaaagcc tcacaaagtt gatttgcctt      6840
agagcaaagg acagttcctt cttcaattct aattagaggt gttgggtttt taattaaata      6900
tattactgct gtacttagag gagttcttaa acctccaagt aaaatcaaaa acctctttaa      6960
aatcaaaatt tctgtcttga tttatttatt tattattttt tttttgagat ggagttttgc      7020
tcttgttgtc caggctggag tgcaatggcc agatctccgc tcaccgcaac ctccgcctcc      7080
aggttcaaat gattctcctg cctcagcctc ctgagtagct gggaatacag gcatgcgcca      7140
ccacacccag ataattttgt attttggta gagatgggg ttctccgtgt tggtcaggct       7200
ggtcttgaac tcccgacctc aggtgattgc ccacctctgc ctcccagagt gccaggatac      7260
aggcgtgagc catcgcaccc agcctctgtc ttgatttttt tgaatcacca ggtgttggta      7320
tgttttgttt tgttttgttt tgaggcacag tctcactctt tgcccaggc tagagtgcag       7380 tgggcaatc tcggctcact gcaacctcag cctcccgagt agctgggatt acaggtgccc       7440
gccaccatgc ccggctaatt tttctatttt tggtagagac ggggttttgc cgtgttggtc      7500
aggctggttt gaagtcctga cctcagtgat ccactcgcct cagccgaagt gctgcgatta      7560
cagacctgag ccactgcgcc cagccttgat tttgaggtaa gagggtactt acagcagtta      7620
tctatcataa cacctaaata atacctaaag ttaaagagtt ttgatgaagt tcttggcagc      7680
agtgcttttc cccttctgct ttccaaaagg aggtaaaaag aagccagtca atttcaaaaa      7740
ccctatcctg ctttttatttt cagctaccct gaaagtgagc tgaatcacca tggaaatgtg      7800
caaatgtgag gtttgcatac ttggttttaa gccctgagca ccatatgcta atcaggcaat      7860
caggattctg tgcctccctg cagtcagttg catttctatt taaaagtgca ttttggtttg      7920
gaagcccctt ttggagccta actaccaaaa ggcagcaact ttttgtatca ttacaaagaa      7980
agctgtgtaa gtgcactccc aagcaaaggt gtggtaggag agtagcagcc acagaggacc      8040
caagcccaag tcttggcctg agttaagtta gtgctattgc tcccattgac gtgctatgat      8100
gtgaagccgt ttctggtaca gtgttccttt gctcagcacc ttaaaagctt ggatttaata      8160
gtaactgggt aaccttaatc agtagtcaga attatcaaca ctttgctta tttgacacaa       8220 ccagactttc tcagttcctg ttctgtatct aga                                   8253
```

<210> SEQ ID NO 2
<211> LENGTH: 350
<212> TYPE: PRT
<213> ORGANISM: Homo sapiens

<400> SEQUENCE: 2

```
Met Phe Gly Leu Lys Arg Asn Ala Val Ile Gly Leu Asn Leu Tyr Cys
 1               5                  10                  15

Gly Gly Ala Gly Leu Gly Ala Gly Ser Gly Gly Ala Thr Arg Pro Gly
            20                  25                  30

Gly Arg Leu Leu Ala Thr Glu Lys Glu Ala Ser Ala Arg Arg Glu Ile
        35                  40                  45

Gly Gly Gly Glu Ala Gly Ala Val Ile Gly Gly Ser Ala Gly Ala Ser
    50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
            100                 105                 110
```

-continued

```
Ala Pro Ala Ala Asp Ala Ile Met Ser Pro Glu Glu Glu Leu Asp Gly
            115                 120                 125

Tyr Glu Pro Glu Pro Leu Gly Lys Arg Pro Ala Val Leu Pro Leu Leu
    130                 135                 140

Glu Leu Val Gly Glu Ser Gly Asn Asn Thr Ser Thr Asp Gly Ser Leu
145                 150                 155                 160

Pro Ser Thr Pro Pro Ala Glu Glu Glu Asp Glu Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
            195                 200                 205

Ala Leu Glu Thr Leu Arg Arg Val Gly Asp Gly Val Gln Arg Asn His
            210                 215                 220

Glu Thr Val Phe Gln Gly Met Leu Arg Lys Leu Asp Ile Lys Asn Glu
225                 230                 235                 240

Asp Asp Val Lys Ser Leu Ser Arg Val Met Ile His Val Phe Ser Asp
                245                 250                 255

Gly Val Thr Asn Trp Gly Arg Ile Val Thr Leu Ile Ser Phe Gly Ala
            260                 265                 270

Phe Val Ala Lys His Leu Lys Thr Ile Asn Gln Glu Ser Cys Ile Glu
            275                 280                 285

Pro Leu Ala Glu Ser Ile Thr Asp Val Leu Val Arg Thr Lys Arg Asp
            290                 295                 300

Trp Leu Val Lys Gln Arg Gly Trp Asp Gly Phe Val Glu Phe Phe His
305                 310                 315                 320

Val Glu Asp Leu Glu Gly Gly Ile Arg Asn Val Leu Leu Ala Phe Ala
                325                 330                 335

Gly Val Ala Gly Val Gly Ala Gly Leu Ala Tyr Leu Ile Arg
            340                 345                 350

<210> SEQ ID NO 3
<211> LENGTH: 271
<212> TYPE: PRT
<213> ORGANISM: Homo sapiens

<400> SEQUENCE: 3

Met Phe Gly Leu Lys Arg Asn Ala Val Ile Gly Leu Asn Leu Tyr Cys
1               5                   10                  15

Gly Gly Ala Gly Leu Gly Ala Gly Ser Gly Gly Ala Thr Arg Pro Gly
            20                  25                  30

Gly Arg Leu Leu Ala Thr Glu Lys Glu Ala Ser Ala Arg Arg Glu Ile
            35                  40                  45

Gly Gly Gly Glu Ala Gly Ala Val Ile Gly Gly Ser Ala Gly Ala Ser
        50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
            100                 105                 110

Ala Pro Ala Ala Asp Ala Ile Met Ser Pro Glu Glu Glu Leu Asp Gly
            115                 120                 125

Tyr Glu Pro Glu Pro Leu Gly Lys Arg Pro Ala Val Leu Pro Leu Leu
```

```
              130                 135                 140
Glu Leu Val Gly Glu Ser Gly Asn Asn Thr Ser Thr Asp Gly Ser Leu
145                 150                 155                 160

Pro Ser Thr Pro Pro Ala Glu Glu Glu Asp Glu Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
            195                 200                 205

Ala Leu Glu Thr Leu Arg Arg Val Gly Asp Gly Val Gln Arg Asn His
210                 215                 220

Glu Thr Val Phe Gln Gly Trp Val Cys Gly Val Leu Pro Cys Arg Gly
225                 230                 235                 240

Pro Arg Arg Trp His Gln Glu Cys Ala Ala Gly Phe Cys Arg Cys Cys
                245                 250                 255

Trp Ser Arg Ser Trp Phe Gly Ile Ser Asn Lys Ile Ala Leu Leu
            260                 265                 270

<210> SEQ ID NO 4
<211> LENGTH: 8
<212> TYPE: DNA
<213> ORGANISM: Artificial sequence
<220> FEATURE:
<223> OTHER INFORMATION: oligonucleotide for PCR

<400> SEQUENCE: 4 ccggaagc                                                                  8

<210> SEQ ID NO 5
<211> LENGTH: 8
<212> TYPE: DNA
<213> ORGANISM: Artificial sequence
<220> FEATURE:
<223> OTHER INFORMATION: oligonucleotide for PCR

<400> SEQUENCE: 5 ccttaagc                                                                  8

<210> SEQ ID NO 6
<211> LENGTH: 6
<212> TYPE: DNA
<213> ORGANISM: Artificial sequence
<220> FEATURE:
<223> OTHER INFORMATION: oligonucleotide for PCR

<400> SEQUENCE: 6 ccgccc                                                                    6

<210> SEQ ID NO 7
<211> LENGTH: 6
<212> TYPE: DNA
<213> ORGANISM: Artificial sequence
<220> FEATURE:
<223> OTHER INFORMATION: oligonucleotide for PCR

<400> SEQUENCE: 7 ctgacc                                                                    6

<210> SEQ ID NO 8
<211> LENGTH: 10
<212> TYPE: DNA
<213> ORGANISM: Artificial sequence
```

```
<220> FEATURE:
<223> OTHER INFORMATION: oligonucleotide for PCR

<400> SEQUENCE: 8
ccttttatgg                                                                    10

<210> SEQ ID NO 9
<211> LENGTH: 10
<212> TYPE: DNA
<213> ORGANISM: Artificial sequence
<220> FEATURE:
<223> OTHER INFORMATION: oligonucleotide for PCR

<400> SEQUENCE: 9
ccttcggctg                                                                    10

<210> SEQ ID NO 10
<211> LENGTH: 44
<212> TYPE: DNA
<213> ORGANISM: Artificial sequence
<220> FEATURE:
<223> OTHER INFORMATION: oligonucleotide for PCR

<400> SEQUENCE: 10
caaccctccg gaagctgccg cccctttccc cttttatggg aata                              44

<210> SEQ ID NO 11
<211> LENGTH: 44
<212> TYPE: DNA
<213> ORGANISM: Artificial sequence
<220> FEATURE:
<223> OTHER INFORMATION: oligonucleotide for PCR

<400> SEQUENCE: 11
caaccctcct taagctgctg accctttccc cttcggctgg aata                              44

<210> SEQ ID NO 12
<211> LENGTH: 22
<212> TYPE: DNA
<213> ORGANISM: Artificial sequence
<220> FEATURE:
<223> OTHER INFORMATION: oligonucleotide for PCR

<400> SEQUENCE: 12
attcgatcgg ggcggggcga gc                                                      22

<210> SEQ ID NO 13
<211> LENGTH: 30
<212> TYPE: DNA
<213> ORGANISM: Artificial sequence
<220> FEATURE:
<223> OTHER INFORMATION: oligonucleotide for PCR

<400> SEQUENCE: 13
cttacacagg atgtccatat taggacatct                                              30

<210> SEQ ID NO 14
<211> LENGTH: 20
<212> TYPE: DNA
<213> ORGANISM: Artificial sequence
<220> FEATURE:
<223> OTHER INFORMATION: oligonucleotide for PCR

<400> SEQUENCE: 14
gttggtcggg gaatctggta                                                         20
```

-continued

<210> SEQ ID NO 15
<211> LENGTH: 20
<212> TYPE: DNA
<213> ORGANISM: Artificial sequence
<220> FEATURE:
<223> OTHER INFORMATION: oligonucleotide for PCR

<400> SEQUENCE: 15
atctctcggt accttcggga                                            20

<210> SEQ ID NO 16
<211> LENGTH: 21
<212> TYPE: DNA
<213> ORGANISM: Artificial sequence
<220> FEATURE:
<223> OTHER INFORMATION: oligonucleotide for PCR

<400> SEQUENCE: 16
gtaaggagtc ggggtcttcc c                                          21

<210> SEQ ID NO 17
<211> LENGTH: 20
<212> TYPE: DNA
<213> ORGANISM: Artificial sequence
<220> FEATURE:
<223> OTHER INFORMATION: oligonucleotide for PCR

<400> SEQUENCE: 17
aaattaatga attcggcggg                                            20

<210> SEQ ID NO 18
<211> LENGTH: 21
<212> TYPE: DNA
<213> ORGANISM: Artificial sequence
<220> FEATURE:
<223> OTHER INFORMATION: oligonucleotide for PCR

<400> SEQUENCE: 18
tcctcttgcc acttgctttt c                                          21

<210> SEQ ID NO 19
<211> LENGTH: 30
<212> TYPE: DNA
<213> ORGANISM: Artificial sequence
<220> FEATURE:
<223> OTHER INFORMATION: oligonucleotide for PCR

<400> SEQUENCE: 19
ccccacagta gaggttgagt ccgattaccg                                 30

<210> SEQ ID NO 20
<211> LENGTH: 26
<212> TYPE: DNA
<213> ORGANISM: Artificial sequence
<220> FEATURE:
<223> OTHER INFORMATION: Consensus sequence
<220> FEATURE:
<221> NAME/KEY: misc_feature
<222> LOCATION: (22)..(22)
<223> OTHER INFORMATION: n is any nucleotide

<400> SEQUENCE: 20
caggtagagt tttttttttt tncagg                                     26

<210> SEQ ID NO 21
<211> LENGTH: 26

```
<212> TYPE: DNA
<213> ORGANISM: Artificial sequence
<220> FEATURE:
<223> OTHER INFORMATION: Consensus sequence
<220> FEATURE:
<221> NAME/KEY: misc_feature
<222> LOCATION: (22)..(22)
<223> OTHER INFORMATION: n is any nucleotide

<400> SEQUENCE: 21
aaggtggagt ttttttttt tntaga                                          26

<210> SEQ ID NO 22
<211> LENGTH: 414
<212> TYPE: DNA
<213> ORGANISM: Homo sapiens
<220> FEATURE:
<221> NAME/KEY: misc_feature
<222> LOCATION: (29)..(379)
<223> OTHER INFORMATION: n is specifically defied nucleotide

<400> SEQUENCE: 22
accacgagac ggccttccaa ggtaagggnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnng cttttctttc tcaggcatgc ttcttcggaa actg           414

<210> SEQ ID NO 23
<211> LENGTH: 14
<212> TYPE: PRT
<213> ORGANISM: Homo sapiens

<400> SEQUENCE: 23

Asn His Glu Thr Val Phe Gln Gly Met Leu Arg Lys Leu Asp
 1               5                  10

<210> SEQ ID NO 24
<211> LENGTH: 815
<212> TYPE: DNA
<213> ORGANISM: Homo sapiens
<220> FEATURE:
<221> NAME/KEY: misc_feature
<222> LOCATION: (29)..(782)
<223> OTHER INFORMATION: n is specifically defined nucleotide

<400> SEQUENCE: 24
ctagttaaac aaagaggctg ggtaagttnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
```

```
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnttttttgt tttctaggat gggtttgtgg agttc                                815

<210> SEQ ID NO 25
<211> LENGTH: 13
<212> TYPE: PRT
<213> ORGANISM: Homo sapiens

<400> SEQUENCE: 25

Leu Val Lys Gln Arg Gly Trp Asp Gly Phe Val Glu Phe
1               5                   10

<210> SEQ ID NO 26
<211> LENGTH: 57
<212> TYPE: DNA
<213> ORGANISM: Homo sapiens

<400> SEQUENCE: 26
acatggagct gcagaggtgt gggtcctctc tcctgcagga tgattgccgc cgtggac        57

<210> SEQ ID NO 27
<211> LENGTH: 12
<212> TYPE: PRT
<213> ORGANISM: Homo sapiens

<400> SEQUENCE: 27

Asn Met Glu Leu Gln Arg Met Ile Ala Ala Val Asp
1               5                   10

<210> SEQ ID NO 28
<211> LENGTH: 61
<212> TYPE: DNA
<213> ORGANISM: Homo sapiens

<400> SEQUENCE: 28
gatcaagacc aggtggttg ggtgagaccc ctgtctctcc agggacggcc tcctctccta     60
c                                                                     61

<210> SEQ ID NO 29
<211> LENGTH: 13
<212> TYPE: PRT
<213> ORGANISM: Homo sapiens

<400> SEQUENCE: 29

Ile Gln Asp Gln Gly Gly Trp Asp Gly Leu Leu Ser Tyr
1               5                   10

<210> SEQ ID NO 30
<211> LENGTH: 51
<212> TYPE: DNA
<213> ORGANISM: Homo sapiens

<400> SEQUENCE: 30
atccaggata acggaggctg ggtaggtgtg caggatgcct ttgtggaact g              51

<210> SEQ ID NO 31
<211> LENGTH: 13
```

```
-continued

<212> TYPE: PRT
<213> ORGANISM: Homo sapiens

<400> SEQUENCE: 31

Ile Gln Asp Asn Gly Gly Trp Asp Ala Phe Val Glu Leu
1               5                   10
```

MC1-1 GENE REGULATORY ELEMENTS AND A PRO-APOPTOTIC MC1-1 VARIANT

This application claims the benefit of priority of U.S. Provisional Patent Application No. 60/166,113, filed Nov. 16, 1999, the entire contents of which is incorporated herein by reference.

This invention was made in part with government support under Grant No. CA57359 awarded by the National Institutes of Health. The government has certain rights in this invention.

BACKGROUND OF THE INVENTION

1. Field of the Invention

The present invention relates generally to molecular biology and medicine and more specifically to Mcl-1 gene regulatory elements, to a variant Mcl-1 polypeptide, the expression of which induces apoptosis of a cell, and to methods of modulating apoptosis of a cell by modulating expression of the variant Mcl-1 polypeptide.

2. Background Information

Growth and development of an organism requires that cell proliferation and cell death be tightly regulated such that the organism develops into a normal, healthy individual. Such regulation ensures that cells are present in the position and at the time they are required, and are removed when their function has been performed or they are no longer necessary or are detrimental to the organism. A mechanism of programmed cell death, also referred to a apoptosis, has evolved and contributes, in part, to the regulation of development by inducing cells to die at the appropriate time. Similarly, various self-renewing tissues in an organism, for example, skin and intestinal epithelium in a mammalian organism, are subject to continual replacement. In order to maintain homeostasis in an organism, programmed cell death acts as a balance to cell proliferation such that the renewing tissue is maintained in a functional form.

It has become clear that dysregulation of apoptosis is involved in various pathological conditions. For example, many cancers are characterized by a defect in the apoptotic process, such that the number of dying cells in a tissue is decreased below its normal level, resulting in an imbalance of cell death and cell proliferation and consequent growth of a tumor. In addition, neurodegenerative diseases are believed to be caused, at least in part, due to the induction of apoptosis, resulting in death of neuronal cells.

In view of the importance of apoptosis to the health and well being of most organisms, including humans, a great deal of effort has been directed to identifying the cellular molecules and pathways involved in the apoptotic process. As a result, several gene products that modulate the apoptotic process have been identified, and can be separated generally into two categories, each of which contains members that can function to either inhibit or induce programmed cell death. One category of gene products that modulate apoptosis includes the members of the Bcl-2 family of proteins. Bcl-2, is the best characterized member of this family and inhibits apoptosis when overexpressed in cells. Other members of this gene family include, for example, Bax, Bak, Mcl-1, Bcl-$x_L$, Bcl-$x_S$, and Bad. Some of these proteins, including Bcl-2, acts to prevent apoptosis, whereas others such as Bax, Bcl-$x_S$ and Bak augment apoptosis.

The second category of gene products that modulate the apoptotic process includes the family of aspartate-specific cysteine proteases (ASCPs; caspases). These proteases are related genetically to the Ced-3 gene product that was initially shown to be required for programmed cell death in the roundworm, *C. elegans*. The ASCPs family of proteases includes, for example, human interleukin-1-β converting enzyme (ICE), ICH-$1_L$, ICH-$1_S$, CPP32, Mch2, Mch3, ICH-2 and ICE$_{rel}$sup-III. One common feature of these gene products is that they are cysteine proteases with specificity for substrate cleavage at Asp-X bonds. Although these proteases generally induce cell death when expressed in cells, several alternative structural forms such as ICEδ, ICEε, ICH-$1_S$ and Mch2β can function to inhibit apoptosis.

In addition to the Bcl-2 and ASCP gene family members that have been identified, it is likely that other as yet unidentified gene products exist that are important in mammalian cell death. For example, in addition to Ced-3, another *C. elegans* gene, Ced-4, exists and also is required for programmed cell death in *C. elegans*. However, a mammalian homolog of this protein has not yet been identified. The physiological control mechanisms that regulate programmed cell death and the mechanisms by which the cell death pathways interact with other physiological processes within the organism also have not yet been fully defined. The identification of genes and gene products involved in the regulation of apoptosis can provide a means to modulate the apoptotic process in cells, thus allowing the development, for example, of methods for intervening in pathological conditions associated with abnormally increased or decreased levels of apoptosis, including during the growth, development and differentiation of cells in an organism. Thus, a need exists to identify genes and gene products involved in the apoptotic process in an organism. The present invention satisfies this need and provides additional advantages.

SUMMARY OF THE INVENTION

The present invention relates to substantially pure nucleotide sequences that act as regulatory elements for expression of an Mcl-1 gene. An Mcl-1 gene regulatory element includes at least about twenty contiguous nucleotides of the nucleotide sequence set forth as nucleotides 1495 to 1657 of SEQ ID NO: 1 (positions −162 to +1 of the Mcl-1 gene 5'-flanking sequence as shown in FIG. 3B). Mcl-1 gene regulatory elements are exemplified herein by a nucleotide sequence that includes nucleotides 1513 to 1564 of SEQ ID NO: 1 (positions −135 to −92 of 3B), as well as by a nucleotide sequence that includes nucleotides 1495 to 1550 of SEQ ID NO: 1 (positions −162 to −107 of FIG. 3B); nucleotides 1495 to 1564 of SEQ ID NO: 1 (positions −162 to −92); nucleotides 1495 to 1606 of SEQ ID NO: 1 (positions −62 to −51); nucleotides 1513 to 1550 of SEQ ID NO: 1 (positions −135 to −107); nucleotides 1513 to 1606 of SEQ ID NO: 1 (positions −135 to −51); nucleotides 1550 to 1657 of SEQ ID NO: 1 (positions −107 to +1); and nucleotides 1606 to 1657 of SEQ ID NO: 1 (positions −51 to +1). A particularly useful Mcl-1 gene regulatory element is exemplified by the sequence shown as nucleotides 1495 to 1657 in SEQ ID NO: 1, which correspond to position −162 to +1 in FIG. 3B. The present invention also relates to a vector that contains an Mcl-1 gene regulatory element as exemplified above. The vector can be an expression vector, and can contain a heterologous nucleic acid molecule operatively linked to the Mcl-1 gene regulatory element. A host cell containing such a vector also is contemplated.

The present invention also relates to a substantially pure Mcl-1 gene, which is a nucleic acid molecule that encodes an Mcl-1 polypeptide, and includes nucleotides 1727 to 3884 of SEQ ID NO: 1 (see, also, FIG. 1). Additional nucleic acid molecules of the invention are exemplified by a nucleic acid molecule containing nucleotides 1657 to 3884 of SEQ ID NO: 1; or containing nucleotides 1495 to 3884 of SEQ ID NO: 1; or containing 1 to 8253 of SEQ ID NO: 1 (see, also, FIG. 1). Nucleotide sequences complementary to the disclosed nucleic acid molecules also are contemplated.

The present invention further provides a substantially pure polynucleotide encoding the Mcl-1s/ΔTM amino acid sequence, which is set forth in SEQ ID NO: 3 (see, also, FIG. 4A, lower sequence); as well as a nucleotide sequence complementary to such an encoding polynucleotide. A polynucleotide of the invention is exemplified by a polynucleotide containing nucleotides 1727 to 2414 of SEQ ID NO: 1 operatively linked to nucleotides 3768 to 3884 of SEQ ID NO: 1, wherein the linked sequence encodes the polypeptide of SEQ ID NO: 3. A vector, which can be an expression vector, containing such a polynucleotide, which can be a polydeoxyribonucleotide or a polyribonucleotide, also is contemplated, as are host cells that contain such a vector.

In addition, the present invention relates to oligonucleotides, which contain at least ten contiguous nucleotides of SEQ ID NO: 1 and can hybridize specifically either to a splice junction of the disclosed Mcl-1 gene or to a polynucleotide encoding an Mcl-1 variant polypeptide as disclosed herein. Nucleotide sequences complementary to such oligonucleotides also are contemplated. An oligonucleotide that can hybridize specifically to a splice junction of the Mcl-1 gene is exemplified by an oligonucleotide that hybridizes to a portion of SEQ ID NO: 1 that includes nucleotide position 2414, or nucleotide position 2766, or nucleotide position 3013, or nucleotide position 3786 of SEQ ID NO: 1. In particular, an oligonucleotide of the invention hybridizes specifically to a nucleotide sequence of SEQ ID NO: 1 that includes at least three nucleotides 5' and contiguous to a specified nucleotide position, and at least three nucleotides 3' and contiguous to a specified nucleotide position. As such, the oligonucleotide spans an exon-intron junction of the Mcl-1 gene.

An oligonucleotide that hybridizes specifically to a polynucleotide encoding an Mcl-1 variant polypeptide as disclosed herein is exemplified by an oligonucleotide that hybridizes specifically to a nucleotide sequence of SEQ ID NO: 1 that includes nucleotides 2412 to 2414 of SEQ ID NO: 1 linked to nucleotides 3768 to 3770 of SEQ ID NO: 1. Such an oligonucleotide is characterized in that it hybridizes to a nucleic acid molecule containing the splice junction of exon 1 and exon 3 of the Mcl-1 gene. The oligonucleotides of the invention are useful, for example, as hybridization probes, as primers for a polymerase chain reaction, or as antisense molecules.

The present invention also relates to a substantially pure Mcl-1s/ΔTM polypeptide, which has an amino acid sequence as set forth in SEQ ID NO: 3, as well as to peptide portions of Mcl-1s/ΔTM that contain at least three contiguous amino acids of the sequence set forth as amino acids 228 to 271 of SEQ ID NO: 3. As disclosed herein, the sequence set forth as amino acids 228 to 271 of SEQ ID NO: 3 are unique to Mcl-1/ΔTM, and are not found in the full length Mcl-1 polypeptide, or in other proteins as determined by a database search. As such, the invention also relates to antibodies that can interact specifically with an epitope of Mcl-1s/ΔTM (SEQ ID NO: 3), but not with an epitope of the full length Mcl-1 polypeptide (SEQ ID NO: 2).

The present invention further relates to a method of expressing a nucleic acid molecule in a cell by introducing into the cell the Mcl-1 gene regulatory element as disclosed herein, such that a nucleic acid molecule that is operatively linked to the Mcl-1 gene regulatory element is expressed in the cell. In one embodiment, the Mcl-1 gene regulatory element integrates into a region of genomic DNA in the cell, such that an endogenous nucleic acid sequence to which the Mcl-1 gene regulatory element is operatively linked is expressed. Such a method allows the identification of nucleic acid molecules that can be expressed in a cell from the Mcl-1 gene regulatory element, and further allows the identification of a function of the expressed nucleic acid molecules in a cell in which they otherwise might not be expressed.

In another embodiment, the Mcl-1 gene regulatory element is operatively linked to a heterologous nucleic acid molecule prior to its introduction into the cell, then, following introduction into the cell, the heterologous nucleic acid molecule is expressed from the Mcl-1 gene regulatory in the cell. Such a method provides a means for the selective expression of the heterologous nucleic acid molecule in a cell, which can be, for example, a hematopoeitic cell or a cell is involved in a pathologic condition. In particular, the heterologous nucleic acid molecule can be expressed in a cell that also expresses an endogenous Mcl-1 gene product.

Additionally, the present invention relates to a method of identifying an agent that can modulate expression of a nucleic acid molecule operatively linked to an Mcl-1 gene regulatory element. Such a method can be performed, for example, by contacting under suitable conditions an Mcl-1 gene regulatory element, at least a first protein that can interact specifically with the regulatory element, and an agent to be tested; and detecting a change in the ability to form a complex between the Mcl-1 gene regulatory element and the first protein. The agent can be, for example, a nucleotide sequence, a peptide, a peptidomimetic, or a small organic molecule such as a pharmaceutical agent. Suitable conditions for performing such a method can be provided by performing the method in a reaction mixture in vitro or in a cell. A change in complex formation, which can be manifest, for example, by the formation of a complex, by the disruption of a complex, or by altered stability of a complex, can be detected directly by detecting, for example, a change in the electrophoretic mobility of the complex (or of components of the complex), or indirectly by detecting, for example, a change in the expression of a reporter nucleotide sequence expressed from the regulatory element.

In one embodiment, at least the first protein and the regulatory element interact specifically to form a complex in the absence of the agent. The agent can alter a specific interaction of the protein with the regulatory element, for example, by disrupting a complex of the first protein and the regulatory element, or by stabilizing such a complex. Where the agent disrupts the complex, it can be useful for decreasing the expression of a nucleic acid molecule operatively linked to an Mcl-1 gene regulatory element. Where the agent stabilizes the complex, for example, by altering or inducing an alteration of a component of the complex such as by effecting phosphorylation of a component of the complex, the agent can be useful for increasing the expression of a nucleic acid molecule operatively linked to an Mcl-1 gene regulatory element.

In another embodiment, at least a second protein interacts specifically with a complex formed between the first protein and the regulatory element. Such a method allows the identification of an agent that alters a specific interaction of the second protein with the complex, thereby identifying an agent that can modulate expression of a nucleic acid molecule operatively linked to an Mcl-1 gene regulatory element. The second protein can be, for example, a kinase that can phosphorylate the first protein or another component of a complex comprising the first protein and the regulatory element, and the agent can inhibit a specific interaction of the kinase with complex comprising the first protein, Where phosphorylation of the first protein is involved in expression of a nucleic acid molecule operatively linked to an Mcl-1 gene regulatory element, the agent can be useful for decreasing such expression.

In yet another embodiment, the first protein does not interact specifically with the regulatory element in the absence of the agent. Such a method can be useful to identify an agent that induces a specific interaction of the first protein and the regulatory element to form a complex, thereby identifying an agent that can increase expression of a nucleic acid molecule operatively linked to an Mcl-1 gene regulatory element.

In another embodiment, the first protein and the regulatory element are contacted with a compound that is known to affect expression of a nucleic acid molecule operatively linked to an Mcl-1 gene regulatory element. The compound can be a compound that inhibits expression of the nucleic acid molecule from the regulatory element, for example, an ERK inhibitor. Such a method can be used to identify an agent that alleviates the inhibition of expression due to the compound, thereby identifying an agent that, for example, can increase expression of a nucleic acid molecule operatively linked to an Mcl-1 gene regulatory element in the presence of the inhibitor.

The present invention also relates to a method of identifying an agent that can modulate expression of a nucleic acid molecule operatively linked to an Mcl-1 gene regulatory element. Such a method can be performed, for example, by contacting under suitable conditions an agent and an Mcl-1 gene regulatory element, which is operatively linked to a reporter nucleotide sequence, and detecting an effect on expression of the reporter nucleotide sequence due to the agent. Expression of the reporter nucleotide sequence can be detected, for example, by detecting an RNA transcript of the reporter nucleotide sequence, or by detecting a polypeptide encoded by the reporter nucleotide sequence. A polypeptide reporter, for example, a β-lactamase, chloramphenicol acetyltransferase, adenosine deaminase, aminoglycoside phosphotransferase, dihydrofolate reductase, hygromycin-B phosphotransferase, thymidine kinase, β-galactosidase, luciferase or xanthine guanine phosphoribosyltransferase polypeptide or the like, and can be detected, for example, by detecting radioactivity, luminescence, chemiluminescence, fluorescence, enzymatic activity, or specific binding due to the reporter polypeptide.

The present invention also relates to a method of inhibiting Mcl-1 gene expression in a cell by introducing an Mcl-1 gene regulatory element as disclosed herein into the cell. The introduced regulatory element can, for example, compete with an endogenous Mcl-1 gene regulatory element for one or more cellular proteins that bind specifically to the regulatory element, thereby modulating transcription of the endogenous Mcl-1 gene. Since, as disclosed herein, an Mcl-1 gene alternatively can encode a full length anti-apoptotic Mcl-1 polypeptide and a truncated pro-apoptotic Mcl-1s/ΔTM polypeptide, such a method can be useful for inducing apoptosis of the cell or for increasing viability of the cell, depending upon which Mcl-1 isoform was being expressed in the cell.

The present invention further relates to a method of modulating apoptosis in a cell by introducing into the cell an Mcl-1 gene. In one embodiment, the method is directed to inhibiting apoptosis of the cell by providing for the expression of an Mcl-1 polypeptide encoded by exons 1, 2 and 3 of the Mcl-1 gene in the cell, for example, a neuronal cell. In a second embodiment, the method is directed to inducing apoptosis by providing for expression of an Mcl-1s/ΔTM variant polypeptide encoded by exons 1 and 3 of the Mcl-1 gene in the cell, thereby inducing apoptosis of the cell, for example, a tumor cell. As such, the invention also provides a method of treating a pathologic condition by inhibiting or inducing apoptosis in cells involved in the pathologic condition.

The present invention also relates to a method of inducing apoptosis of a cell by expressing the Mcl-1s/ΔTM polypeptide in the cell. Such a method can be performed, for example, by introducing a polynucleotide encoding the Mcl-1s/ΔTM polypeptide into the cell, and expressing the pro-apoptotic polypeptide. Such a method also can be performed an oligonucleotide that spans a portion of an intron and a portion of exon 2 into the cell. Such an oligonucleotide can hybridize specifically, for example, to an endogenous Mcl-1 gene transcript in the cell, particularly to a splice junction involved in splicing of exon 2 into the mature mRNA, such splicing of exon 2 is inhibited, and the Mcl-1s/ΔTM polypeptide is expressed in the cell. As such, the invention also provides a method of treating a pathologic condition by inducing apoptosis in cells involved in the pathologic condition.

The present invention further relates to a method of identifying a cellular factor that can be involved in splicing of an Mcl-1 gene transcript. Such a method can be performed, for example, by contacting a cellular extract with an oligonucleotide that spans an Mcl-1 gene intron-exon splice junction, and detecting a cellular factor that binds specifically to the oligonucleotide, thereby identifying a cellular factor that can be involved in splicing of the Mcl-1 gene transcript. Such a method can be useful, for example, to identify a cellular factor involved in splicing exon 1 of the Mcl-1 gene transcript to exon 3 of the Mcl-1 gene transcript.

In addition, the present invention relates to a method of identifying an agent that induces expression of the Mcl-1s/ΔTM polypeptide in a cell. Such a method can be performed, for example, by contacting a cell with the agent, and identifying the expression of the Mcl-1s/ΔTM polypeptide or a ribonucleic acid molecule encoding the polypeptide in the cell. An agent identified using such a method can be useful for inducing apoptosis of a cell, and can be useful for treating a pathologic condition such as cancer by inducing apoptosis in cells involved in the condition.

The present invention also relates to a method of identifying a cell that expresses the Mcl-1s/ΔTM polypeptide by contacting the cell with a reagent that interacts specifically with the Mcl-1s/ΔTM polypeptide or with a ribonucleic acid molecule encoding the polypeptide. Such a reagent can be, for example, an antibody that binds specifically to Mcl-1s/ΔTM, or an oligonucleotide binds specifically to a nucleic acid molecule encoding Mcl-1s/ΔTM.

BRIEF DESCRIPTION OF THE DRAWINGS

FIG. 1 shows an 8253 nucleotide human genomic DNA sequence containing the Mcl-1 gene. Lower case letters indicate an "ATG" initiator methionine codon, a first intron, a second intron, a "TAG" STOP codon, and 3'-untranslated sequence of the full-length Mcl-1 polypeptide, respectively. The complete genomic sequence has been deposited as GenBank Accession No. AF198614, which is incorporated herein by reference.

FIG. 2A shows reporter plasmids linked to serial deletions of the Mcl-1 5'-flanking sequence in pGL2-Basic. Plasmid nomenclature indicates the amount of Mcl-1 5'-flanking sequence (base pairs) present (the major start site of Mcl-1 transcription is designated as +1 and marked by the arrow; see, also, FIG. 3B). The p(+11)Mcl-1luc plasmid contains a segment of DNA representing nucleotides +11 to +160 of the Mcl-1 5'-untranslated region, which is present in all plasmids in the series.

FIG. 2B shows the results of luciferase expression assays. The abscissa shows "relative luciferase activity" and represents the ratio of the normalized activity of each sample to that of the longest plasmid in the series (p(−1656)Mcl-1luc) assayed in the absence of TPA. The values shown are the mean±S.E. of 5 or 6 independent experiments (the mean value is shown). The relative luciferase activity of the pGL2-Basic insertless control vector averaged 0.005±0.002 (S.E.) and 0.006±0.002 in the absence and the presence of TPA, respectively. A pCMVluc plasmid assayed as a positive control in parallel with the test samples yielded a relative luciferase activity of 0.9±0.2 and 105±11 in the absence and presence of TPA, respectively. The results of these experiments were identical when analyzed with normalization for transfection efficiency (shown) or without normalization. Statistical analysis revealed that the effect of TPA was significant in each case (p<0.001), but that the different plasmids did not differ from each other either in the absence or the presence of TPA. Open bars are "absence of TPA" (basal); closed bars are "presence of TPA" (induced).

FIG. 2C shows the inhibition of Mcl-1 reporter plasmid activity in the presence of an inhibitor of ERK activation. Luciferase activity was calculated as in FIG. 2B, except that normalization with pCMVhGH was not carried out, and the activity of each plasmid (p(−1656)Mcl-1luc or p(−162)Mcl-1luc, which were assayed in separate experiments), was calculated relative to the untreated control for that plasmid. The values shown are the mean±S.E. of 2 or 3 experiments with 1 to 3 replicates per experiment. Open bars are "absence of TPA" (basal); closed bars are "presence of TPA" (induced). Lightly hatched bars are absence of TPA/presence of PD 98059 (ERK inhibitor). Heavily hatched bars are presence of both TPA and PD 98059.

FIG. 3A shows the reduction in transcriptional activity in the absence and presence of TPA upon truncation of the Mcl-1 5'-flanking sequence to nucleotide −107. As in FIG. 2, the abscissa represents relative luciferase activity, which is the ratio of the normalized activity of each sample to that of p(−162)Mcl-1luc assayed in the absence of TPA. The values shown are the mean±S.E. of 5 independent experiments (the mean values are shown). Open bars are "absence of TPA" (basal); closed bars are "presence of TPA" (induced). Numbers in parentheses indicate fold induction due to TPA.

FIG. 3B shows various core regulatory elements present in them −107 base pair region of the Mcl-1 gene 5'-flanking sequence. Bold lettering indicates Ets, Sp1 and SRE transcription factor binding sites, as determined using the Mat-Inspector and TRANSFAC databases. The sequence shown is that of p(−162)Mcl-1luc, which contains 162 bp of Mcl-1 5'-flanking sequence as well as 160 bp of downstream sequence (+1 indicates the major transcriptional start site). The sites of deletion in the plasmids p(−107)Mcl-1luc, p(−51)Mcl-1luc, and p(+11)Mcl-1luc are indicated by the filled arrows, as is the translation start site. Direct repeats in the region of the SRE are marked with open arrows (CCCCTTT on the coding strand) and elements with dyad symmetry character (6 out of 7 bp) are underlined on the coding strand (TTCCCCT; ATGGGAA). Two adjacent initiator sequences (YYAXT/AYY) at the major start site of transcription are marked by bold overlining. The asterisks mark the first and last nucleotides of the oligonucleotide probe used for electrophoretic mobility shift assays (SEQ ID NO: 10).

FIG. 3C shows the effect of mutation of the SRE, Ets, and Sp1 binding sites in the −107 region of the Mcl-1 5'-flanking sequence (see Example I). Relative luciferase activity was defined as the ratio between the normalized activity of the mutated plasmid and that of wild-type p(−162)Mcl-1luc. The values shown are the mean±S.E. of 3 independent experiments, except in the case of the ΔSp1 plasmid where an additional experiment was carried out with 6 replicate samples along with 3 wild-type controls (the mean values are shown). ΔSp1 (SEQ ID NO: 7); ΔSRE (SEQ ID NO: 9); and ΔEts (SEQ ID. NO: 5). Open bars are "absence of TPA" (basal); closed bars are "presence of TPA" (induced). Numbers in parentheses indicate fold induction due to TPA.

FIGS. 4A and 4B show the compares the full length Mcl-1 polypeptide and the variant Mcl-1s/ΔTM polypeptide.

FIG. 4A shows compares the predicted amino acid sequence of the full length Mcl-1 polypeptide and the variant Mcl-1s/ΔTM polypeptide. The positions of the BH1, BH2 and BH3 domains are indicated by the boxes. The PEST region is marked with dashed lines. The vertical line indicates the position at which the predicted Mcl-1s/ΔTM gene product diverges from full length Mcl-1 product; the novel sequence for Mcl-1s/ΔTM is indicated by italics. The C-terminal transmembrane domain present in wild type Mcl-1 is indicated by double overlines and underlines.

FIG. 4B is a schematic representation of the predicted full length Mcl-1 polypeptide and the variant Mcl-1s/ΔTM isoform. Specific regions are as indicated in FIG. 4A. Arrow indicates region of exon 1-exon 3 splice.

FIG. 5A shows the intron/exon structure and G/C content of the human Mcl-1 genomic locus. An 8253 base pair region of human genomic DNA containing the Mcl-1 gene was sequenced (see FIG. 1). The three Mcl-1 coding exons are numbered and the 3'-untranslated region (3'UTR) is indicated. The two introns are shown between the exons; the 5'-flanking and 3'-flanking regions are hatched. The regions encoding the BH1, BH2, BH3, and TM domains are indicated; BH2 is encoded by exons 2 and 3. A GGCCCC repeat and two initiator sequences that lie upstream of exon 1 also are indicated by the black dot and upward pointing arrow. Two polyadenylation signals (AATAAA) are shown, with the former representing the full length cDNA and the latter beginning at nucleotide 2425 of the cDNA sequence (see Accession No. AF118124, which is incorporated herein by reference). Alu sequences present in the 5'-flanking and 3'-flanking regions of Mcl-1 are shown; embedded within the upstream Alu sequence is a retrovirus long terminal repeat (LTR), which has the properties of a 3'-LTR (heavily hatched regions). The C+G and CpG content is diagrammed below the sequence.

FIG. 5B shows the exon (bars) and intron (lines) structure of the mcl-1 gene (middle panel), and the alternative splicing that produces Mcl-1$_{s/\Delta TM}$ (upper panel) or Mcl-1$_{wt}$ (lower panel). Numbers on lines indicate nucleotides in the indicated intron. Numbers in bars indicate exon number (1, 2, or 3) or 3' untranslated region (3' UTR). ATG indicates start codon.

DETAILED DESCRIPTION OF THE INVENTION

Figure 5A:
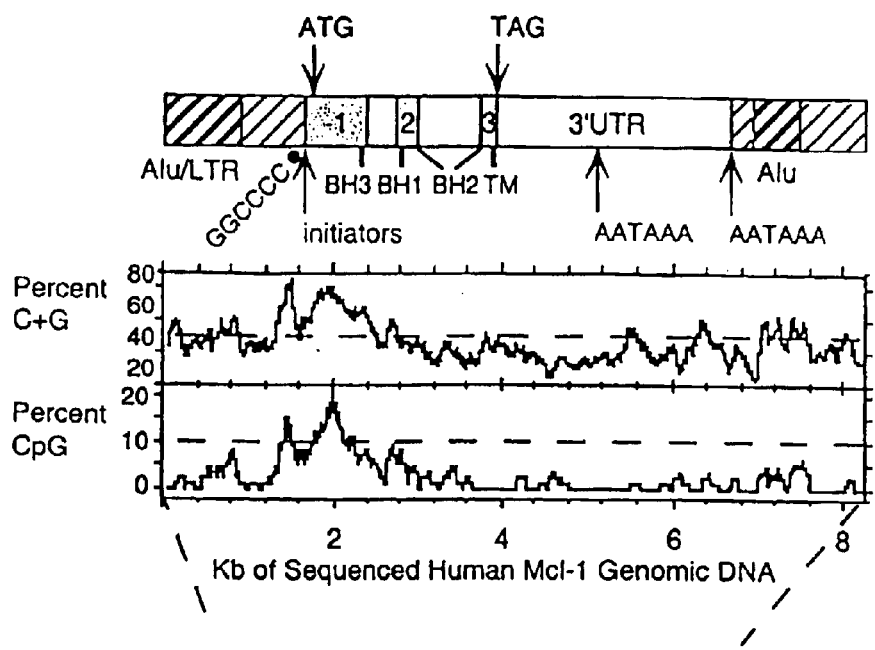
FIGS. 5A and 5B illustrate the structure of the human Mcl-1 gene and show how alternative splicing can occur.

The present invention provides a substantially pure human Mcl-1 gene (FIG. 1), including a gene regulatory region (see FIG. 3B) and a coding region (see FIG. 5A). As disclosed herein, a portion of the 5'-flanking sequence of the Mcl-1 gene acts as a gene regulatory element, and is involved in basal and inducible expression of Mcl-1. As further disclosed, the coding region of the Mcl-1 gene contains three exons and two introns, and encodes two polypeptides, referred to herein as the wild-type or full length Mcl-1 polypeptide and the Mcl-1s/ΔTM variant polypeptide (see FIG. 4A), which arise due to alternative splicing (see FIGS. 5A and 5B). The full length Mcl-1 polypeptide is known to be an anti-apoptotic member of the Bcl-2 family of proteins, and its expression in a cell increases the viability of the cell under conditions in which the cell otherwise would undergo apoptosis. Surprisingly, the Mcl-1s/ΔTM variant has pro-apoptotic activity. As such, its expression in a cell results in the cell undergoing apoptosis. In view of this disclosure, various compositions are provided, as are methods of using the compositions.

Accordingly, the present invention provides substantially pure nucleotide sequences or SEQ ID NO: 1 that act as regulatory elements for expression of an Mcl-1 gene. The term "regulatory element" broadly includes nucleotide sequences that can bind a protein factor involved in transcription or translation of a nucleic acid molecule that is operatively linked to the element; nucleotide sequences that can confer an ability to express or inhibit the expression of an operatively linked nucleic acid molecule; or nucleotide or encoded amino acid sequences that can direct localization of a polypeptide expressed from the nucleic acid molecule to an intracellular or extracellular compartment. Regulatory elements are well known in the art and include, for example, gene regulatory elements such as promoters, enhancers, and silencers; translation regulatory elements such as ribosome binding sequences and polyadenylation signals; and cell compartmentalization signals such as nuclear localization signals, secretory peptide signal sequences, and the like.

Various portions of the Mcl-1 5'-flanking sequence that are involved in basal or inducible expression of the Mcl-1 gene are disclosed herein (see Example I). The term "5'-flanking sequence" or "5'-flanking region" is used generally herein to mean the sequence of the Mcl-1 gene that includes and is upstream (i.e., in a 5' position) of the transcription start site (nucleotide 1657 of SEQ ID NO: 1; see position +1 in FIG. 3B). As such, the 5'-flanking sequence of the Mcl-1 gene is shown as nucleotides 1 to 1657 of SEQ ID NO: 1.

The present invention provides Mcl-1 gene regulatory elements, which can interact specifically with one or more transcription factors or can confer basal or inducible expression upon an operatively linked nucleotide sequence. As used herein, the term "Mcl-1 gene regulatory element" refers to a portion of the Mcl-1 gene 5'-flanking sequence that includes at least about twenty contiguous nucleotides of the nucleotide sequence set forth as nucleotides 1495 to 1657 of SEQ ID NO: 1 (positions −162 to +1 as shown in FIG. 3B), and can interact specifically with a transcription factor or can confer basal or inducible expression on an operatively linked nucleotide sequence. Numerous examples of nucleotide sequences comprising an Mcl-1 gene regulatory element are provided and additional Mcl-1 gene regulatory elements can be identified by detecting the ability of a sequence as disclosed above to bind a transcription factor or to confer basal or inducible expression on a nucleic acid molecule operatively linked thereto using the methods as disclosed herein (see Example II).

As used herein, the term "transcription factor" means a cellular macromolecule that is involved in the regulation of expression of a gene. Transcription factors are well known in the art and include, for example, Sp1 and serum response element (SRE) binding factor (SRF), which, as disclosed herein, interact specifically with an Mcl-1 gene regulatory element, as well as RNA polymerase, transcription factor (TF) IID, TATA binding protein, CAAT binding protein, nuclear factor kappa B, and the like. Methods for determining that a transcription factor interacts specifically with an Mcl-1 gene regulatory element include, for example, electrophoretic mobility shift assays (EMSA) as disclosed herein (Example I), or other methods known in the art such as affinity binding assays.

As used herein, the term "operatively linked" means that two or more molecules are joined together in a functional manner. For example, a gene regulatory element can be operatively linked to a heterologous nucleic acid molecule such as a reporter nucleotide sequence such that, under the appropriate conditions, the reporter nucleotide sequence is transcribed from the gene regulatory element. Similarly, a first encoding nucleotide sequence can be operatively linked to a second encoding nucleotide sequence such that the sequences are in-frame with respect to each other and, therefore, can be transcribed and translated into a polypeptide, which can be a fusion polypeptide.

As used herein, the term "substantially pure" means that the molecule being referred to, generally a polypeptide or a polynucleotide, is in a form that is relatively free of proteins, nucleic acids, lipids, carbohydrates or other materials with which it is naturally associated. A determination that a polynucleotide or a polypeptide of the invention is substantially pure can be determined using well known methods, for example, by performing electrophoresis and identifying the molecule as a discrete band. A substantially pure nucleic acid molecule can be obtained, for example, by cloning the nucleic acid molecule, or by chemical or enzymatic synthesis. A substantially pure polypeptide can be obtained, for example, using methods of protein purification, or by a method of chemical synthesis.

In one aspect, Mcl-1 gene regulatory elements such as the Mcl-1 gene regulatory element set forth as nucleotides 1513 to 1564 of SEQ ID NO: 1 (positions −135 to −92 of FIG. 3B), were identified by the ability to interact specifically with known transcription factors. As shown in FIG. 3B, the Mcl-1 gene regulatory element includes several previously described regulatory elements, including an SRF binding site, an Sp1 binding site, and an Ets binding site. It should be recognized that these previously known sequences, which are specified in FIG. 3B, are not, when present alone in an isolated, discrete form, encompassed within the invention. However, an Mcl-1 gene regulatory sequence of the invention, which contains at least about twenty nucleotides of the sequence set forth as nucleotides 1495 to 1657 of SEQ ID NO: 1, can include one or more of these previously identified regulatory elements. As such, additional Mcl-1 gene regulatory elements are exemplified by a nucleotide sequence containing nucleotides 1495 to 1550 of SEQ ID NO: 1 (positions −162 to −107 of FIG. 3B); or nucleotides 1495 to 1564 of SEQ ID NO: 1 (positions −162 to −92); nucleotides 1495 to 1606 of SEQ ID NO: 1 (positions −162 to −51); nucleotides 1513 to 1550 of SEQ ID NO: 1 (positions −135 to −107); or nucleotides 1513 to 1606 of SEQ ID NO: 1 (positions −135 to −51).

In another aspect, the Mcl-1 gene regulatory elements were identified based on a detection of basal or TPA inducible expression of a reporter nucleotide sequence operatively linked to the regulatory element. Such Mcl-1 gene regulatory elements are exemplified by a sequence including nucleotides 1495 to 1657 of SEQ ID NO: 1 (positions −162 to +1 in FIG. 3B; or nucleotides 1550 to 1657 of SEQ ID NO: 1 (positions −107 to +1); or nucleotides 1606 to 1657 of SEQ ID NO: 1 (positions −51 to +1). A particularly useful Mcl-1 gene regulatory element is exemplified by nucleotides 1495 to 1657 of SEQ ID NO: 1, which correspond to position −162 to +1 in FIG. 3B. As disclosed herein, this sequence confers full basal activity on the Mcl-1 gene, and is fully inducible by an agent such as TPA (see Example II).

The present invention also provides a vector that contains an Mcl-1 gene regulatory element as disclosed herein. Such a vector can be useful for expressing a heterologous nucleic acid molecule that is operatively linked to the Mcl-1 gene regulatory element. As such, the vector also can contain, for example, a multiple cloning site, which can facilitate introduction of a heterologous nucleic acid molecule into the vector such that it is operatively linked to the Mcl-1 gene regulatory element. The invention also provides a host cell containing such a vector, such a cell being useful for maintaining the vector.

A vector of the invention can be useful, for example, for expressing a heterologous nucleic acid molecule in a cell in which an endogenous Mcl-1 gene also is expressed. For example, over-expression of an anti-apoptotic full length Mcl-1 gene product can be associated with a pathologic condition such a cancer. A vector of the invention, which can contain, for example, a heterologous nucleic acid molecule encoding a toxic agent such a ricin A chain operatively linked to the Mcl-1 gene regulatory element, can be introduced into the cells of the cancer patient, and the ricin A chain will be expressed only in those cells that also are expressing Mcl-1.

Apoptosis is a genetically determined cell death program that is critical for the maintenance of tissue homeostasis in the healthy organism. Alterations in apoptosis contribute to the pathological effects seen in a variety of disease states, including cancer and inflammatory disease (see, for example, Rudin and Thompson, *Ann. Rev. Med.* 48:267–281 (1997)). Apoptosis is controlled by evolutionarily conserved sets of genes, with the Bcl-2 family playing a pivotal role (Gross et al., *Genes Devel.* 13:632–640 (1999); Korsmeyer, *Cancer Res.* 59S:1693–1700 (1999). The members of the Bcl-2 family fall into two groups, each having opposing functions. Anti-apoptotic family members, including, for example, Bcl-2, Bcl-$x_L$, and Mcl-1, inhibit cell death, while pro-apoptotic members, including, for example, Bax, Bid, and Bad, increase cell death.

Mcl-1 is a member of the Bcl-2 family that was discovered as a result of a differential screen of genes that are rapidly up-regulated as ML-1 human myeloblastic leukemia cells initiate differentiation along the monocyte pathway (Kozopas et al., *Proc. Natl. Acad. Sci., USA* 90:3516–3520 (1993)). Mcl-1 is expressed at very low levels in immature ML-1 cells, and is up-regulated upon exposure to the monocyte/macrophage differentiation-inducing agent 12-O-tetradecanoylphorbol acetate (TPA). The increase in Mcl-1 mRNA occurs rapidly, being detectable within about 1 hour and approaching a maximum about 7-fold to 10-fold above basal levels at about 3 hours. The increase is transient, and Mcl-1 mRNA levels decline to about 50% of the peak value within 1 day. An increase in the Mcl-1 protein parallels the increase in the mRNA (Yang et al., *J. Cell Biol.* 128:1173–1184 (1995); Yang et al., *J. Cell Physiol.* 166:523–536 (1996)), and precedes the progressive accumulation of differentiated cells on days 1 to 3. In contrast to Mcl-1, Bcl-2 levels remain constant until declining at the terminal stages of differentiation (day 3). Thus, a rapid, transient increase in the expression Mcl-1, but not Bcl-2, occurs during the early stages of TPA-induced ML-1 cell differentiation.

The increase in Mcl-1 seen in the early stages of TPA-induced ML-1 cell differentiation is representative of the high levels of expression seen at early stages of myeloid differentiation in a variety of systems, including cell lines as well as differentiating cells in the intact animal. In ML-1 cells, Mcl-1 expression increased in response to other inducers of monocyte differentiation, but not an inducer of granulocyte differentiation (Yang et al., supra, 1996). Mcl-1 expression can also be induced in other cell lines of myeloid origin, such as HL-60, THP-1, U-937, and K-562 cells, and increases in response to the myelomonocytic growth factor, granulocyte/macrophage-colony stimulating factor (GM-CSF) (Chao et al., *Mol. Cell. Biol.* 18:4883–4898 (1998)). The high levels of expression seen in induced cell lines has a counterpart in the bone marrow in vivo, where Mcl-1 expression is high in myeloid cells at early stages of differentiation. Overall, Mcl-1 is a readily inducible gene in a variety of myeloid systems, prominently expressed at immature stages of differentiation.

Gene transfer experiments have demonstrated that Mcl-1 has viability-enhancing effects. For example, when Mcl-1 was transfected into a murine myeloid progenitor cell line, FDC-P1, its expression prolonged the survival of cells exposed to a variety of apoptosis-inducing stimuli. Similar effects were seen in Chinese hamster ovary cells. These effects, however, were of short duration; cells expressing the transfected Mcl-1 gene product lived about twice as long as controls, but not as long as cells transfected with Bcl-2. Short-term viability-enhancing effects, similar to those seen in transfected cell lines, also were observed in lymphoid cells from Mcl-1 transgenic mice (Zhou et al., *Blood* 92:3226–3239 (1998)). In other experiments, Mcl-1 was found to be a rapidly turned over PEST protein (half life less than 3 hr), providing another contrast to the more stable Bcl-2 protein.

Mcl-1 exhibits a differentiation stage-specific pattern of expression in lymphoid as well as myeloid cells. For example, in B cells at early stages of immortalization with an Epstein Barr virus (EBV) gene product, Mcl-1 expression increases rapidly and transiently. This increase precedes a stable increase in Bcl-2 and may mediate short-term protection of viability. Mcl-1 expression also increases in response to a variety of B cell growth, differentiation, and activation factors. For example, Mcl-1 expression is selectively increased during IL-6-induced differentiation of EBV-immortalized cells, and is subsequently decreased as differentiated cells undergo apoptosis. Likewise, in peripheral blood lymphocytes placed in tissue culture, Mcl-1 (but not Bcl-2) expression correlates with survival, and loss of Mcl-1 expression correlates with apoptosis (Lomo et al., *Cancer Res.* 56:40–43 (1996)). In lymphoid tissues in the intact animal, Mcl-1 expression is abundant in the germinal center, where cells proliferate and undergo affinity maturation, but is low in the small, resting cells in the mantle zone. Bcl-2 demonstrates the opposite pattern of expression, being low in germinal centers and abundant in the mantle zone. Thus, Mcl-1 exhibits a highly regulated pattern of expression, different from that of Bcl-2, in a variety of hematopoietic cells. Opposing patterns of expression of Mcl-1 and Bcl-2 also occur in non-hematopoietic tissues, as in a variety of epithelial tissues, where Bcl-2 is expressed at immature stages of differentiation and Mcl-1 at mature stages.

The increase in Mcl-1 expression involves an increase in transcription, but does not require new protein synthesis (Yang et al., supra, 1996). The signal for increased Mcl-1 expression is transduced through the ERK branch of the MAP kinase family (Townsend et al., *Oncogene* 17:1223–1234 (1998)). This signaling pathway is involved both in maintaining basal Mcl-1 expression and in bringing about the increased expression seen in response to TPA. Thus, cells treated with a specific, non-toxic inhibitor of this pathway, PD 98059, exhibited a decrease from the already low baseline Mcl-1 levels, and cells treated with PD 98059 plus TPA exhibited Mcl-1 levels in the range of those seen in untreated control cells. In addition, Mcl-1 expression is regulated by through an Akt/CREB-mediated pathway (Wang et al., *Mol. Cell. Biol.* 19:6195–6206 (1999)).

Mcl-1 expression induced by a variety of agents, including TPA, which is a differentiation-inducing agent, and colchicine and vinblastine, which act to disrupt microtubules. The role of protein kinase C (PKC) in controlling Mcl-1 expression was assessed by inhibition or down-regulation of the kinase by calphostin C or prolonged treatment with TPA, respectively. PKC activity was required for induction of Mcl-1 expression by TPA, colchicine and vinblastine. The role of microtubule disruption in the signal transduction pathway also was examined. Pretreatment of cells with paclitaxel, which stabilizes microtubules, blocked the increase in Mcl-1 expression produced by colchicine or vinblastine, but not that produced by TPA. The phosphorylation state of members of the mitogen-activated protein kinase (MAP kinase) family was evaluated to examine their role in controlling Mcl-1 expression. Treatment of ML-1 cells with TPA or microtubule-disrupting agents resulted in increased phosphorylation of the MAP kinase proteins extracellular signal-regulated protein kinases 1 and 2 (Erk-1 and Erk-2, respectively). Inhibition of Erk-1 and Erk-2 activation with PD 98059 prevented the up-regulation of Mcl-1 expression by TPA, colchicine and vinblastine. The effect of inhibition of Erk-1 and Erk-2 activity on the transcriptional activation of Mcl-1 was examined. Transient transfection of K-562 cells with a luciferase reporter vector driven by a 1654 base pair segment of the Mcl-1 gene 5' flanking region, followed by treatment with TPA resulted in an approximately 8-fold increase in luciferase activity. This activity was decreased by 78% when the transfected cells were treated with PD 98059 prior to TPA exposure, indicating that activation of Erk-1 and Erk-2 by TPA increases transcription of Mcl-1. Thus, the signals for increased expression of Mcl-1 produced by either differentiation-inducing agents or cytotoxic microtubule-disrupting agents initially are different, but converge to form a common signaling pathway integrated through PKC and phosphorylation of Erk-1 and Erk-2.

Gene transfer experiments showed that low levels of Mcl-1, in the range of the baseline level in the cell lines, had marginal if any effect, whereas higher levels, in the range of those observed after TPA treatment, promoted cell viability (Zhou et al., *Blood* 89:640–643 (1997)). In other studies, the use of PD 98059 to inhibit Mcl-1 expression yielded the following results: 1) when the ERK inhibitor was applied alone, a further decrease from the already low basal Mcl-1 level occurred but was not accompanied by cell death, indicating that this low level does not contribute to the maintenance of viability; 2) when the inhibitor was applied in conjunction with TPA, Mcl-1 was expressed at a level equivalent to the low basal level in untreated control cells (instead of an ~10-fold higher level), and cells died by apoptosis rather than undergoing differentiation (Townsend et al., supra, 1998). These results suggest that, while the baseline levels of Mcl-1 in ML-1 and other immature hematopoietic cell lines are below the threshold necessary for producing an effect, the increased levels induced in cells exposed to TPA contribute to viability-enhancement.

The response of subline of BL41 Burkitt's lymphoma cells, which express about 15-fold more Mcl-1 than the parental line, to a variety of apoptotic signals was examined. When placed under low serum conditions, the Mcl-1-overexpressing cell line exhibited moderate protection from cell death, with viability being extended by about one day as compared to the parental line. However, when placed under low cell density conditions, the Mcl-1 overexpressing cells exhibited a dramatic enhancement of viability. Single cell plating efficiency was increased by greater than 100-fold, from about 0.3% to about 38%. In addition, in liquid culture at low density (approximately $1\times10^4$ cells/ml), the Mcl-1-overexpressing cells continued to grow and remained viable, while the parental cells stopped growing and progressively lost viability. These results demonstrated that Mcl-1 modestly increases cell viability under conditions of low serum, and that Mcl-1 dramatically inhibits cell death under low density conditions.

As disclosed herein, a 162 base pair (bp) segment of the human Mcl-1 gene 5'-flanking sequence mimicked the above-described pattern of endogenous Mcl-1 expression, in that its presence was associated with an approximately 10-fold increase in reporter gene activity in response to TPA, and this induction was suppressed by an inhibitor of ERK activation (see Example I). A region within this 162 bp segment, centered on nucleotide −107(see FIG. 1; SEQ ID NO: 1), was involved in both basal and TPA-induced activity. This region contained sites that bound the transcription factors SRF and Elk-1, and also contained an Sp1 binding site lying between the SRF and Elk-1 binding sites (see FIG. 3B). Mutation of these sites revealed that the coordinate actions of SRF and Ets accounted for about two-thirds of both basal activity and induction by TPA, while Sp1 was involved in basal activity only.

Loss of about two-thirds of the inducibility by TPA, i.e., a decrease from about 10-fold induction to about 3-fold to 4-fold induction, was a common theme that occurred upon truncation of the 162 bp segment to nucleotide −107, and upon addition of the ERK inhibitor, PD 98059, prior to TPA induction (Example I). As a result of this loss of both basal activity and TPA inducibility, the activity of a ΔSRE/ΔEts mutant plasmid in the presence of TPA was equivalent to wild-type activity in the absence of TPA, i.e., it was about 7-fold to 11-fold lower than wild-type activity in the presence of TPA. This result paralleled the observation that, upon inhibition of the ERK pathway, endogenous Mcl-1 levels in the presence of TPA were equivalent to those seen in untreated control cells, and were below the threshold necessary for anti-apoptotic effects (Townsend et al., supra, 1998). These results indicate that Mcl-1 is regulated through a mechanism similar to that utilized by early response genes such as c-Fos, where signal transduction is through MAP kinase and transcriptional activation is through an SRF/Ets complex (Treisman, *Curr. Opin. Genet. Devel.* 4:96–101 (1994); Zinck et al., *EMBO J.* 12:2377–2387 (1993)).

The mechanism of SRF/Ets-mediated transcriptional activation has been studied extensively for c-Fos. The results of those studies indicated that SRF and Ets constitutively associate with the cognate binding sites in DNA, and it was suggested that MAP kinase-induced phosphorylation of the Ets component of the bound SRF/Ets complex increases c-Fos transcription (see, for example, Treisman, supra, 1994; Zinck et al., supra, 1993; Hill and Treisman, *Cell* 80:199–211 (1995)). Since both the unphosphorylated and the phosphorylated complex can bind DNA, identical complexes are frequently seen in EMSAs performed with nuclear extracts from unstimulated and stimulated cells. As disclosed herein, similar results were observed for Mcl-1 using nuclear extracts from untreated and TPA-treated cells (Example I). The use of nuclear extracts from control and TPA-treated cells resulted in equivalent EMSA complexes, as well as the detection of equivalent DNase I hypersensitive sites in the Mcl-1 5'-flanking sequence, indicating that the Mcl-1 gene can exist in "competent" or "pre-activated" state.

As disclosed herein, the Mcl-1 gene regulatory element is involved in regulation of gene expression by an ERK-mediated signal transduction pathway and SRF/Elk-1-mediated transcriptional activation, similar to that of early response genes such as c-Fos. Early-response genes regulated through MAP kinases and SRF/Ets proteins are expressed during the induction of cell differentiation and the stimulation of cell proliferation. c-Fos expression, for example, increases the probability of differentiation in myelomonocytic cell lines and Egr-1 is critical for differentiation along the monocyte lineage. Regulation of Mcl-1 through an SRF/Elk-1-mediated mechanism also can serve to link the control of cell viability to critical steps within the cell differentiation continuum. For example, some early-response genes have apoptosis-inducing effects in immature myeloid cells. Thus, up-regulation of Mcl-1 through mechanisms similar to those utilized by c-Fos, Egr-1, NUR77, and others can maintain viability of the cells as they proceed along a differentiation pathway. The early-response mechanism also can restrict Mcl-1 expression to specific windows of time, for example, the initiation of a step forward in differentiation, thereby preventing prolonged exposure of cells to the viability-promoting gene product and minimizing the possibility of transformation. The results disclosed herein indicate that genes involved both in maintaining cell viability and in cell differentiation are controlled through overlapping regulatory mechanisms.

In addition to the disclosed similarity of Mcl-1 regulation and that of early response genes such a c-Fos, there also are subtle differences. For example, an EMSA complex that formed with an Mcl-1 probe contained SRF and Elk-1 (see Example I), but not Sap-1a, which is a component of corresponding c-Fos complexes. Analogously, the Mcl-1signal transduction pathway involves the ERK pathway, but not the JNK (SAPK) pathway (Townsend et al, supra, 1998). In contrast, c-Fos can be regulated through multiple branches of the MAP kinase/SRF/Ets network. For example, in the BAC-1 macrophage line stimulated through the monocyte-colony stimulating factor receptor (M-CSF-R), c-Fos can be activated by either an SRF/Elk-1 or an SRF/Sap-1 complex; the former is the target of ERK activation and the latter is the target of another member of the MAP kinase family. The result disclosed herein elucidate previous reports indicating that c-Fos has an apoptosis-inducing effect in some contexts but not others (see, for example, Lord et al., *Mol. Cell. Biol.* 13:841–851 (1993); Hu et al., *J. Immunol.* 157:3804–3811 (1994); Jehn and Osborne, *Crit. Rev. Eukaryotic Gene Expr.* 7:179–193 (1997)).

Serum responsiveness of Mcl-1 was prominent in some cell lines but not others, and was particularly notable in B cell lines. Serum stimulation can be effected through a MAP kinase mediated pathway or an alternate pathway involving a G protein-coupled serpentine receptor and SRF but not Ets (Hill et al., *Cell* 81:1159–1170 (1995)). Different cell lines differ in the extent to which serum acts through these different paths, and this can relate to the fact that different cell types exhibit differences in Mcl-1 responsiveness.

In comparison to Mcl-1, down-regulation of Bcl-2 in pre-B cells and immature B cells is mediated through Ets-like πsites(Chen and Boxer, *Mol. Cell Biol.* 15:3840–3847 (1995), which is incorporated herein by reference), but SRF does not appear to be involved. Likewise, the sequence of the upstream regulatory region of Bcl-x reveals potential Ets sites, but no obvious SRE (Grillot et al., *J. Immunol.* 158:4750–4757 (1997)). Conversely, p53 appears to be important in the regulation of expression of a variety of Bcl-2 family members, but not of Mcl-1. Thus, Bcl-2 family members can be regulated independently, but, at the same time, the regulatory networks can be interrelated, as exemplified by the fact that DNA-damaging agents cause p53-dependent up-regulation of Bax and concomitant down-regulation of Bcl-2. Appropriate expression of the Bcl-2 family is critical to the physiologic maintenance of cell viability and death, and inappropriate expression can have pathologic consequences manifested by accelerated death or prolonged viability. The SRF/Ets-mediated mechanism of Mcl-1 regulation as disclosed herein can serve to target Mcl-1 expression to specific physiologic events, similarly to the increased Mcl-1 expression that occurs in cells taking a step forward in differentiation along the myelomonocytic pathway. At the same time, this mechanism for rapid, transient expression can minimize the potential for pathologic consequences.

Mcl-1 expression is increased by various agents that promote the viability, proliferation and differentiation of cells at immature stages of myelomonocytic differentiation. As disclosed herein, Mcl-1 up-regulation by one of these agents, TPA, involves signal transduction through the ERK pathway and transcriptional activation by SRF and Elk-1. As such, regulation of Mcl-1 is similar to that of early response genes such as c-Fos and Egr-1, which influence the commitment of immature myelomonocytic cells to maturation, but can also promote cell death. Significantly, these results indicate that enhancement of viability can be linked to the induction of cell differentiation.

In addition to an Mcl-1 gene regulatory element as disclosed above, the present invention provides a nucleic acid molecule comprising the human Mcl-1 gene. A nucleotide sequence that includes the human Mcl-1 gene is shown in FIG. 1 (SEQ ID NO: 1). Oligonucleotide and polynucleotide portions of the Mcl-1 gene also are provided, as are nucleotide sequences complementary to the Mcl-1 gene or portions thereof.

The term "nucleic acid molecule" is used broadly herein to mean a sequence of deoxyribonucleotides or ribonucleotides that are linked together by a phosphodiester bond. As such, the term "nucleic acid molecule" is meant to include DNA and RNA, which can be single stranded or double stranded, as well as DNA/RNA hybrids. Furthermore, the term "nucleic acid molecule" as used herein includes naturally occurring nucleic acid molecules, which can be isolated from a cell, for example, the Mcl-1 gene as disclosed herein, as well as synthetic molecules, which can be prepared, for example, by methods of chemical synthesis or by enzymatic methods such as by the polymerase chain reaction (PCR), and, in various embodiments, can contain nucleotide analogs or a backbone bond other than a phosphodiester bond.

The terms "polynucleotide" and "oligonucleotide" also are used herein to refer to nucleic acid molecules. Although no specific distinction from each other or from "nucleic acid molecule" is intended by the use of these terms, the term "polynucleotide" is used generally in reference to a nucleic acid molecule that encodes a polypeptide, or a peptide portion thereof, whereas the term "oligonucleotide" is used generally in reference to a nucleotide sequence useful as a probe, a PCR primer, an antisense molecule, or the like. Thus, a polynucleotide of the invention can encode, for example, Mcl-1s/ΔTM, whereas an oligonucleotide of the invention can be used as a probe to detect an intron-exon junction of an Mcl-1 gene. Of course, it will be recognized that an "oligonucleotide" also can encode a peptide. As such, the different terms are used primarily for convenience of discussion.

Various portions of the disclosed Mcl-1 gene are encompassed within the invention. For example, a nucleic acid molecule of the invention can be the coding region of the Mcl-1 gene, for example, a sequence beginning at nucleotides 1727 to 1729, which encode the initiator methionine, and ending at nucleotide 3884, which is the last nucleotide of exon 3, of SEQ ID NO: 1 (see, also, FIG. 1). Additional nucleic acid molecules of the invention are exemplified by the nucleic acid molecule beginning at nucleotide 1657, which is the transcription start site of the Mcl-1 gene, and ending at nucleotide 3884 of SEQ ID NO: 1; the molecule beginning at nucleotide 1495, which is 162 nucleotide upstream (5') to the transcription start site, and ending at nucleotide 3884 of SEQ ID NO: 1; and the nucleic acid molecule containing nucleotides 1 to 8253 of SEQ ID NO: 1.

As disclosed herein, the human Mcl-1 gene encodes two Mcl-1 polypeptide isoforms, which arise due to alternative splicing. The Bcl-2 family of proteins is characterized by the "Bcl-2 homology" (BH) domains, which share high sequence conservation. Bcl-2 and other anti-apoptotic family members contain BH1, BH2, and BH3 domains, which form a hydrophobic cleft, and alteration in the BH1 domain or BH2 domain result in a loss of anti-apoptotic activity. As such, the BH1 and BH2 domains are critical for anti-apoptotic function. Some of the pro-apoptotic family members, including Bax, Bak and Bok, also contain BH1, BH2, and BH3 domains. However, other pro-apoptotic Bcl-2 family members, including Bid, Bad, Bim, contain only the BH3 domain, but not BH1 or BH2. As such, the BH3 domain is a minimum requirement for pro-apoptotic function. This requirement of BH3 can be due to the binding of the exposed BH3 domain to the hydrophobic cleft of anti-apoptotic family members.

In addition to the BH domains, many Bcl-2 family members contain a transmembrane (TM) domain at the carboxyl terminus. The TM domain anchors the protein to intracellular membranes, such as to the outer surface of mitochondria. Removal of the TM domain can result in a reduction in anti-apoptotic activity, indicating that this domain is involved in targeting these gene products for function. However, a TM domain is not present in certain pro-apoptotic members such as Bid or Bad. As such, these observations indicate that the BH1/BH2/BH3 hydrophobic cleft and the membrane anchor contribute to anti-apoptotic activity, and that the BH3 domain is critical for pro-apoptotic function.

Mcl-1 is a member of the Bcl-2 family that is known to inhibit apoptosis and is subject to transcriptional as well as post-transcriptional regulation. As disclosed herein, RNA transcripts from the human Mcl-1 gene can undergo differential splicing to produce an mRNA encoding the anti-apoptotic Mcl-1 gene product, and a second mRNA encoding a shorter pro-apoptotic Mcl-1 variant, designated Mcl-1s/ΔTM. The full length Mcl-1 derives from three coding exons, as compared to the two coding exons present in Bcl-2 and other anti-apoptotic members of this family. The Mcl-1s/ΔTM variant contains an internal deletion that results from joining of the first and third exons with skipping of the central exon (see Example II). This alternative splicing does not affect the BH3 domain, but results in a loss of the BH1, BH2, and TM domains due to omission of an exon and a shift in the reading frame (see FIGS. 5A and 5B). The Mcl-1s/ΔTM variant has structural features similar to pro-apoptotic Bcl-2 family members that contain only the BH3 domain, and, like those pro-apoptotic members, Mcl-1s/ΔTM promoted cell death when expressed in cells (Example II). As such, the Mcl-1 gene is ideally designed for the generation of either an anti-apoptotic Bcl-2-like viability-promoting gene product or, alternatively, a pro-apoptotic BH3-only death-inducing gene product.

Other members of the Bcl-2 family also undergo differential splicing. The splicing of Bcl-x to Bcl-$x_s$, for example, involves the use of an alternate splice site within the coding sequence (Boise et al., *Cell* 74:597–608 (1993)). Bcl-w can also undergo alternate splicing, in this case to an adjacent gene (Gibson et al., *Oncogene* 13:665–675 (1996)). With both Bcl-x and Bcl-2, uppspliced transcripts that read through into the intron have been reported (Jiang and Wu, *Proc. Soc. Expt. Biol. Med.* 25 220:64–72 (1999)). The mechanism involved in the splicing of Mcl-1 differs from that in these other anti-apoptotic family members in that it involves exon skipping, where the subsequent exon is placed in an altered reading frame (Example II). The presence of an intron in Mcl-1 downstream of BH3, along with the conserved intron further downstream in BH2, allows for this ability to skip an exon and to eliminate BH domains critical for anti-apoptotic effects.

Except for Mcl-1, as disclosed herein, the anti-apoptotic Bcl-2 family members contain two exons (see, for example, Grillot et al., supra, 1997; Gibson et al., supra, (1996); Seto et al., *EMBO J.* 7:123–131 (1988)). In comparison, multiple coding exons, separated by 3 to 5 introns, are present in pro-apoptotic family members (see, for example, Choi et al., *Mamm. Genome* 8:781–782 (1997); Hsu et al., *J. Biol. Chem.* 273:30139–30146 (1998); Jiang et al., supra, 1999); the terminal intron is conserved throughout the Bcl-2 family. The introns in the Bax gene, for example, place BH1, BH2, and BH3 on separate exons. A variety of Bax splice variants have been identified, including Baxδ, in which exon 4 is spliced in frame to exon 2 with skipping of exon 3, and Baxγ, in which exon 3 is spliced to exon 1 (with a change in reading frame) with skipping of exon 2 (Oltvai et al., *Cell* 74:609–619 (1993); Jiang et al, supra, 1999). The activity of these Bax variants has not been completely elucidated. Differential splicing also occurs in other pro-apoptotic family members. For example, in Bok/Mtd, exon 2 can be skipped; and in Bim, alternative splicing can alter the N-terminus of the encoded gene product. While the altered splicing of Bok results in retention of a similar function, the different variants of Bim exhibit differences in pro-apoptotic efficacy.

One of the introns in the pro-apoptotic Bax lies downstream of BH3 in a position analogous to the additional (first) intron in Mcl-1 (Oltvai et al., supra, 1993). Other pro-apoptotic family members, namely Bid and Bak, also contain an intron downstream of BH3 (see, for example, Choi et al., supra, 1997; Wang et al., *Genomics* 53:235–238 (1998)). However, in Bid and Bak, these introns are not at positions identical to that of intron 1 in Mcl-1 and the analogous intron in Bax. The alternate upstream splice site within the Bcl-x first coding exon, which is used in the production of Bcl-$x_s$, likewise lies downstream of BH3, although this site again is not located at a position identical to that of the intron in Mcl-1 (Boise et al., supra, 1993). Overall, the multiple introns in pro-apoptotic family members provide a variety of possibilities in terms of differential splicing. Moreover while differential splicing through exon skipping, as disclosed herein for Mcl-1, has not been reported for other anti-apoptotic family members, it does occur among pro-apoptotic family members. The anti-apoptotic members of the Bcl-2 family may prevent cell death by inhibiting the action of adaptor proteins involved in the initiation of the caspase cascade (Moriishi et al., *Proc. Natl. Acad. Sci., USA* 17:9683–9688 (1999)). The pro-apoptotic Bcl-2 proteins could then bind to anti-apoptotic family members and neutralize the block on the adaptor proteins, thereby allowing the death cascade to develop. The pro-apoptotic activity of several Bcl-2 family members that contain only the BH3 domain is regulated in a post-translational manner by protein-protein interactions that make these proteins unavailable to initiate the death pathway. For example Bad is bound in a phosphorylation-dependant manner to 14-3-3 proteins, thereby sequestering the proteins in a form unable to associate with Bcl-2 and Bcl-$x_L$ (Zha et al., *Cell* 87:6219–6228 (1996)). Upon dephosphorylation, Bad translocates to bind Bcl-2 and Bcl-$x_L$, and induces the cell death cascade.

Bim, another Bcl-2 family member that contains only the BH3 domain, is sequestered in the cytoskeletal associated motor complex bound to LC8, a cytoplasmin dynein light chain protein. Apoptotic stimuli disrupt this interaction and the free Bim then can bind to Bcl-2, neutralizing its anti-apoptotic activity and promoting cell death. A third BH3-only protein, Bid, is sequestered in the cytosol in an inactive form and is cleaved by caspase-8 to yield two distinct fragments. The larger fragment can relocalize to the mitochondria, where it acts to antagonize anti-apoptotic Bcl-2 proteins, thereby promoting cell death. Thus, through distinctly different mechanisms, the Bcl-2 family members containing only a BH3 domain are sequestered in an inactive form, and, following a pro-apoptotic stimulus, are released and act as a death inducers by antagonizing the anti-apoptotic activity of Bcl-2-like proteins.

Expression of the two isoforms of Mcl-1, which have opposite functions, can be coordinately regulated. By analogy with other pro-apoptotic Bcl-2 family members that contain only a BH3 domain, the Mcl-1s/ΔTM variant can be sequestered in an inactive form in viable cells through a protein-protein interaction. As such, the present invention provides a means to identify a protein that interacts specifically with an Mcl-1 variant. Assays for identifying protein-protein interactions are well known in the art and include, for example, the two hybrid system of Fields and Song (*Nature* 340:245–246 (1989); see, also, U.S. Pat. No. 5,283,173; Fearon et al., *Proc. Natl. Acad. Sci., USA* 89:7958–7962 (1992); Chien et al., *Proc. Natl. Acad. Sci. USA* 88:9578–9582 (1991), Young, *Biol. Reprod.* 58:302–311(1998), each of which is incorporated herein by reference), the reverse two hybrid assay (Leanna and Hannink, *Nucl. Acids Res.* 24:3341–3347 (1996), which is incorporated herein by reference), the repressed transactivator system (U.S. Pat. No. 5,885,779, which is incorporated herein by reference), the phage display system (Lowman, *Ann. Rev. Biophys. Biomol. Struct.* 26:401–424 (1997), which is incorporated herein by reference), GST/HIS pull down assays, mutant operators (WO 98/01879, which is incorporated herein by reference), the protein recruitment system (U.S. Pat. No. 5,776,689, which is incorporated herein by reference), and the like (see, for example, Mathis, *Clin. Chem.* 41:139–47 (1995), Lam, *Anticancer Drug Res.* 12:145–167(1997); Phizicky et al., *Microbiol. Rev.* 59:94–123 (1995), each of which is incorporated herein by reference).

Since the conserved intron within the BH2 domain near the C-terminus is common to anti-apoptotic and pro-apoptotic family members, these families may have arisen from a primordial member that contained a single intron in the coding region (Herberg et al., *Gene* 211:87–94 (1998)) and undergone gene duplication (Hatakeyama et al., *Int. Immunol.* 10:631–637 (1998)). The addition of introns upstream of the conserved intron would have occurred during the evolution of pro-apoptotic family members. The fact that the position of the additional upstream introns are not precisely conserved among pro-apoptotic family members suggests that these additional introns were added after the divergence of the primordial gene Herberg et al., supra, 1998).

The Mcl-1 gene contains a single additional upstream intron along with the conserved intron near the C-terminus. It thus differs from other ariti-apoptotic family members, which do not contain such introns, as well as from pro-apoptotic family members, which contain multiple upstream introns. As such, Mcl-1 can represent an intermediate in the development of the pro-apoptotic and anti-apoptotic family members. This possibility is consistent with evolutionary analysis suggesting that Mcl-1 and A1 represent a very ancient branch of this family different from the branch containing Bcl-2 and Bcl-x and from that containing Bax, and, with the results disclosed herein, is relevant in view of previous observations concerning the BH3 domain (Kelekar and Thompson, *Trends Cell Biol.* 8:324–330 (1998). The core of the BH3 domain of Bcl-2, Bcl-x, and Bcl-w contains an alanine residue at position 4, while pro-apoptotic family members contain bulkier groups such as isoleucine or valine, which can be involved in binding to the hydrophobic cleft of anti-apoptotic family members (Sattler et al., *Science* 275:983–986 (1997). Mcl-1 contains a valine at this position, typical of the pro-apoptotic family members. In addition, at position –3 from the BH3 core, the other three anti-apoptotic family members (above) have a charged residue (histidine or lysine), while pro-apoptotic members have uncharged residues. In this respect, Mcl-1 also is similar to the pro-apoptotic members in that this residue is a leucine. The presence in Mcl-1 of residues in BH3 that are more typical of pro-apoptotic family members is consistent with the present disclosure that Mcl-1 can be alternately spliced to a pro-apoptotic form.

The present invention provides a substantially pure polynucleotide encoding an Mcl-1s/ΔTM polypeptide having the amino acid sequence set forth in SEQ ID NO: 3 (see, also, FIG. 4A, lower sequence); as well as a polynucleotide complementary to such an encoding polynucleotide. Also provided are polynucleotides encoding peptide portions of Mcl-1s/ΔTM, particularly peptide portions that include at least a portion of amino acids 228 to 271 of SEQ ID NO: 3, which is not represented in the fill length Mcl-1 polypeptide. A polynucleotide of the invention is exemplified by a polynucleotide containing nucleotides 1727 to 2414 of SEQ ID NO: 1 operatively linked to nucleotides 3768 to 3884 of SEQ ID NO: 1, wherein the linked sequence encodes the polypeptide of SEQ ID NO: 3. However, in view of the well known degeneracy of the genetic code, numerous other polynucleotide sequences that encode SEQ ID NO: 3 or a peptide portion thereof readily can be made.

In general, the nucleotides comprising a polynucleotide or oligonucleotide of the invention are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220–5234 (1994); Jellinek et al., *Biochemistry* 34:11363–11372 (1995); Pagratis et al., *Nature Biotechnol.* 15:68–73 (1997), each of which is incorporated herein by reference).

The covalent bond linking the nucleotides of a polynucleotide or oligonucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.*, 22:977–986 (1994); Ecker and Crooke, *BioTechnology* 13:351360 (1995), each of which is incorporated herein by reference). The incorporation of non-naturally occurring nucleotide analogs or bonds linking the nucleotides or analogs can be particularly useful where the polynucleotide or oligonucleotide is to be exposed to an environment that can contain a nucleolytic activity, including, for example, a tissue culture medium or upon administration to a living subject, since the modified polynucleotides can be less susceptible to degradation.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

The invention also provides a vector, which contains a polynucleotide of the invention. The vector can be a cloning vector, which is useful for maintaining the polynucleotide, or can be an expression vector, which contains, in addition to the polynucleotide, regulatory elements useful for expressing the polynucleotide and, where the polynucleotide encodes an polypeptide, for expressing the encoded polypeptide in a particular cell. An expression vector can contain the expression elements necessary to achieve, for example, sustained transcription of the encoding polynucleotide, or the regulatory elements also can be operatively linked to the polynucleotide prior to its being cloned into the vector. In one embodiment, the expression vector contains an Mcl-1 gene regulatory element as disclosed herein.

An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, and can contain other regulatory elements such as an enhancer, which can be tissue specific. The vector also contains elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, Goeddel, ed. (Academic Press, Inc., 1990); Jolly, *Canc. Gene Ther.* 1:51–64 (1994); Flotte, *J. Bioenerg. Biomemb.* 25:37–42 (1993); Kirshenbaum et al., *J. Clin. Invest.* 92:381–387 (1993), each of which is incorporated herein by reference).

Viral expression vectors can be particularly useful for introducing a polynucleotide of the invention into a cell, since viral vectors can infect host cells with relatively high efficiency and can infect specific cell types. For example, a polynucleotide encoding an Mcl-1s/ΔTM polypeptide can be cloned into a baculovirus vector, which then can be used to infect an insect host cell, thereby providing a means to produce large amounts of the encoded Mcl-1s/ΔTM polypeptide. In addition, the viral vector can be derived from a virus that infects vertebrate host cells, particularly mammalian host cells. Viral vectors can be particularly useful for introducing a nucleic acid molecule of the invention, for example, a polynucleotide encoding an Mcl-1s/ΔTM polypeptide, into a mammalian cell, thereby modulating apoptosis in the cell. Viral vectors have been developed for use in mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, *BioTechniques* 7:980–990 (1992); Anderson et al., *Nature* 392:25–30 Suppl. (1998); Verma and Somia, *Nature* 389:239–242(1997); Wilson, *New Engl. J. Med.* 334:1185–1187 (1996), each of which is incorporated herein by reference).

When retroviruses, for example, are used for gene transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. All retroviral vector supernatants used to infect cells are screened for replication competent virus by standard assays such as PCR and reverse transcriptase assays. Retroviral vectors allow for integration of a heterologous gene into a host cell genome, which allows for the gene to be passed to daughter cells following cell division.

A polynucleotide, which can be contained in a vector, can be introduced into a cell by any of a variety of methods known in the art (Sambrook et al., "Molecular Cloning: A laboratory manual" (Cold Spring Harbor Laboratory Press 1989); Ausubel et al., *Current Protocols in Molecular Biology*, John Wiley and Sons, Baltimore, Md. (1994), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell.

Introduction of a polynucleotide into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference). Moreover, viruses are very specialized and can be selected as vectors based on an ability to infect and propagate in one or a few specific cell types. Thus, their natural specificity can be used to target the nucleic acid molecule contained in the vector to specific cell types. As such, a vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events.

The present invention also provides oligonucleotides, which can hybridize specifically to a splice junction of the disclosed Mcl-1 gene or to a polynucleotide encoding an Mcl-1 variant polypeptide as disclosed herein, and oligonucleotides that are complementary to such oligonucleotides. In general, an oligonucleotide of the invention contains at least about ten contiguous nucleotides that are complementary to the Mcl-1 gene sequence that is to be targeted for hybridization; can contain at least about twelve contiguous nucleotides that are complementary; usually contain at least about fifteen nucleotides that are complementary; and particularly contain at least about seventeen nucleotide that are complementary to the targeted Mcl-1 gene sequence, such that the oligonucleotide hybridizes specifically to the target sequence.

An oligonucleotide that can hybridize specifically to a splice junction of the Mcl-1 gene is exemplified by an oligonucleotide that hybridizes to a portion of SEQ ID NO: 1 that includes either nucleotide position 2414, or nucleotide position 2766, or nucleotide position 3013 of SEQ ID NO: 1, or nucleotide position 3786. In particular, an oligonucleotide of the invention hybridizes to a nucleotide sequence of SEQ ID NO: 1 that includes at least three nucleotides 5' and contiguous to specified nucleotide position, and at least three nucleotides 3' and contiguous to the specified nucleotide position. Additional oligonucleotides of the invention can be designed to hybridize specifically to a portion of SEQ ID NO: 1 containing the consensus splice donor and splice acceptor sequences that flank the splice junction (see Muchmore et al., *Nature* 381:335–341 (1996), which is incorporated herein by reference). As such, the oligonucleotide spans an exon-intron junction of the Mcl-1 gene.

It should be recognized that certain EST sequences that previously have been identified are explicitly excluded as being encompassed within the oligonucleotides (or polynucleotides) of the invention, even though they might otherwise appear to meet the requirements of such a sequence of the invention. Thus, the ESTs having GenBank Accession No. AA457098, which consists of nucleotides 2023 to 2414 of SEQ ID NO: 1 operatively linked to nucleotides 3768 to 3801 of SEQ ID NO: 1; GenBank Accession No. AA749362, which consists of nucleotides 2023 to 2414 of SEQ ID NO: 1 operatively linked to nucleotides 3768 to 3784 of SEQ ID NO: 1; GenBank Accession No. AA521010, which consists of nucleotides 2024 to 2414 of SEQ ID NO: 1 operatively linked to nucleotides 3768 to 3918 of SEQ ID NO: 1; and GenBank Accession No. AI435426, which consists of nucleotides 1981 to 2414 of SEQ ID NO: 1 operatively linked to nucleotides 3768 to 3833 of SEQ ID NO: 1, are explicitly excluded from the subject matter considered to be encompassed within present invention. Similarly, oligonucleotides consisting of the sequences set forth as GenBank Accession No. AI204385, AI202072, AA776756, AI340205, AI439001, AA884201 or AA453505, which are EST sequences of an Mcl-1 gene, are not considered oligonucleotides (or polynucleotides) of the invention.

An oligonucleotide that hybridizes specifically to a polynucleotide encoding an Mcl-1s/ΔTM variant polypeptide is exemplified by an oligonucleotide that hybridizes specifically to a nucleotide sequence of SEQ ID NO: 1 that includes nucleotides 2412 to 2414 of SEQ ID NO: 1 linked to nucleotides 3768 to 3770 of SEQ ID NO: 1. Such an oligonucleotide is characterized in that it hybridizes to a nucleic acid molecule containing the splice junction of exon 1 and exon 3 of the Mcl-1 gene. Additional oligonucleotides of the invention include those that can hybridize specifically to a sequence of nucleotides 1 to 1657 of SEQ ID NO: 1, which includes the 5-flanking sequence of the Mcl-1 gene; or to a sequence of nucleotides 2415 to 2765 or nucleotides 3114 to 3767 of SEQ ID NO: 1, which includes the first and second introns, respectively; or to a sequence of nucleotides 6704 to 8253 of SEQ ID NO: 1, which includes Alu-like sequences (see FIG. 5A).

The oligonucleotides of the invention are useful as hybridization probes, PCR primers, antisense molecules, ribozymes, or triplex agents. For use as hybridization probes, the oligonucleotides can be detectably labeled using, for example, a radionuclide, a fluorochrome, or a small molecule such as biotin, thus facilitating detection of the oligonucleotide. An oligonucleotide of the invention, for example, an oligonucleotide to be used as a PCR primer, can also contain an additional nucleotide sequence operatively linked thereto, for example, a nucleotide sequence encoding a restriction endonuclease recognition site. An oligonucleotide useful as an antisense molecule, a ribozyme or a triplexing agent can be designed to target a nucleic acid molecule encoding Mcl-1s/ΔTM and can inhibit translation or cleave the nucleic acid molecule, thereby reducing or inhibiting apoptosis in a cell. An antisense molecule, for example, can bind to an mRNA to form a double stranded molecule that cannot be translated in a cell. Antisense oligonucleotides of about 15 to 25 nucleotides are preferred since they are easily synthesized and can hybridize specifically with a target sequence. In addition, chemically reactive groups such as iron-linked EDTA can be attached to an antisense oligonucleotide, causing cleavage of the RNA at the site of hybridization. An oligonucleotide used as a triplexing agent can stall transcription (Maher et al., *Antisense Res. Devel.* 1:227 (1991); Helene, *Anticancer Drug Design* 6:569 (1991)). Triplexing oligonucleotides can be designed to recognize, for example, a sequence of an Mcl-1 gene regulatory element, thereby reducing or inhibiting the expression of an Mcl-1 isoform in the cell. As such, the oligonucleotides of the invention can be useful for inhibiting the expression of an Mcl-1 polypeptide in a cell. In addition, the oligonucleotides can be used to reduce or inhibit splicing of exon II into a mature mRNA molecule by hybridizing to the splice junction and preventing formation of a splicing complex.

The present invention also provides an Mcl-1s/ΔTM polypeptide, which has an amino acid sequence as set forth in SEQ ID NO: 3. In addition, the invention relates to peptide portions of Mcl-1s/ΔTM. A peptide portion of Mcl-1s/ΔTM generally contains at least three contiguous amino acids of the sequence set forth as amino acids 228 to 271 of SEQ ID NO: 3; usually contains at least about six contiguous amino acids of the sequence set forth as amino acids 228 to 271 of SEQ ID NO: 3; and particularly contains at least about nine or ten contiguous amino acids of the sequence set forth as amino acids 228 to 271 of SEQ ID NO: 3. As disclosed herein, amino acids 228 to 271 are unique to Mcl-1/ΔTM, and are not found in the full length Mcl-1 polypeptide, or in a other proteins pursuant to a database search. The peptides of the invention can be useful, for example, for generating antibodies that bind specifically to Mcl-1s/ΔTM, but not to full length Mcl-1, thus providing a reagent to identify cells expressing Mcl-1s/ΔTM.

If desired, an Mcl-1s/ΔTM polypeptide can comprise a detectable marker such as a FLAG epitope, thus allowing the use of an anti-FLAG antibody to detect the presence of the Mcl-1s/ΔTM polypeptide in the cell (see, for example, Hopp et al., *BioTechnology* 6:1204 (1988); U.S. Pat. No. 5,011,912, each of which is incorporated herein by reference). Other detectable markers such as a c-myc epitope, which can be detected using an antibody specific for the epitope; a polyhistidine sequence, which can be detected using a divalent cation such as nickel ion, cobalt ion, or the like; biotin, which can be detected using streptavidin or avidin; glutathione S-transferase, which can be detected using glutathione; or the like also can be used to identify the presence of an Mcl-1s/ΔTM polypeptide in a cell. Such markers can provide the additional advantage that they can be used as a tag to facilitate isolation of the Mcl-1s/ΔTM polypeptide, for example, where it is desired to obtain a substantially pure Mcl-1s/ΔTM polypeptide preparation.

Where the Mcl-1s/ΔTM is expressed from a polynucleotide, which is introduced into a cell, the presence of the polypeptide in the cell can be detected indirectly by performing northern blot analysis using an oligonucleotide of the invention as a probe, which hybridizes specifically with the encoding polynucleotide, and detecting the presence of the an mRNA encoded by the introduced polynucleotide. In particular, where the cell also is expressing full length Mcl-1, an oligonucleotide is selected that does not substantially cross-hybridize to a nucleic acid molecule encoding the full length Mcl-1. An oligonucleotide of the invention also can be used as a PCR primer, and PCR can be performed to detect the presence of the introduced polynucleotide, or of mRNA expressed from the polynucleotide. If desired, the polynucleotide encoding Mcl-1s/ΔTM can further comprise a nucleotide sequence encoding a detectable marker such as green fluorescent protein, β-galactosidase, luciferase, or the like, thus facilitating detection of the expressed Mcl-1s/ΔTM. Such detectable markers can be particularly useful because cells containing the Mcl-1s/ΔTM then can be detected visually, and because such markers can facilitate high throughput analysis of cells, for example, where it is desired to use a method such as fluorescence activated cell sorting to separate cells containing the Mcl-1s/ΔTM from those lacking it.

Although an Mcl-1s/ΔTM is a relatively large polypeptide and, therefore, would not readily traverse a cell membrane, various methods are known for introducing a polypeptide into a cell. The selection of a method for introducing an Mcl-1s/ΔTM polypeptide into a cell will depend, in part, on the characteristics of the target cell, into which the polypeptide is to be provided. For example, where the target cells, or a few cell types including the target cells, express a receptor, which, upon binding a particular peptide ligand, is internalized into the cell, the Mcl-1s/ΔTM polypeptide can include a domain corresponding to the peptide ligand. Upon binding to the receptor, the Mcl-1s/ΔTM is translocated into the cell by receptor-mediated endocytosis. An Mcl-1s/ΔTM polypeptide also can be contained in a liposome or formulated in a lipid complex, which can facilitate entry of the polypeptide into the cell. An Mcl-1s/ΔTM polypeptide also can be introduced into a cell by engineering the polypeptide to contain a protein transduction domain such as the human immunodeficiency virus TAT protein transduction domain, which facilitates translocation of the Mcl-1s/ΔTM into the cell (see Schwarze et al., *Science* 285:1569–1572 (1999), which is incorporated herein by reference; see, also, Derossi et al., *J. Biol. Chem.* 271:18188 (1996)).

The invention also relates to antibodies that can bind specifically with an epitope of Mcl-1s/ΔTM (SEQ ID NO: 3). Preferably, an antibody of the invention does not bind specifically with an epitope of a full length Mcl-1 polypeptide (SEQ ID NO: 2). As used herein, the term "antibody" is used in its broadest sense to include polyclonal and monoclonal antibodies, as well as antigen binding fragments of such antibodies. An antibody of the invention, or an antigen binding fragment thereof, is characterized by having specific binding activity for an epitope of Mcl-1s/ΔTM, but not for an epitope of a full length Mcl-1 polypeptide.

Ad The term "binds specifically" or "specific binding activity," when used in reference to an antibody of the invention and an epitope of an Mcl-1s/ΔTM polypeptide, means that an interaction of the antibody and the epitope has a dissociation constant of at least about $1\times10^{-6}$, generally at least about $1\times10^{-7}$, usually at least about $1\times10^{-8}$, and particularly at least about $1\times10^{-9}$ or $\times10^{-10}$ or less. As such, Fab, F(ab')$_2$, Fd and Fv fragments of an antibody of the invention, which retain specific binding activity for an Mcl-1s/ΔTM epitope, are included within the definition of an antibody, provided they do not bind specifically with a full length Mcl-1 polypeptide. For purposes of the present invention, an antibody that reacts specifically with an epitope of an Mcl-1s/ΔTM polypeptide is considered to not substantially react with a full length Mcl-1 polypeptide if the antibody has at least a two-fold greater binding affinity, generally at least a five-fold greater binding affinity, and particularly at least a ten-fold greater binding affinity for Mcl-1s/ΔTM as compared to full length Mcl-1.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275–1281 (1989), which is incorporated herein by reference). These and other methods of making, for example, chimeric, humanized, CDR-grafted, single chain, and bifunctional antibodies are well known to those skilled in the art (Winter and Harris, *Immunol. Today* 14:243–246 (1993); Ward et al., *Nature* 341:544–546 (1989); Harlow and Lane, *Antibodies: A laboratory manual* (Cold Spring Harbor Laboratory Press, 1988); Hilyard et al., *Protein Engineering: A practical approach* (IRL Press 1992); Borrabeck, *Antibody Engineering*, 2d ed. (Oxford University Press 1995); each of which is incorporated herein by reference).

Antibodies that bind specifically with Mcl-1s/ΔTM can be raised using the Mcl-1s/ΔTM polypeptide as an immunogen and removing antibodies that crossreact with full length Mcl-1, or by using a peptide portion of Mcl-1s/ΔTM, including at least part of the amino acid sequence shown as amino acids 228 to 271 of SEQ ID NO: 3, since this portion of the Mcl-1s/ΔTM polypeptide is not represented in the full length Mcl-1 polypeptide. A non-immunogenic peptide portion of Mcl-1s/ΔTM can be made immunogenic by coupling the hapten to a carrier molecule such as bovine serum albumin (BSA) or keyhole limpet hemocyanin (KLH), or by expressing the peptide portion as a fusion protein. Various other carrier molecules and methods for coupling a hapten to a carrier molecule are well known in the art (see, for example, by Harlow and Lane, supra, 1988).

The antibodies of the invention are useful for identifying the presence of Mcl-1s/ΔTM in a sample, which can be, for example, a cell that is undergoing apoptosis and in which it is desired to determine whether such apoptosis is the result of Mcl-1s/ΔTM expression, or an extract from a cell in which the Mcl-1s/ΔTM polypeptide was expressed from a recombinant nucleic acid molecule. As such, the antibodies of the invention can be used to purify Mcl-1s/ΔTM from a sample. For example, the antibodies can be bound to a solid matrix such as a chromatography matrix, then the sample can be contacted with the antibodies. Following washing of the matrix to remove unbound material, the Mcl-1s/ΔTM polypeptide, or epitope containing peptide portion thereof, can be released from the antibodies and obtained in a substantially pure form. Methods for attaching antibodies to solid matrices and for eluting bound antigens from such antibodies are well known in the art (see, for example, Harlow and Lane, supra, 1988).

The antibodies of the invention can be useful in immunological assays, for example, to identify a cell expressing Mcl-1s/ΔTM. Where the cell is suspected of being involved in a pathological condition in subject, a tissue sample containing the cell can be obtained from a subject, for example, by a biopsy procedure, and can be prepared for an immunoassay procedure such as a radioimmunoassay (RIA) or an enzyme linked immunosorbent assay (ELISA), or can be examined by microscopy using an immunohistological method.

If desired, a kit incorporating an antibody of the invention can be prepared. Such a kit can contain, in addition to the anti-Mcl-1s/ΔTM antibody, a reaction cocktail that provides the proper conditions for performing an immunological assay, control samples that contain known amounts of Mcl-1s/ΔTM polypeptide and, if desired, a second antibody specific for the anti-Mcl-1s/ΔTM antibody. Such an assay also can include a simple method for detecting the presence or amount of Mcl-1s/ΔTM in a sample. Accordingly, the invention provides such kits, which contain an anti-Mcl-1s/ΔTM antibody.

Methods for raising polyclonal antibodies, for example, in a rabbit, goat, mouse or other mammal, are well known in the art. In addition, monoclonal antibodies can be obtained using methods that are well known and routine in the art (Harlow and Lane, supra, 1988). For example, spleen cells from a mouse immunized with Mcl-1s/ΔTM polypeptide, or an epitopic fragment thereof, can be fused to an appropriate myeloma cell line such as SP/02 myeloma cells to produce hybridoma cells. Cloned hybridoma cell lines can be screened using labeled antigen to identify clones that secrete monoclonal antibodies having the appropriate specificity, and hybridomas expressing antibodies having a desirable specificity and affinity can be isolated and utilized as a continuous source of the antibodies. The antibodies can be further screened for the inability to bind specifically with full length Mcl-1 polypeptide. Such antibodies are useful, for example, for preparing standardized kits as described above. A recombinant phage that expresses, for example, a single chain anti-Mcl-1s/ΔTM antibody also provides an antibody that can used for preparing standardized kits.

A polypeptide of the invention, including an Mcl-1s/ΔTM polypeptide and an anti-Mcl-1s/ΔTM antibody can be labeled so as to be detectable using methods well known in the art (Hermanson, "Bioconjugate Techniques" (Academic Press 1996), which is incorporated herein by reference; Harlow and Lane, supra, 1988). For example, the polypeptide can be labeled with various detectable moieties including a radiolabel, an enzyme such as alkaline phosphatase, biotin, a fluorochrome, and the like. Reagents for labeling, for example, an anti-Mcl-1s/ΔTM antibody can be included in a kit containing the antibody or can be purchased separately from a commercial source.

The present invention provides a method of expressing a nucleic acid molecule in a cell by introducing into the cell an Mcl-1 gene regulatory element of the invention, such that a nucleic acid molecule that is operatively linked to the Mcl-1 gene regulatory element is expressed in the cell. In one embodiment, the Mcl-1 gene regulatory element is introduced into the cell alone, or is in a vector, or contains flanking sequences that facilitate homologous recombination of the regulatory element into a particular locus in a genome. In a proportion of the cells into which the Mcl-1 gene regulatory element is introduced, the regulatory element can integrate into a region of genomic DNA in the cell, such that an endogenous nucleic acid sequence to which the Mcl-1 gene regulatory element is operatively linked is expressed. A genomic DNA library prepared from such cells provides the additional advantage that the Mcl-1 gene regulatory element can be used as a "tag" to identify the operatively linked nucleic acid molecule, thus providing a means to isolate the nucleic acid molecule.

Such a method is useful for identifying endogenous nucleic acid molecules that can be expressed in a cell from the Mcl-1 gene regulatory element. As such, the method provides a means to identify a function of the expressed nucleic acid molecule, which may not otherwise be expressed in the cell or which may otherwise be expressed at a different time in the life cycle or developmental stage of the cell. In general, such a method is performed in a cell in culture, since cells that have incorporated the Mcl-1 gene regulatory element and are expressing a nucleic acid molecule operatively linked to the regulatory element can be cloned, thus providing a relatively homogenous population of cells to be used or examined. However, where the method is performed in a germ cell, a transgenic non-human organism can be obtained such that the effect of expression of the nucleic acid molecule from the Mcl-1 gene regulatory element can be determined in various tissue types and during various stages of development of the organism.

Alternatively, the Mcl-1 gene regulatory element can be operatively linked to a heterologous nucleic acid molecule prior to its introduction into a cell, which can be ex vivo or in vivo. Following introduction into the cell, the heterologous nucleic acid molecule is expressed from the Mcl-1 gene regulatory in the cell. Such a method provides a means for the selective expression of the heterologous nucleic acid molecule in a cell, which can be, for example, a hematopoeitic cell or a cell involved in a pathologic condition. In particular, this method provides a means for expressing a heterologous nucleic acid molecule in a cell that also is expressing an endogenous Mcl-1 gene. As such, the method also is useful as a therapeutic method. For example, the heterologous nucleic acid molecule can be an antisense Mcl-1 nucleotide sequence, which, when expressed coordinately with an endogenous Mcl-1 gene, can prevent expression of the endogenous Mcl-1 gene product. Depending on whether the Mcl-1 gene product is a full length Mcl-1 polypeptide or Mcl-1s/ΔTM, expression of such an heterologous nucleic acid molecule in the cell can have a pro-apoptotic or an anti-apoptotic effect, respectively.

The present invention also provides a method of identifying an agent that can modulate expression of a nucleic acid molecule operatively linked to an Mcl-1 gene regulatory element. Such agents can be useful for modulating apoptosis of a cell. The agent can be, for example, a nucleotide sequence, a peptide, a peptidomimetic, a small organic molecule such as a pharmaceutical agent; or any other molecule. A method of the invention can be performed, for example, by contacting under suitable conditions an Mcl-1 gene regulatory element, at least a first protein that can interact specifically with the regulatory element, and an agent to be tested; and detecting a change in complex formation between the Mcl-1 gene regulatory element and the first protein. A change in complex formation, which can be manifest, for example, by the formation of a complex, the disruption of a complex, or altered stability of a complex, can be detected directly by detecting, for example, a change in the electrophoretic mobility of the complex or of components of the complex, or indirectly by detecting, for example, a change in the expression of a reporter molecule expressed from the regulatory element. Suitable conditions for performing such a method can be provided by performing the method in a reaction mixture in vitro or in a cell.

As used herein, the term "interacts specifically," when used in reference to a first molecule such as a protein and second molecule such as a nucleic acid sequence, means that the two molecule form a complex that is relatively stable under physiologic conditions. As such, the interaction can be characterized by a dissociation of at least about $1 \times 10^{-6}$, generally at least about $1 \times 10^{-7}$, usually at least about $1 \times 10^{-8}$, and particularly at least about $1 \times 10^{-9}$ or $1 \times 10^{-10}$ or less. The interaction can be a direct interaction, for example, of a transcription factor and an Mcl-1 gene regulatory element or of a transcription factor and a protein kinase that can phosphorylate the factor, or can be mediated by an agent that induces, for example, a specific interaction of a transcription factor with a mutant Mcl-1 gene regulatory element. Such a specific interaction is stable under physiological conditions, including, for example, conditions that occur in a living individual such as a human or other vertebrate, or conditions generally used for culturing an organism such as a bacterium or yeast or cells of an organism such as mammalian cells or other cells from a vertebrate or invertebrate organism. Various well known methods can be used to determine whether a two molecule interact specifically, including, for example, equilibrium dialysis, surface plasmon resonance, and the like.

As used herein, the term "modulates apoptosis" means either inducing apoptosis of a cell or increasing cell viability. The term "inducing apoptosis" means that an apoptotic pathway has been activated such that the cell in which the pathway is activated is destined to undergo apoptosis. Such a cell can be identified by detecting the expression or activation of cellular proteins that are characteristic of the apoptotic pathway, or by detecting the characteristic structural changes associated with apoptosis, including, for example, membrane blebbing, chromosomal DNA degradation, and the like. The term "increasing cell viability" or "inhibiting apoptosis" means that a cell remains viable for a longer period of time than would have been expected based on the life span of a corresponding population of cells prior to a treatment such as contact with an agent.

In one embodiment, at least a first protein and the regulatory element interact specifically to form a complex in the absence of the agent. The agent can alter a specific interaction of the protein with the regulatory element, for example, by disrupting a complex comprising the first protein and the regulatory element, or by stabilizing the complex. Where the agent disrupts the complex, it can be useful to decrease the expression of a nucleic acid molecule operatively linked to an Mcl-1 gene regulatory element. Where the agent stabilizes the complex, for example, by altering or inducing an alteration of a component of the complex such as by effecting phosphorylation of a component of the complex, the agent can be useful for increasing the expression of a nucleic acid molecule operatively linked to an Mcl-1 gene regulatory element.

In another embodiment, at least a second protein is included that interacts specifically with a complex formed between the first protein and the regulatory element. Such a method allows the identification of an agent that alters a specific interaction of the second protein with the complex, thereby identifying an agent that can modulate expression of a nucleic acid molecule operatively linked to an Mcl-1 gene regulatory element. The second protein can be, for example, a kinase that can phosphorylate the first protein or another component of a complex comprising the first protein and the regulatory element. and the agent can inhibit a specific interaction of the kinase with complex comprising the first protein, thereby identifying an agent that can decrease expression of a nucleic acid molecule operatively linked to an Mcl-1 gene regulatory element.

In another embodiment, a first protein, which normally would be expected to interact specifically with the regulatory element, does not interact specifically with the regulatory element due, for example, to a mutation in the regulatory element or in a protein that otherwise interacts specifically with the regulatory element. In this method, agents are screened to identify an agent that induces a specific interaction of the first protein and the regulatory element to form a complex. Such a method can be performed, for example, using a mutant Mcl-1 gene regulatory element such as that disclosed as SEQ ID NO: 11, which contains mutations in the transcription factor binding sites, and can identify an agent that allows a specific interaction of one or more proteins with the mutant Mcl-1 gene regulatory element. Such a method can identify an agent that can be useful for treating a pathologic condition that is due to misexpression of an Mcl-1 polypeptide due to a mutation in an Mcl-1 gene regulatory element.

A method of the invention also can be performed by contacting at least a first protein and the regulatory element with a compound that is known to affect expression of a nucleic acid molecule operatively linked to an Mcl-1 gene regulatory element. For example, the compound can be one that inhibits expression of the nucleic acid molecule from the regulatory element, and a method of the invention can be used to identify an agent that alleviates inhibition of expression of the nucleic acid molecule from the regulatory element due to the compound. As disclosed herein, an ERK inhibitor can prevent expression of a nucleic acid molecule operatively linked to an Mcl-1 gene regulatory agent. As such, this system can be used to screen for agents that alleviate this effect of the ERK inhibitor.

The present invention also relates to a method of identifying an agent that can modulate expression of a nucleic acid molecule operatively linked to an Mcl-1 gene regulatory element. Such a method can be performed, for example, by contacting under suitable conditions an agent and an Mcl-1 gene regulatory element, wherein the regulatory element is operatively linked to a reporter nucleotide sequence; and detecting an effect on expression of the reporter nucleotide sequence due to the agent. Expression of the reporter nucleotide sequence can be detected, for example, by detecting an RNA transcript of the reporter nucleotide sequence, or by detecting a polypeptide encoded by the reporter nucleotide sequence. A polypeptide reporter can be, for example, a β-lactamase, chloramphenicol acetyltransferase, adenosine deaminase, aminoglycoside phosphotransferase, dihydrofolate reductase, hygromycin-B phosphotransferase, thymidine kinase, β-galactosidase, luciferase or xanthine guanine phosphoribosyltransferase polypeptide or the like, and can be detected, for example, by detecting radioactivity, luminescence, chemiluminescence, fluorescence, enzymatic activity, or specific binding due to the reporter polypeptide.

The disclosed screening methods are readily adaptable to high throughput analysis and, therefore, can be used to screen combinatorial libraries of agents in order to identify those agents that can modulate expression of a nucleic acid molecule operatively linked to an Mcl-1 gene regulatory element. Methods for preparing a combinatorial library of various molecules, which can be useful as agents for modulating expression of a nucleic acid molecule operatively linked to an Mcl-1 gene regulatory element, either directly or by altering formation of a complex of an Mcl-1 gene regulatory element and a protein that specifically interacts with it, are well known in the art and include, for example, methods of making a phage display library of peptides, which can be constrained peptides (see, for example, U.S. Pat. Nos. 5,622,699; 5,206,347; Scott and Smith, *Science* 249:386–390 (1992); Markland et al., *Gene* 109:13–19 (1991), each of which is incorporated herein by reference); a peptide library (U.S. Pat. No. 5,264,563, which is incorporated herein by reference); a peptidomimetic library (Blondelle et al., supra, 1995); a nucleic acid library (O'Connell et al., supra, 1996; Tuerk and Gold, supra, 1990; Gold et al., supra, 1995, each of which is incorporated herein by reference); an oligosaccharide library (York et al., *Carb. Res.*, 285:99–128, (1996); Liang et al., *Science*, 274:1520–1522, (1996); Ding et al., *Adv. Expt. Med. Biol.*, 376:261–269, (1995),each of which is incorporated herein by reference); a lipoprotein library (de Kruif et al., *FEBS Lett.*, 399:232–236, (1996), which is incorporated herein by reference); a glycoprotein or glycolipid library (Karaoglu et al., *J. Cell Biol.*, 130:567–577 (1995), which is incorporated herein by reference); or a chemical library containing, for example, drugs or other pharmaceutical agents (Gordon et al., *J. Med. Chem.*, 37:1385–1401 (1994); Ecker and Crooke, *Bio/Technology*, 13:351–360 (1995), each of which is incorporated herein by reference). Nucleic acid molecules can be particularly useful as agents that can modulate the expression of a nucleotide sequence from an Mcl-1 gene regulatory element, since nucleic acid molecules having binding specificity for cellular targets, including cellular polypeptides, exist naturally, and because synthetic molecules having such specificity can be readily prepared and identified (see, for example, U.S. Pat. No. 5,750,342, which is incorporated herein by reference).

The present invention also relates to a method of inhibiting Mcl-1 gene expression in a cell by introducing an Mcl-1 gene regulatory element into the cell. The introduced regulatory element can compete with an endogenous Mcl-1 gene regulatory element for one or more cellular proteins that interact specifically with the regulatory element and effect transcription of the endogenous Mcl-1 gene. Since, as disclosed herein, an Mcl-1 gene alternatively can encode a full length anti-apoptotic Mcl-1 polypeptide or a truncated pro-apoptotic Mcl-1s/ΔTM polypeptide, such a method can be useful for inducing apoptosis or increasing viability of the cell, respectively.

Apoptosis also can be modulated in a cell by introducing into the cell an Mcl-1 gene sequence as disclosed herein. As such, a method of the invention provides a means to inhibit apoptosis of the cell by expressing an Mcl-1 polypeptide encoded by exons 1, 2 and 3 of the Mcl-1 gene sequence in the cell, for example, a neuronal cell. In addition, a method of the invention provides a means to induce apoptosis by expressing an Mcl-1s/ΔTM variant polypeptide encoded by exons 1 and 3 of the Mcl-1 gene sequence in the cell, thereby inducing apoptosis of the cell, for example, a tumor cell. In addition, apoptosis can be induced in a cell by expressing the Mcl-1s/ΔTM polypeptide in the cell. Such a method can be performed, for example, by introducing a polynucleotide encoding the Mcl-1s/ΔTM polypeptide into the cell, and expressing the pro-apoptotic polypeptide. The method also can be performed using an oligonucleotide that spans a portion of an intron and a portion of exon 2 into the cell. Such an oligonucleotide can hybridize specifically, for example, to an endogenous Mcl-1 gene transcript in the cell, particularly to a splice junction involved in splicing of exon 2 into the mature mRNA, such that splicing of exon 2 is inhibited and the Mcl-1s/ΔTM polypeptide is expressed in the cell.

The present invention also provides methods of treating a subject having a pathologic condition. As used herein, the term "pathologic condition" means a condition that is characterized, at least in part, by an increased or a decreased level of apoptosis or an increased level of proliferation of a population of cells involved in the pathologic condition. As such, a pathologic condition can be identified by comparing a population of cells in a subject suspected of having a pathologic condition with a corresponding population of cells in a normal healthy individual (a control population) and detecting an increased or decreased level of apoptosis or an increased level of proliferation of the cells in the subject as compared to the control. Various neurodegenerative diseases, for example, are characterized by aberrant neuronal cell death due to apoptosis. As such, a method of the invention can be used to treat a subject having such a neurodegenerative disease, for example, by decreasing the expression of an Mcl-1s/ΔTM variant in the neuronal cells, or by increasing the expression of a full length Mcl-1 polypeptide in the cell. Alternatively, pathologic conditions such as cancer are characterized by levels of cell proliferation that are not balanced by equivalent levels of apoptosis. As such, a method of the invention can be used to treat such conditions, for example, by increasing the expression of Mcl-1s/ΔTM in the cells, thereby inducing apoptosis in the cells, or by affecting Mcl-1 expression in cells involved in the pathologic condition in the subject.

A method of the invention can reduce the severity of a pathologic condition in a subject by inducing apoptosis or increasing viability, as appropriate, in cells associated with the pathologic condition in the subject As used herein, the term "reduce the severity of a pathologic condition" means that particular signs or symptoms associated with the pathologic condition qualitatively or quantitatively are lessened. The signs or symptoms to be monitored will be characteristic of a particular pathologic condition and will be well known to skilled clinician, as will the methods for monitoring the signs and conditions. For example, where the pathologic condition is a malignant neoplasia, the skilled clinician can monitor the size or growth rate of a tumor using diagnostic imaging methods, and can determine that the severity of the condition is reduced by detecting a decreased growth rate or decreased size of the tumor. In addition, the clinician can monitor the level of an enzyme, antigen or other biological product that is prognostic of the status of the condition, for example, prostate specific antigen, carninoembryonic antigen, or the like, as relevant. The clinician also can identify a reduction in the severity of the condition simply by the treated subject indicating that he or she feels less nausea, or more strength, or just generally feels better. Where the pathologic condition is vascular stenosis, the clinician can determine whether the severity of the condition is reduced by performing an angiogram, by measuring blood flow through the involved blood vessel, by examining the level of fatigue exhibited by the patient following a particular task, or the like. Where the pathologic condition is an autoimmune disease, the clinician can determine the immunoreactivity of the patient's immunocytes in an appropriate in vitro immunologic assay, can biopsy the involved tissue and examine the histopathologic or immunohistologic status of the tissue, can examine the mobility of joint involved in the condition or the pain associated therewith, or the like.

Various pathologic conditions, including those characterized by an undesirably high or an undesirably low level of apoptosis, can be treated using a method of the invention. Pathologic conditions characterized, in part, by undesirably low levels of apoptosis or high levels of cell proliferation include, for example, malignant neoplasms such as a carcinoma or fibrosarcoma of the breast, prostate, lung, liver, colon, rectum, kidney, stomach, pancreas, ovary, bladder, cervix, uterus, or brain; a glioblastoma; an astrocytoma; or other malignant neoplasm, including metastatic lesions; and benign neoplasms such as benign prostatic hyperplasia, meningioma, hemangioma and angiofibroma. Other such pathologic conditions include, for example, conditions that are associated with undesirably high levels of angiogenesis such as occurs in diabetic retinopathy, corneal graft neovascularization and neovascular glaucoma; epithelial conditions such as psoriasis; and autoimmune diseases such as rheumatoid arthritis, systemic lupus erythematosis, and the like, which are characterized, in part, by the presence in the subject of dysregulated immunocytes, are amenable to treatment using a method of the invention, whereby apoptosis is induced in the cells. Pathologic conditions characterized, in part, by undesirably high levels of apoptosis include, for example, neurodegenerative diseases, and other diseases such as progeria.

Where the pathologic condition is characterized by an abnormally low level of apoptosis due to expression of Mcl-1 in the cells involved in the condition, a method of the invention can be performed by contacting the cells expressing the Mcl-1 gene product in the subject with an Mcl-1 gene regulatory element. The introduced Mcl-1 gene regulatory element then can compete with the endogenous Mcl-1 gene for transcription factors, thereby reducing or inhibiting expression of the endogenous Mcl-1 gene product in the subject and removing the anti-apoptotic effect of the Mcl-1 gene product.

Where the pathologic condition is characterized by an increased proliferation of a population of cells or an abnormally low level of apoptosis, a method of treatment can be performed by contacting the cells involved the pathologic condition with a polynucleotide that encodes the Mcl-1s/ΔTM polypeptide, or by contacting the cells with the Mcl-1s/ΔTM polypeptide, under conditions that facilitate entry of the polynucleotide or polypeptide into the cell. Entry of the polynucleotide into the cell, for example, can be facilitated by incorporating the polynucleotide into a viral vector that can infect the cells. An Mcl-1s/ΔTM polypeptide can be introduced into a cell, for example, by engineering the polypeptide to contain a protein transduction domain such as the human immunodeficiency virus TAT protein transduction domain, which facilitates translocation of the Mcl-1s/ΔTM into the cell (see Schwarze et al., supra, 1999; Derossi et al., supra, 1996). The presence of the Mcl-1s/ΔTM polypeptide in the cells involved in the pathologic condition then can induce apoptosis of the cells.

A method of treatment also can be performed by contacting the cells involved in the pathologic condition in the subject with the Mcl-1 gene as disclosed herein, particularly with a coding region of the gene. It is recognized that, upon introduction into the cell, either the full length Mcl-1 gene product or the Mcl-1s/ΔTM variant can be expressed in the cell; the particular polypeptide expressed in the cell can be identified using the methods as disclosed herein, for example, using an anti-Mcl-1s/ΔTM antibody. If the appropriate polypeptide is expressed in the cells, for example, the Mcl-1s/ΔTM polypeptide where it is desired to induce apoptosis in the cells, no further action is necessary. If, however, the inappropriate polypeptide is expressed, the nucleic acid molecule introduced into the cells can be modified such that the appropriate polypeptide is expressed. For example, where it is desired to express the Mcl-1s/ΔTM polypeptide in the cell, the intron-exon splice sites flanking exon 2 can be mutated by a method such as site-directed mutagenesis such that the splicing only of exon 1 to exon 3 can occur, thereby resulting in expression of the Mcl-1s/ΔTM polypeptide. Such a requirement can be made prior to treating a subject by removing the appropriate cells from the subject and examining the expression pattern of the Mcl-1 gene in vitro.

A polynucleotide or polypeptide of the invention can be administered to the site of the pathologic condition, or by any method that provides the cells associated with the pathologic condition with the polynucleotide or polypeptide. For administration to a living subject, a polypeptide or polynucleotide, which can be in a vector, generally is formulated in a pharmaceutical composition suitable for administration to the subject. Thus, the invention further provides pharmaceutical compositions, which contain an Mcl-1s/ΔTM polypeptide or a nucleic acid molecule of the invention in a pharmaceutically acceptable carrier. As such, the polypeptides and polynucleotides of the invention are useful as medicaments for treating a subject suffering from a pathological condition.

Pharmaceutically acceptable carriers are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the therapeutic agent, for example, on whether an Mcl-1s/ΔTM polypeptide or a polynucleotide encoding such a polypeptide is to be administered; and on the route of administration of the composition, which can include, for example, orally or parenterally such as intravenously, and by injection, intubation, or other such method known in the art. The pharmaceutical composition also can contain an agent such as a diagnostic agent, nutritional substance, toxin, or therapeutic agent, for example, a cancer chemotherapeutic agent.

The polypeptide or encoding polynucleotide can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley, et al., *Trends Biochem. Sci.*, 6:77 (1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating materials particularly useful for preparing a pharmaceutical composition of the invention and for practicing a method of the invention, and other "masked" liposomes similarly can be used, such liposomes extending the time that the therapeutic agent remain in the circulation. Cationic liposomes, for example, also can be modified with specific receptors or ligands (Morishita et al., *J. Clin. Invest.*, 91:2580–2585 (1993), which is incorporated herein by reference). In addition, a nucleic acid molecule can be introduced into a cell using, for example, adenovirus-polylysine DNA complexes (see, for example, Michael et al., *J. Biol. Chem.* 268:6866–6869 (1993), which is incorporated herein by reference).

The route of administration of a pharmaceutical composition of the invention will depend, in part, on the chemical structure of the molecule. Polypeptides and polynucleotides, for example, are not particularly useful when administered orally because they can be degraded in the digestive tract. However, methods for chemically modifying polypeptides, for example, to render them less susceptible to degradation by endogenous proteases or more absorbable through the alimentary tract are well known (see, for example, Blondelle et al., supra, 1995; Ecker and Crook, supra, 1995). In addition, an Mcl-1s/ΔTM polypeptide can be prepared using D-amino acids, or can contain one,or more domains based on peptidomimetics, which are organic molecules that mimic the structure of peptide domain; or based on a peptoid such as a vinylogous peptoid.

A pharmaceutical composition as disclosed herein can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the pharmaceutical composition can be administered by injection, intubation, orally or topically, the latter of which can be passive, for example, by direct application of an ointment, or active, for example, using a nasal spray or inhalant, in which case one component of the composition is an appropriate propellant. A pharmaceutical composition also can be administered to the site of a pathologic condition, for example, intravenously or intra-arterially into a blood vessel supplying a tumor.

The total amount of an Mcl-1s/ΔTM polypeptide or encoding polynucleotide to be administered can be administered to a subject as a single dose, either as a bolus or by infusion over a relatively short period of time, or can be administered using a fractionated treatment protocol, in which multiple doses are administered over a prolonged period of time. One skilled in the art would know that the amount of the pharmaceutical composition to treat a pathologic condition in a subject depends on many factors including the age and general health of the subject as well as the route of administration and the number of treatments to be administered. In view of these factors, the skilled artisan would adjust the particular dose as necessary. In general, the formulation of a composition of the invention and the routes and frequency of administration are determined, initially, using Phase I and Phase II clinical trials.

The pharmaceutical composition can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes may be used, for example a stabilizing dry agent such as triulose (see, for example, U.S. Pat. No. 5,314,695).

The present invention further provides a method of identifying a cellular factor that can be involved in splicing of an Mcl-1 gene transcript. Such a method can be performed, for example, by contacting a cellular extract with an oligonucleotide that spans an Mcl-1 gene intron-exon splice junction, and detecting a cellular factor that binds specifically to the oligonucleotide. Such a method can be useful, for example, to identify a cellular factor involved in splicing exon 1 of the Mcl-1 gene transcript to exon 3 of the Mcl-1 gene transcript.

In addition, the present invention provides a method of identifying an agent that induces expression of the Mcl-1s/ΔTM polypeptide in a cell. Such a method can be performed, for example, by contacting a cell with the agent, and identifying the expression of the Mcl-1s/ΔTM polypeptide or a ribonucleic acid molecule encoding the polypeptide in the cell. An agent identified using such a method can be useful for inducing apoptosis of a cell. A method of identifying a cell that expresses the Mcl-1s/ΔTM polypeptide by contacting the cell with a reagent that interacts specifically with the Mcl-1s/ΔTM polypeptide or with a ribonucleic acid molecule encoding the polypeptide also is provided. Such a reagent can be, for example, an antibody that binds specifically to Mcl-1s/ΔTM, or an oligonucleotide binds specifically to a nucleic acid molecule encoding Mcl-1s/ΔTM. Routine immunoassays such as a radioimmunoassay or an ELISA or hybridization methods such as northern blot or in situ hybridization or PCR analysis as disclosed herein can be used to identify a cell that expresses the Mcl-1s/ΔTM polypeptide or an encoding polynucleotide.

The following examples are intended to illustrate but not limit the invention.

EXAMPLE I

Mcl-1 Gene Regulatory Elements

This example discloses nucleotide sequences of the Mcl-1 gene that are involved in regulation of Mcl-1 gene expression and demonstrates that enhanced hematopoeitic cell viability due to Mcl-1 expression is linked to myeloid cell differentiation.

A. Experimental Procedures

1. Cell Culture and Induction of Mcl-1 Expression

Human myeloblastic ML-1 cells were grown in RPMI 1640 medium (Biowhittaker) supplemented with 7.5% fetal bovine serum (FBS). These cells were maintained by subculturing three times weekly to a density of about $3 \times 10^5$ cells/ml. Human erythroleukemia K-562 cells were grown in RPMI 1640 media supplemented with 10% FBS, 100 units/ml penicillin and 100 µg/ml streptomycin. These cells were maintained by subculturing to a density of about $2 \times 10^5$ cells/ml. Ramos (EBV negative) Burkitt lymphoma cells were grown in RPMI 1640 supplemented with 10% FBS (Biocell). These cells were maintained by subculturing every 2 days to a density of $5 \times 10^5$ cells/ml.

Sort10 cells are a derivative of HL-60 cells that have been transfected with and selected for high levels of expression of the receptor for macrophage colony stimulating factor. HL-60 cells are similar to ML-1 cells in lineage and differentiation stage but can be stably transfected in some cases. HL-60 and Sort10 cells were maintained as previously described (Yen et al., *Expt. Cell Res.* 229:111–125 (1996); Lowrey et al., *Proc. Natl. Acad. Sci., USA* 89:1143–1147 (1992), each of which is incorporated herein by reference).

2. Construction of a Reporter Plasmid Deletion Series

A 1.7 kilobase (kb) XbaI/XmaI human Mcl-1 genomic fragment representing nucleotide residues -1656 to +160, where +1 denotes the major transcriptional start site, along with a 14 base pair (bp) adapter ligated to its 3' end to place the luciferase gene in the correct reading frame, was inserted into NheI and HindIII digested pGL2-Basic luciferase reporter vector (Promega; Madison Wis.), yielding p(-1656) Mcl-1luc.

Figure 2A:
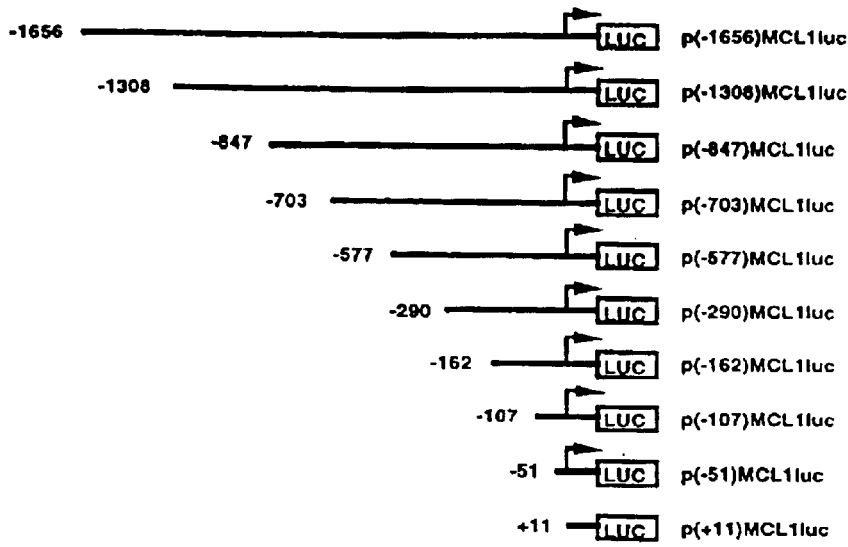
FIGS. 2A to 2C demonstrate that a 162 bp region of the human Mcl-1 5'-flanking sequence directs basal expression and TPA-inducible, ERK-dependent regulation.

A series of 5'-deleted plasmids were constructed by double digestion of p(-1656)Mcl-1luc with SmaI, which cuts just upstream of the Mcl-1 insert, and restriction enzymes known to cut at unique sites within the Mcl-1 insert. Religation resulted in the production of plasmids containing 1308, 847, 703, 577, 290, and 162 bp of Mcl-1 5'-flanking sequence (see FIG. 2A). Additional plasmids were constructed using PCR, including p(-107)Mcl-1luc, p(-51)Mcl-1luc, and p(+11)Mcl-1luc; the PCR products were sequenced to confirm their identity.

3. Site-directed mutagenesis

Specific mutations were introduced into the p(-162)Mcl-1luc plasmid using a two stage PCR method of Chen and Boxer (supra, 1995). The Ets site at nucleotides -129 to -121 was converted from CCGGAAGC (SEQ ID NO: 4) to CCTTAAGC (SEQ ID NO: 5;ΔEts); the Sp1 site at nucleotides -118 to -113 was converted from CCGCCC (SEQ ID NO: 6) to CTGACC (SEQ ID NO: 7;ΔSp1); and the SRE at nucleotides -106 to -97 was converted from CCTTT-TATGG (SEQ ID NO:8) to CCTTCGGCTG (SEQ ID NO: 9;ΔSRE); altered nucleotides are indicated in bold type. All mutations were verified by sequencing. The PCR products containing the desired mutations were digested with BstEII and EcoRI, and ligated into the p(-162)Mcl-1luc plasmid, which had been digested with the same enzymes.

4. Electroporation and Transient Luciferase Expression Assay

A battery of cell lines of myeloid origin was tested for suitability for use in transient transfection with the Mcl-1-luciferase reporter constructs. Upon testing of ML-1, U-937, THP-1, Namalwa, and K-562 cells, the K-562 demonstrated the most readily detectable basal luciferase activity, and was induced by TPA by about 10-fold, which is similar to the level of induction observed endogenously. In the other cell lines, basal luciferase activity was lower than in K-562 cells, but could be optimized; however, TPA did not elicit a reproducibly robust response, producing at most a 2-fold to 3-fold increase in luciferase activity. In control experiments, TPA ellicited a response when a pCMVluc plasmid was used as a positive control.

The reason for the poor TPA responsiveness of Mcl-1 reporter plasmids was investigated in ML-1 cells, which have been utilized for many previous studies (see, for example, Kozopas et al., supra, 1993). The effect of electroporation on the ability of TPA to induce endogenous Mcl-1 gene was monitored, as a robust response was known to occur. Induction was not inhibited by performing the electroporation protocol in the absence of plasmid DNA, but was inhibited upon electroporation in the presence of plasmid DNA, an effect that was observed even with the insertless pGL2-Basic control plasmid. Decreasing the amount of plasmid DNA minimized the inhibition of induction, but resulted in a decrease in luciferase activity to below the level of detection. Thus, while electroporation conditions could be optimized to test for basal expression in other myeloid cell lines besides K-562, the other cell lines could not practically be used for the identification of elements involved in induction by TPA.

Electroporation was carried out with K-562 cells using the following protocol, which was based on preliminary experiments aimed at optimizing luciferase activity. Cells were washed twice and resuspended in PBS ($5 \times 10^6$ cells in 0.5 ml) in the presence of 10 µg luciferase reporter plasmid, along with the pCMVhGH internal control plasmid used in most experiments (10 µg). After incubation on ice for 10 min, cells were electroporated (960 µF and 280 V; Bio-Rad Gene Pulser; Hercules Calif.), placed on ice for 15 min, then incubated at 37° C. ($1 \times 10^5$ cells/ml) in Iscove's Modified Dulbecco's medium supplemented with 10% FBS, 100 units/ml penicillin, and 100 µg/ml streptomycin. After 17 hr, the cell suspension was divided into two portions, one of which was left untreated and the other of which was exposed to $1.7 \times 10^{-9}$ M TPA, which increased Mcl-1 expression in K-562 cells in a manner equivalent to that observed with $5 \times 10^{-10}$ TPA in ML-1 cells (Pahl et al., *Expt. Hematol.* 19:1038–1041 (1991), which is incorporated herein by reference). After 7 hr of exposure to TPA, when induction was at or near a peak level, cells were washed with PBS, then assayed in triplicate for luciferase activity (relative light units; Brasier et al., In "Current Protocols in Molecular Biology (Ausubel et al., eds.; John Wiley & Sons, N.Y. 1995), which is incorporated herein by reference; see pages 9.7.12–9.7.21) using a Microlite ML2250 Microtiter plate luminometer (Dynatech Laboratories; Chantilly Va.).

In most experiments, a human growth hormone reporter plasmid, pCMVhGH (10 µg), was used as a control for transfection efficiency. pCMVhGH yielded a linear increase in activity upon transfection with 2 to 10 µg plasmid, where activity with 2 µg of plasmid was near the limit of sensitivity of the hGH assay, but activity with 5 to 10 µg was sufficiently above background to be accurately quantified. Cotransfection with 5 to 10 µg pCMVhGH did not decrease the basal activity of luciferase reporter plasmids, and caused only a minor reduction in the induction of luciferase activity by TPA (for example, from about 13.5-fold to about 10.5-fold in one experiment examining p(−162)Mcl-1luc and p(−1663)Mcl-1luc in the absence versus the presence of pCMVhGH).

The experimental design, wherein an aliquot of cells electroporated with a test plasmid is divided into two portions, one of which was exposed to TPA and the other of which was not, was selected because CMV-based plasmids are subject to induction by TPA. With this design, cells exposed to TPA and cells not exposed to TPA are derived from the same initial aliquot of electroporated cells and, therefore, do not differ substantially in transfection efficiency. Luciferase activity in both portions of cells was normalized to hGH production (assayed in triplicate in the portion of the sample not exposed to TPA). However, analysis with or without normalization for transfection efficiency did not affect the interpretation of the results.

5. Electrophoretic Mobility Shift Assays

EMSAs were performed using sense strands of a WT Mcl-1 oligonucleotide, representing nucleotides −135 to −92 of the Mcl-1 gene, which contains the potential binding sites for SRF, Ets, and Sp1, or a mutant ΔMcl-1 oligonucleotide, which contains mutations in all three of these binding sites (bold and underlined below). Oligonucleotides, which were prepared by Gibco BRL, except for the Sp1 oligonucleotide, which was from Santa Cruz Biotechnology, Inc., were as follows:

WT Mcl-1: CAACCCTCCGGAAGCTGCCGCCCCTTTC-CCCTTTTATGGGAATA (SEQ ID NO: 10);

ΔMcl-1: CAACCCTCC<u>TT</u>AAGCTGC<u>TG</u>ACCCTTTCCC CTT<u>CGGC</u>TGGAATA (SEQ ID NO: 11; underlining indicates mutations; compare SEQ ID NO: 10);

Sp1: ATTCGATCGGGGCGGGGCGAGC (SEQ ID NO: 12); and c-Fos SRE: CTTACACAGGATGTCCATATTAGGA-CATCT (SEQ ID NO: 13).

Nuclear extracts were prepared (Dignam et al., *Nucl. Acids Res.* 11;1475–1489 (1983)), and protein content was determined using the BioRad Protein Assay kit with bovine serum albumin as a standard. EMSAs were performed as described previously (Latinkic and Lau, *J. Biol. Chem.* 269:23163–23170 (1994)); Wang et al., *Cell* 87:697–708 (1996)). In assays where unlabeled oligonucleotides (10-fold or 100-fold molar excess) or antibodies directed against SRF, Elk-1, SAP-1a, or Sp1 (Santa Cruz Biotechnology, Inc.; Santa Cruz Calif.) were used, these reagents were added to the binding reaction prior to the addition of nuclear extract. The antibodies used in most experiments were selected based on their ability not to interfere with the factor binding to DNA, except in one experiment an anti-Sp1 antibody that interferes with DNA binding was used for that purpose (antibody 1C6; Santa Cruz Biotechnology). Antibody 1C6 recognizes an epitope corresponding to amino acid residues 520 to 538 of Sp1; the DNA binding domain of Sp1 corresponds to residues 537 to 619.

6. Serum or Growth Factor Receptor Stimulation of Cells

Sort10 cells or HL-60 cells were incubated for 24 hr in either standard medium containing 10% FBS or in medium containing 0.3% FBS, then examined for Mcl-1 and Bcl-2. expression by western blot analysis. In other experiments, ML-1 cells were pre-incubated in medium containing 0.3% FBS for 1 day, then exposed to 20% FBS for various times. Samples were collected at 0, 0.5, 1, 2, 4, 8 and 24 hr and examined for Mcl-1 and Bcl-2 expression by western blot analysis.

Western blot analysis was performed as described by Yang et al. (supra, 1995), except that a monoclonal antibody was used. The monoclonal antibody was raised against a bacterially produced, N-terminally His-tagged Mcl-1 protein. Quantitation by densitometric scanning was carried out as described by Townsend et al. (supra, 1998).

8. Statistical Analysis

The results from assays of the luciferase activity of plasmids containing mutations in the SRE, Ets, and Sp1 sites were analyzed using analysis of variance with post-hoc Sheffe testing (Systat 5 for the Macintosh). Results were converted to natural logarithmic values for this analysis. Two way analysis of variance (plasmid x drug) was used to analyze the relative luciferase activity. One way analysis of variance was used to compare the fold-increase with TPA among plasmids.

B. Results

Figure 2B:
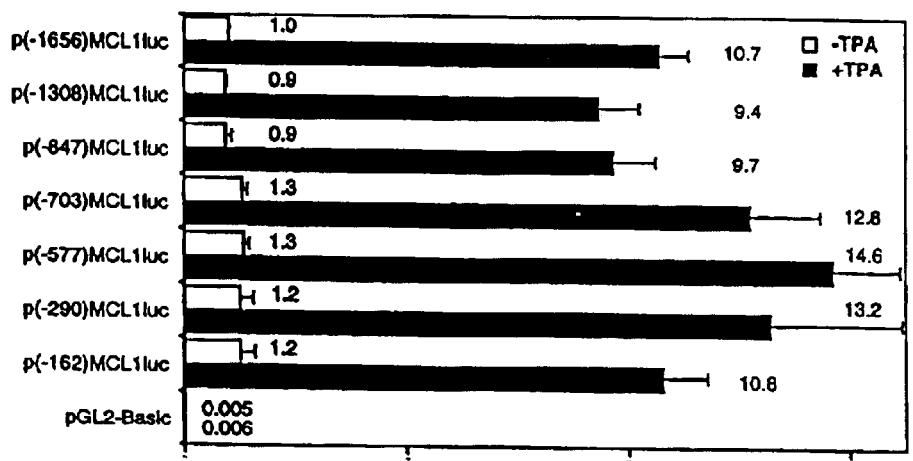

1. A 162 base pair Mcl-1 gene 5'-flanking sequence mediates transcriptional induction by TPA and its suppression by an inhibitor of the ERK pathway p(−1656)Mcl-1luc, which contains a luciferase reporter plasmid under the control of a genomic fragment containing 1656 bp of human Mcl-1 5'-flanking DNA (FIG. 2A; see, also, SEQ ID NO: 1), was introduced into K-562 cells. Luciferase activity was detectable in the absence of TPA and was increased about 10-fold in the presence of TPA (FIG. 2B). These results demonstrate that elements within p(−1656)Mcl-1luc directed both basal Mcl-1 transcription and induction by TPA.

To determine whether a shorter segment of the Mcl-1 5'-flanking sequence could direct transcription, transfections were carried out with a series of plasmids representing progressive 5' deletions of p(−1656)Mcl-1luc. A plasmid containing 162 bp of the Mcl-1 5'-flank, p(−162)Mcl-1 luc, had activity equivalent to that of the full length plasmid, and some intermediately truncated plasmids exhibited slightly, but not significantly, higher activity. The activity of all the plasmid constructs was increased about 9-fold to 11-fold in the presence of TPA, mimicking the increase observed in hematopoietic cell lines that endogenously express Mcl-1.

p(−162)Mcl-1luc and p(−1656)Mcl-1luc were also transfected into ML-1 and U-937 cells, which are myeloid cell lines in which basal activity, but not induction by TPA, could be measured reliably. The basal activity of p(−162)Mcl-1luc was in the range of that seen for p(−1656)Mcl-1 luc, with the ratio of the activity of the former plasmid to the latter being 1.0±0.2 (S.E.; n=3) in ML-1 and 1.3 in U-937 cells. Overall, K-562 cells transiently transfected with a reporter plasmid containing 162 bp of the Mcl-1 5'-flanking sequence constituted a workable system for identifying elements involved in maintaining basal levels Mcl-1 transcription and in bringing about the 10-fold increase in transcription that occurs in response to TPA.

Figure 2C:
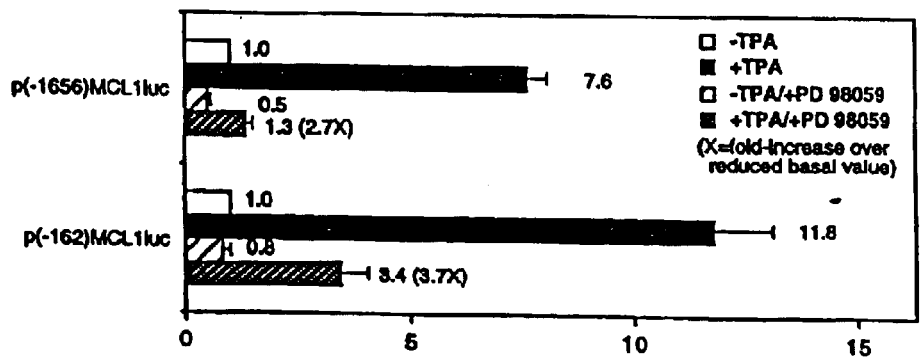

An inhibitor of ERK activation PD 98059 (Alessi et al., *J. Biol. Chem.* 270:27489–27494 (1995)), also was applied to the above K-562 cell transfection system, to determine whether the effect would be similar to that observed in the case of endogenously expressed Mcl-1. This inhibitor substantially, but not completely, inhibited the TPA-induced increase in luciferase activity (FIG. 2C). This result was similar to a previous study showing that PD 98059 substantially, but not completely, inhibited TPA-induced endogenous Mcl-1 expression (Townsend et al., supra, 1998). The ERK inhibitor also caused a decline in basal activity in transfected cells, an effect that also had been noted with respect to endogenous Mcl-1 expression. Overall, transfected cells exposed to PD 98059 exhibited about one-third the level of induction by TPA as seen in cells not exposed to the inhibitor (2.7-fold to 3.7-fold induction over the reduced basal activity in the presence of the inhibitor as compared to 7.6-fold to 11.8-fold induction in its absence). These results demonstrate that transfection with p(−1656)Mcl-1luc or p(−162)Mcl-1luc paralleled endogenous expression with respect to TPA-inducibility and to the substantial suppression of this inducibility by an inhibitor of ERK activation.

2. Truncation of the Mcl-1 5′-flank to nucleotide −107 decreased transcriptional activity in the absence and in the presence of TPA Further truncated plasmids were examined to more clearly delineate the critical regulatory sequence within the 162 bp Mcl-1 5′-flanking sequence. Truncation to nucleotide −107 resulted in a substantial, but not a complete, loss of activity in either the absence or presence of TPA (FIG. 3A), similar to the effect that PD 98059 had on wild-type activity. When compared in the absence of TPA, the activity of p(−107)Mcl-1luc was approximately 20% of that seen with p(−162)Mcl-1luc; and when compared in the presence of TPA, the activity of p(−107)Mcl-1luc was less than 10% of that seen with p(−162)Mcl-1luc. Further truncation to nucleotide −51 resulted in a further loss of activity, to about 5% of the basal activity of p(−162)Mcl-1luc, and there was a complete loss of activity when of all Mcl-1 5′-flanking sequence was deleted. Thus, the −162 to −107 region was important for both basal transcription and the elevated transcription seen in the presence of TPA, but was not the only region contributing to this activity.

With p(−107)Mcl-1luc and, similarly, with p(−51)Mcl-1luc, the activity in the presence of TPA represented an approximately 3.5-fold increase over the corresponding reduced basal value, in contrast to the 10-fold to 12-fold induction observed with longer 5′-flanking sequence, and represented a fold-increase of only about one-third of the maximum value. Thus, truncation to nucleotide −107 resulted in reduced basal activity and reduced induction in the presence of TPA, and the net result was that the activity of the truncated p(−107)Mcl-1luc plasmid in the presence of TPA was in the range of that of the p(−162)Mcl-1luc plasmid in the absence of TPA.

In the −162 to −107 bp region, the human Mcl-1 5′-flank contains potential Ets and Sp1 binding sites, and contains a potential SRE lying immediately downstream (FIG. 3B; SEQ ID NO: 1, nucleotides 1495 to 1550). The presence of Ets and SRF sites provided a parallel to the dyad symmetry region in c-FOS, and suggested that Mcl-1 might be regulated through an SRF/Ets mediated mechanism similar that utilized by early response genes. TPA-induced c-FOS transcription is activated by MAP kinase, which phosphorylates the Ets component of an SRF/Ets complex (see, for example, Treisman, supra, 1994). Such a mechanism would be compatible with the previous described involvement of ERK in the Mcl-1 signal transduction pathway, and would be compatible with the reduced induction observed for p(−107)Mcl-1luc, which retains the potential SRE site, but not the upstream Ets site.

Present and previous data were further considered in the light of the hypothesis that a MAP kinase/SRF/Ets mediated mechanism might play a role in the regulation of Mcl-1, in order to determine whether assessing these sites took priority over testing other potential downstream areas. A mechanism involving signal transduction through ERKs and transcriptional activation by SRF/Ets could account both for the changes observed in transfected cells upon truncation to nucleotide −107 (FIG. 3A) or upon exposure of longer plasmids to PD 98059 (FIG. 2C), as well as the changes seen in endogenously expressing cells upon inhibition of ERK activation (Townsend et al., supra, 1998).

The changes observed in cells transfected with p(−107)Mcl-1luc and those observed in cells endogenously expressing Mcl-1 and exposed to an inhibitor of the ERK pathway exhibited striking similarities. For example, both basal and TPA-induced expression were decreased upon truncation to nucleotide −107 in transfection experiments (FIG. 3A), just as both were comparably decreased upon inhibition of the ERK pathway in endogenously expressing cells. In neither case was expression completely eliminated, TPA causing a reduced level of induction over a reduced basal value upon truncation to nucleotide −107 (FIG. 3A) or upon ERK inhibition, with the reduced induction in both cases being about 3.5-fold. As a result, just as the activity of p(−107)Mcl-1luc in the presence of TPA was equivalent to that of p(−162)Mcl-1luc in its absence, endogenous Mcl-1 expression in cells exposed to PD 98059 plus TPA was in the range of the basal level present in untreated control cells. The parallels between these two systems are indicative of a common underlying pathway and, therefore, the potential SRE and Ets sites, and the Sp1 site between them, in the −107 region of the Mcl-1 5′-flanking sequence were examined.

3. SRF/Ets and Sp1 contribute to basal Mcl-1 gene activity, and the coordinate actions of SRF and Ets are required for maximal induction of Mcl-1 by TPA To assess the functionality of the SRE, Ets, and Sp1 sites, inactivating mutations were introduced into these sites in the context of p(−162)Mcl-1luc (see SEQ ID NOS: 4 to 9). Alteration of the SRE, with or without alteration of the Ets site, reduced but did not eliminate basal activity and reduced but did not eliminate induction by TPA (FIG. 3C). Reduced activity was seen with the ΔSRE (see SEQ ID NO: 9) and ΔEts (see SEQ ID NO: 5) single mutant plasmids as well as with the ΔSRE/ΔEts (see SEQ ID NOS: 9 and 5, respectively) double mutant. These results indicate that the coordinate actions of SRF and Ets were required for maximal activity, as is the case for TPA-induced activation of c-FOS (Treisman, supra, 1994). Alteration of the Sp1 site (see SEQ ID NO: 7) also reduced but did not eliminate basal activity; however, it did not substantially decrease the 9-fold induction observed for TPA in this experiment. These results demonstrate that the SRE and Ets sites were necessary for, and acted coordinately, to produce maximal basal activity and maximal induction by TPA; and that the Sp1 site was necessary for maximal basal activity, but not for induction by TPA.

The activity of the ΔSRE/ΔEts double mutant plasmid in the presence of TPA was in the range of that of the wild-type p(−162)Mcl-1luc plasmid in the absence of TPA. This result was similar to the observations for p(−107)Mcl-1luc, although the wild-type plasmid exhibited slightly lower induction by TPA in the present experiments than it had previously (compare FIG. 3A and FIG. 3C). Additional experiments with the ΔSRE/ΔEts plasmid showed that, on average, basal activity was decreased by about two-thirds (Table 1, row IIA) and the fold-induction by TPA above this reduced basal value was decreased by nearly an equivalent proportion, from a value of about 11-fold to about 4-fold (Table 1, row IIB and C).

Figure 3A:
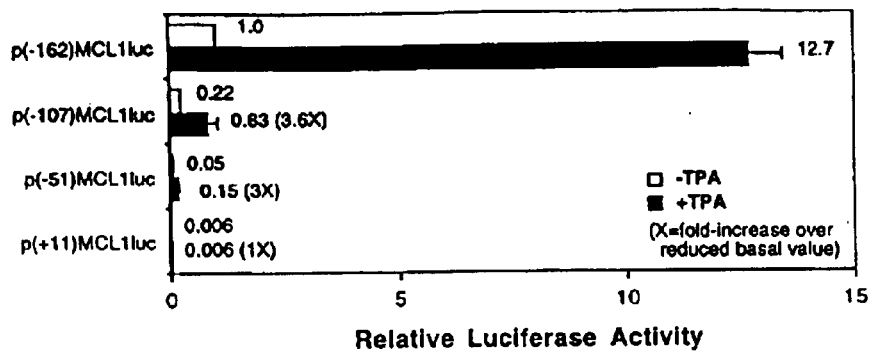
FIGS. 3A to 3C show the influence of the SRE, Ets and Sp1 sites in the −107 base pair region of the human Mcl-1 5'-flanking sequence on basal and TPA-induced transcription.
Figure 3B:
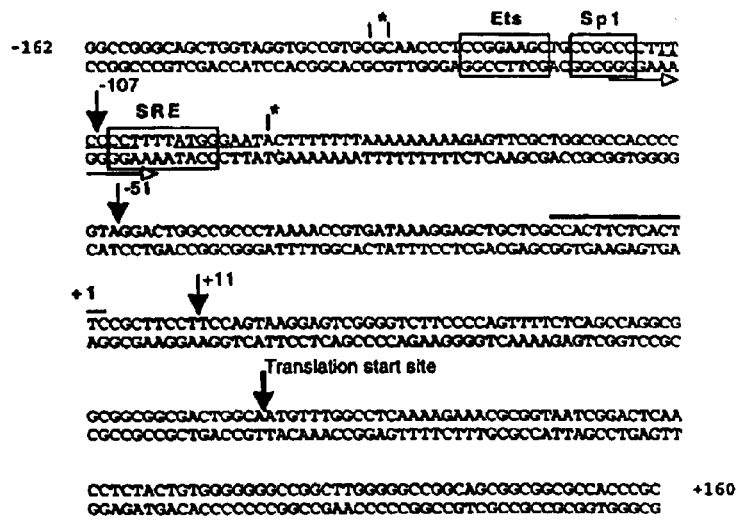
Figure 3C:
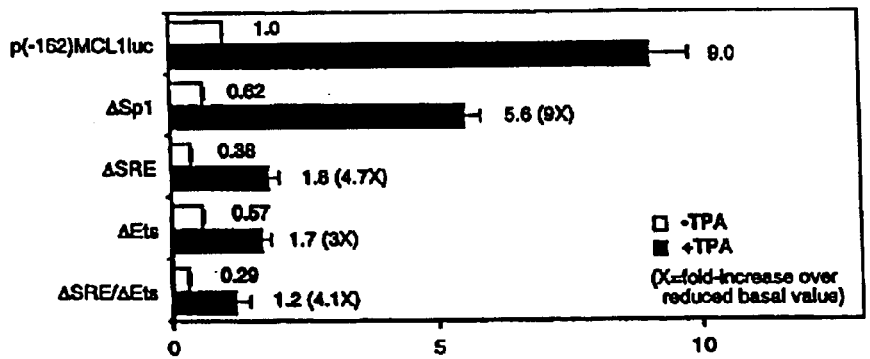

These observations paralleled the experiments involving truncation to nucleotide −107, where the level of induction by TPA was also reduced by approximately two-thirds (Table 1 rows IIIB and IIIC, and FIG. 3A). Here, basal expression was reduced by slightly more than two-thirds (Table 1, row IIIA), which could relate to the fact that the Sp1 site is not present in the truncated plasmid. These findings also paralleled the experiments with wild-type plasmids in the presence of PD 98059, where there was a two-thirds reduction in fold-induction by TPA (Table 1, rows IVC and IVD). Here, basal activity was not reduced to as great an extent as in the other experiments (Table 1, compare row IVA to rows IIA and IIIA). This result can be due to the fact that PD 98059 was added 1.5 hr before the addition of TPA (15.5 hr after electroporation; FIG. 2C), in an experimental design focused on the effect of PD 98059 on induction by TPA above a pre-existing basal level; this design paralleled exactly the design used in previous experiments on endogenous Mcl-1, where a basal level of expression was present before TPA addition (Townsend et al., supra, 1998). Thus, in the transient transfections, the decline in basal activity seen in the presence of PD 98059 represented that occurring from 15.5 to 24 hr (Table 1, row IVA, and FIG. 2C), while the decline with the p(−107)Mcl-1luc or ΔSRE/ΔEts plasmids reflected the entire 24 hr plasmid expression period (Table 1, rows IIA and IIIA; and FIGS. 3A and 3C).

strated a loss of about two-thirds of the TPA-inducibility, to about 3-fold to 4-fold induction above a reduced level of basal activity.

4. SRF, Elk-1, and Sp1 bind to the cognate sites in the −107 region of the Mcl-1 gene EMSAs were carried out with a probe corresponding to nucleotides −135 to −92 of the Mcl-1 5'-flanking sequence, which contains the Ets, SRF, and Sp1 sites in the −107 region of the Mcl-1 5'-flanking sequence to examine the binding of specific nuclear proteins (see FIG. 3B; delineated by asterisks). Four major complexes formed and proteins present in two of these could be identified definitively. Complexes I and II represented specific binding, as their formation was inhibited by excess unlabeled competitor probe, but not by a competitor in which the three sites had been altered. Complex I, but not Complex II, also was inhibited by a competitor representing the c-Fos SRE and Ets site, whereas Complex II, but not Complex I, was inhibited by a competitor representing a consensus Sp1 binding site. These results indicate that Complex I contained SRF and/or an Ets protein, while Complex II contained Sp1. The formation of these complexes was not substantially altered when TPA-treated versus untreated cells were used, similar to results observed by other genes regulated by SRF

TABLE 1

Mcl-1 contains an intron downstream of the BH3 domain in a position conserved in pro-apoptotic Bax but not Bcl-2 or other anti-apoptotic family members, in addition th the conserved intron further downstream.

|  |  | Splice Donor | Splice Acceptor |
|---|---|---|---|
| Consensus: |  | CAG gtaagt..........tttttttttttncag | G |
|  |  | A g cccccccccc t | A |
| Mcl-1 | AC CAC GAG ACG GCC TTC CAA $G_{748}$ | gtaaggg.(351 bp).gcttttctttctcag | GC ATG CTT CTT CGG AAA CTG |
| intron 1 | N H E T V F $Q_{229}$ |  | $G_{230}$ M L R K L D |
| Mcl-1 | CTA GTT AAA CAA AGA GGC $TGG_{996}$ | gtaagtt.(754 bp).tttttgttttctag | GAT GGG TTT GTG GAG TTC |
| intron 2 | L V K Q R G $W_{312}$ |  | $D_{313}$ G F V E Y |
| Bax | AC ATG GAG CTG CAG AG | gtgtggg..........tcctctctcctgcag | G ATG ATT GCC GCC GTG GAC |
| intron 3 | N M E - - L Q |  | R M I A A V D |
| Bax | GAT CAA GAC CAG GGT GGT TGG | gtgagac..........ccctgtctctccagg | GAC GGC CTC CTC TCC TAC |
| terminal intron (intron 5) | I Q D Q G G W |  | D G L L S Y |
| Bcl-2 | ATC CAG GAT AAC GGA GGC TGG | gtaggtg...................tgcag | GAT GCC TTT GTG GAA CTG |
| terminal intron | I Q D N G G W |  | D A F V E L |

The positions of Mcl-1 introns 1 and 2 within the coding sequence are shown. Intron 1 lies just downstream of the BH3 domain and intron 2 lies within the BH2 domain [4]. The length of introns 1 and 2 is indicated in parentheses. An intron at a position similar to that of Mcl-1 intron 1 is present in the Bax gene (intron 3), but not in Bcl-2. An intron at the position of Mcl-1 intron 2 is a highly conserved feature of the Bcl-2 family. Thus, a terminal intron at a similar position is present in Bax (intron 5), as well as Bcl-2 and other family members. Dashes were inserted to optimize sequence alignment [4]. Subscripts indicate the numbering of the full length Mcl-1 cDNA and amino acid sequence (the latter in bold).

Additionally, basal activity in the presence of PD 98059 in transiently transfected cells (Table 1, row IVA; and FIG. 2C) was not reduced as much as in endogenously expressing cells, where basal expression decreased to about 25% of the value in the absence of PD 98059 over the 8.5 hr assay period, although in both systems induction by TPA was reduced to about 3.5-fold. The fact that PD 98059 did not have as marked an effect on basal expression in transient transfections likely reflects a loss of luciferase, in contrast to the decline in endogenously expressing cells which reflects loss of the Mcl-1 protein. This latter difference notwithstanding, a common theme was noted in experiments involving truncation to nucleotide −107, alteration of the SRE and Ets sites, or application of PD 98059 to cells transfected with wild-type plasmids or even cells endogenously expressing Mcl-1; these experiments all demonand Ets (see, for example Zinck et al., supra, 1993; DeFranco et al., Mol. Endocrinol. 7:365–379 (1993)). This result likely is due to the prebound SRF/Ets complex being activated upon stimulation (see Zinck et al., supra, 1993; see, also, below).

The presence of SRF/Ets and Sp1 in Complexes I and II, respectively, was confirmed using antibodies specific for these factors. Antibodies recognizing either SRF or the Elk-1 member of the Ets family caused Complex I to supershift, while an antibody recognizing Sap-1a had no effect. Similarly, an antibody recognizing Sp1 caused Complex II to supershift; the supershifted complex migrated at the same position as Complex I, as demonstrated using an antibody that binds Sp1 and interferes with the binding of Sp1 to its cognate site in DNA. The latter antibody decreased the formation of Complex II. This result confirmed that Sp1 is a component of Complex II.

Complex IV appeared to be a non-specific band, as it could be partially inhibited by high concentrations of various oligonucleotides, including a wild-type Mcl-1 oligonucleotide (SEQ ID NO: 10) and a mutant Mcl-1 (SEQ ID NO: 11) and a 100-fold excess of the Sp1 competitor (SEQ ID NO: 12). Complex III appeared to contain Sp1, as inhibition was seen with the Sp1 competitor but not the c-Fos SRE (SEQ ID NO: 13). Accordingly, Complex III was inhibited by the anti-Sp1 antibody that interfered with DNA binding, although it was not supershifted by the other anti-Sp1 antibody. Others have reported similar observations with a breakdown product of Sp1 that migrated more rapidly than Sp1 and was sensitive to Sp1 binding site competitors but could not be supershifted (see Zhang et al., *J. Biol. Chem.* 369:11425–11434(1994)). These results indicate that SRF and Elk-1, as well as Sp1 and possibly related species, bound specifically to the same sites that were determined, by mutagenesis experiments, to be involved in regulating Mcl-1 transcription.

5. Mcl-1 expression is increased through serum and growth factor receptor stimulated pathways Mcl-1 gene expression is increased by a variety of agents that induce hematopoietic cell differentiation, as exemplified in cells differentiating along the myelomonocytic lineage (Yang et al., supra, 1995). For example, increased Mcl-1 expression occurs upon stimulation of the GM-CSF receptor (GM-CSF-R), which promotes the growth and differentiation of immature myelomonocytic cells (Chao et al., supra, 1998). The macrophage colony-stimulating factor receptor (M-CSF-R) promotes the growth and differentiation of cells at a more mature stage of differentiation, i.e., those cells committed to the monocyte lineage. The M-CSF-R activates MAP kinase and SRF/Ets resulting in increased c-Fos expression (Hipskind et al., *Genes Devel.* 8:1803–1816 (1994)). In view of the above results, and the association of Mcl-1 expression with the stimulation of myelomonocytic growth and differentiation, the effect of the M-CSF-R on Mcl-1 regulation was examined using Sort10 cells, which are transfected with and express high levels of M-CSF-R.

Sort10 cells exhibit enhanced differentiation responsiveness that appears to be mediated through a mechanism similar to that described for previous factor-independent M-CSF-R-transfectants, in which a high density of the transfected receptor triggers downstream events and produces effects in the absence of ligand (Kato et al., *Mol. Cell. Biol.* 9:4069–4073 (1989)). Sort10 cells, rather than cells that endogenously express the M-CSF-R, were used because a similar system using the GM-CSF-R (Chao et al., supra, 1998)) demonstrated that increased Mcl-1 expression occurred in response to stimulation through the GM-CSF-R, and not Bcl-2, as previously believed.

Expression of Mcl-1 was increased in Sort10 cells, while expression of Bcl-2 was unchanged. Expression was examined under standard conditions (10% FBS) or reduced serum (0.3% FBS) conditions; Mcl-1 levels were lowest in non-transfected cells in 0.3% FBS, were higher in the presence of either the transfected M-CSF-R or 10% FBS, and were even higher in the presence of the receptor plus 10% FBS. In four independent experiments carried out in 10% FBS, Sort10 cells exhibited Mcl-1expression that was about 3.9-fold (+/−0.4 S.E.) higher than the level seen in HL-60 cells, and Bcl-2 expression that was 0.6-fold (+/−0.05 S.E.) the level seen in HL-60 cells. Mcl-2 expression in Sort10 cells in 0.3% FBS was about 0.4-fold the level seen in Sort 10 cells incubated in 10% FBS, and 1.7-fold the level seen in HL-60 cells incubated in 0.3% FBS.

The effect of serum on Mcl-1 expression was further assessed in ML-1 and K-562 cell lines. In two independent experiments, Mcl-1 expression increased in response to serum stimulation in ML-1 cells about 4.1-fold (+/−0.2 S.E.) at 2 to 8 hr after transfer to 20% FBS; this level is about 50% of the expression observed in cells treated with TPA. Expression of Bcl-2 did not change substantially, averaging about 1.5-fold at 0.5 to 24 hr. K-562 cells assayed in parallel exhibited even less of a response (about 2.1-fold (+/−0.5 S.E.), and cells transfected with p(−1656)Mcl-1 luc exhibited only a 2-fold increase in luciferase activity upon serum stimulation. However, in separate experiments, an approximately 7-fold increase in response to serum was observed in the B lymphoid Ramos line. Thus, in some hematopoietic cells, Mcl-1 expression can respond to stimuli other than strictly those that specifically affect myelomonocytic cells.

Previous studies had indicated that the increase in Mcl-1 expression due to stimulation with TPA or through the GM-CSF-R was associated with increased transcription and no alteration in protein stability (see, for example, Yang et al., supra, 1996). The results disclosed herein demonstrate that Mcl-1 expression is increased in the presence of a variety of myelomonocytic growth and differentiation stimuli, and also can be affected by serum.

EXAMPLE II

Exon Skipping in Mcl-1 Produces a Pro-Apoptotic Mcl-1 Variant

This example demonstrates that the Mcl-1 gene, in addition to encoding the anti-apoptotic Mcl-1 polypeptide, encodes a shorter pro-apoptotic Mcl-1 variant, designated Mcl-1s/ΔTM.

A. Experimental Procedures

1. Isolation and culture of human cells and cell lines

Human peripheral blood neutrophils and mononuclear (PBMC) cells were isolated from normal healthy donors by dextran sedimentation and plasma-Percoll gradient centrifugation and cultured in RPMI and 10% FCS in teflon pools. Monocyte-derived macrophages were obtained by purification of PBMC and adherence to tissue-culture plasticware in serum-free medium for 1 hr, followed by culture for 4 to 5 days in Iscove's DME and 10% autologous serum (Savill et al., *J. Clin Invest.* 83:865–875 (1989)). Established cell lines, ML-1, THP-1, K562, Jurkat, A549, H441, HepG2 and MCF-7 cells were cultured in RPMI with 10% FCS, 10 mM glutamine, and 50 ug/ml streptomycin and penicillin.

2. RT-PCR detection of Mcl-1s/ΔTM in human cells and cell lines

Total RNA was isolated from peripheral blood cells and cell lines by the RNAEASY system (Qiagen). First strand cDNA was generated by oligodT-primed reverse transcription using avian myeloblastosis virus reverse transcriptase (Promega), under standard conditions (1 $\mu$g RNA in a total volume of 50 $\mu$l). Aliquots (5 $\mu$l) were subjected to amplification with one of several sets of primers, as follows:

| | |
|---|---|
| Mcl-1-F3, 5' GTT GGT CGG GGA ATC TGG TA | (SEQ ID NO: 14); |
| Mcl-1-F4, 5' ATC TCT CGG TAC CTT CGG GA | (SEQ ID NO: 15); |
| Mcl-1-F5 5' GTA AGG AGT CGG GGT CTT CCC | (SEQ ID NO: 16); |
| Mcl-1-R4, 5' AAA TTA ATG AAT TCG GCG GG | (SEQ ID NO: 17); and |
| Mcl-1-R7 5' TCC TCT TGC CAC TTG CTT TTC | (SEQ ID NO: 18). |

Reactions used the following primer combinations: F3 and R4, F4 and R4, or F5 and R7. PCR was performed in a PCT2000 thermal cycler (MJ Research) for 30 cycles, with denaturation at 94° C. for 60 sec, annealing at 60° C. for 60 sec, and extension at 72° C. for 60 sec. Aliquots of the reaction products were subjected to electrophoresis in 1% or 2% agarose gels and visualized by staining with ethidium bromide. The bands obtained with the F4/R4 and F5/R7 primer combinations were excised and cloned using the TOPO pCRII and bi-directional eukaryotic (pCR3.1) TA cloning systems (Invitrogen). Representative minipreps were chosen for sequence analysis using an ABI 373 automatic sequencer. The complete sequence was obtained from multiple clones.

3. Cloning, mapping, and sequencing of the human Mcl-1 genomic locus

A $^{32}$P-labeled probe containing the entire Mcl-1 coding region (p3.2; Kozopas et al., supra, 1993) was used to screen a human leukocyte genomic in the EMBL-3 lambda phage vector (Clontech; Palo Alto Calif.), using standard techniques. The resulting positive clones were characterized by restriction enzyme mapping. Selected restriction enzyme fragments were isolated from agarose gels, subcloned into the pBluescript SKII+vector (Stratagene), and sequenced on both strands.

4. Identification of Mcl-1 transcriptional start sites

Primer extension was performed using an oligonucleotide primer complementary to the Mcl-1 coding region in its upstream portion:

primer #105C, 5'-CCCCACAGTAGAGGTTGAGTCC GATTACCG-3' (SEQ ID NO: 19). Counting the ATG of the initiator methionine as the first through third nucleotides, the primer used represents nucleotides 23 to 52 (or nucleotides 77 to 106 of the p3.2 Mcl-1 cDNA Kozopas, supra, 1993; Townsend et al., J. Biol. Chem. 274:1802–1813 (1999), which is incorporated herein by reference).

The primer was 5'-end-labeling with $^{32}$P using T4 polynucleotide kinase, then approximately $2 \times 10^5$ cpm was hybridized to total RNA (20 µg) from ML-1 cells that had been treated with TPA to increase expression of the Mcl-1 mRNA. As a control, the primer was hybridized in parallel to yeast tRNA (20 µg). Hybridization was carried out at 30° C. for 14 hr in 10 mM Tris-Cl buffer (pH 8.3) containing 150 mM KCl and 1 mM EDTA.

Reverse transcription (RT) with AMV reverse transcriptase (Promega) was carried out at 42° C. for 90 min in 50 mM Tris-Cl buffer (pH 8.3) containing 10 mM $MgCl_2$, 50 mM KCl, 10 mM DTT, deoxynucleotide triphosphates (0.25 mM each), and 0.15 µg/µl actinomycin D. The reaction was stopped by adding EDTA to 20 µM, then the samples were treated with RNase A (Sigma) at 37° C. for 30 min, extracted with phenol/chloroform, precipitated with ethanol, and subjected to gel electrophoresis.

S1 nuclease protection assays were performed using a $^{32}$P-labeled single-stranded DNA probe complementary to Mcl-1 in the upstream portion of the coding sequence and extending into the 5'-flanking region immediately upstream. This probe was prepared using a template representing single stranded Mcl-1 genomic DNA derived from an M13 subclone containing the transcript strand of a 567 base SacI/NotI Mcl-1 genomic subclone from this region (clone SNO.6, which extends from the NotI site within Mcl-1 exon 1 to a SacI site approximately 0.6 kb upstream). The $^{32}$P-labeled #105C oligonucleotide primer (SEQ ID NO: 19) was annealed to this template and the extension reaction was carried out.

The double-stranded DNA product obtained was cleaved at a DraI site 153 nucleotides upstream from the initiator methionine (Townsend et al., supra, 1999). After alkaline denaturing gel electrophoresis, phenol extraction, and ethanol precipitation, the resultant 5'-end labeled single stranded probe, 205 bases in length ($2 \times 10^5$ cpm) was hybridized with total RNA (30 µg) from ML-1 cells treated with TPA (Kozopas et al., supra, 1993). As a control, the probe was hybridized in parallel to yeast tRNA (20 µg). Hybridization (20 µl per reaction) was carried out at 30° C. in 40 mM PIPES (pH 6.4) containing 80% formamide, 400 mM NaCl, and 1 mM EDTA. After 14 hr, the hybridization reaction mixture was diluted by addition of 300 µl S1 nuclease buffer (50 µM sodium acetate (pH 4.5) containing 0.28 M NaCl and 4.5 mM $ZnSO_4$), to which denatured calf thymus DNA (0.02 µg/µl) had been added. Digestion with S1 nuclease (300 units) was carried out at 30° C. for 60 min, and was terminated by the addition of 80 µl of stop buffer (4 M ammonium acetate (pH 8.0) containing 20 mM EDTA and 40 µg/ml yeast tRNA). After ethanol precipitation and resuspension in formamide, the size of the protected fragments was assessed by gel electrophoresis on a DNA sequencing gel alongside a sequencing reaction carried out with the #105C primer and the SNO.6 M13 clone as template. The products of the primer extension reaction were analyzed on the same gel.

5. Transient transfection with Mcl-1s/ΔTM

Two types of expression constructs were prepared for use in transfection into mammalian cells. In one set of constructs, Mcl-1 or the Mcl-1s/ΔTM variant were expressed in the pCR3.1 vector; in the second set of constructs, Mcl-1 was fused to green fluorescent protein (GFP). The Mcl-1 RT-PCR reaction products from the F4/R4 primer pair reactions (SEQ ID NOS: 15 and 17, respectively; cloned in pCR3.1) were digested with KpnI (a KpnI site is present in the F4 primer; SEQ ID NO: 15) and HindIII, as was full length Mcl-1(Mcl-1 clone p3.2 in pBluescriptII SK); Kozopas et al., supra, 1993) and the resulting 5' region of the cDNA was isolated and ligated into pCR3.1 to yield full length Mcl-1 and Mcl-1s/ΔM. The C-terminal GFP fusion protein expression constructs were made by digesting the two Mcl-1 fragments from the pCR3.1 clones using HindIII and PstI, followed by subcloning in frame into pEGFP-C1 (Clontech), to yield pEGFP-Mcl-1 and pEGFP-Mcl-1s/ΔTM. The resulting clones were sequenced using flanking and internal oligonucleotides.

The pCR3.1-based Mcl-1 clones were transiently transfected into subconfluent monolayers of Hela cells in 12 well plates using SUPERFECT (Qiagen). One µg of each of the constructs to be tested —pCR3.1-Mcl-1, pCR3.1-Mcl-1s/ΔTM, pcDNABax (positive control), or insertless pCR3.1 vector (negative control)—was transfected along with pCMV-βgal (1 µg; Promega) as a marker of transfection. The use of a total of 2 µg of DNA per well was based on a series of initial transfections. Forty hr after transfection, cells were fixed, stained for β-gal activity, and analyzed microscopically to assess cell morphology. Transfection experiments were performed in a double blind manner and cells were scored either as having a normal, viable morphology (flat, healthy cells) or an abnormal morphology characteristic of dying cells (dense, rounded, detaching cells). All blue staining cells in each dish were counted and the results were expressed as percentages of cells with viable versus dying phenotypes.

The pEGFP-based vectors (pEGFP-Mcl-1, pEGFP-Mcl-1s/ΔTM, and insertless pEGFP-C1; 0.25 µg each) were transfected into subconfluent monolayers of the human airway epithelial cell line, A549, in chamber slides using LIPOFECTAMINE. Following overnight culture, transfected cells expressing the fusion proteins were examined by confocal microscopy to assess cell death in an analogous manner to that described above.

B. Results

1. Mcl-1s/ΔTM is expressed with full length Mcl-1 in a variety of cell types

A search of GenBank for sequences related to human Mcl-1 revealed several Mcl-1 encoding human EST sequences that contained an internal 248 bp deletion corresponding to nucleotides 749 to 996 of the full length Mcl-1 cDNA. Several internally deleted Mcl-1 cDNAs were present in three distinct cDNA libraries (see GenBank accession Nos. AA457098, AA749362, AA521010 and AI1435426, each of which is incorporated herein by reference). Based on this observation, the present study was undertaken to isolate that human Mcl-1 gene and determine whether Mcl-1 could undergo a form of alternative splicing, similar to Bcl-x.

A distinct transcript representing such an Mcl-1 deletion had not been identified previously by northern blots. However, this result is not necessarily surprising because a 248 bp deletion of the Mcl-1 transcript would represent a decrease in molecular mass of only about 7% as compared to the full length 3.8 kb Mcl-1 transcript (Kozopas et al., supra, 1993; Yang et al., supra, 1996) and because probes that recognize a putative deleted transcript would also recognize full length Mcl-1. Accordingly, RT-PCR using primers from either side of the putative deletion was performed to determine whether an internally deleted Mcl-1 transcript was expressed.

Two distinct cDNA products were obtained by RT-PCR. One cDNA product corresponded to the size expected for full length Mcl-1 and the other cDNA product was approximately 250 bp shorter that the full length Mcl-1 transcript. The two different cDNA products were obtained using three different combinations of primers (F3 and R4, F4 and R4, and F5 and R7; SEQ ID NOS: 14 to 17, SEQ ID NOS: 15 and 17, and SEQ ID NOS: 16 and 18, respectively).

The same results were obtained using RNA from a variety of different types of cells, including primary hematopoietic cells, for example, neutrophils, as well as cell lines of both hematopoietic and non-hematopoietic origin, for example, epithelial cells. The smaller of the cDNA products consistently stained less intensely than the longer product, suggesting that it represented a transcript of lower abundance such as is seen for Bcl-$x_s$, which generally is less abundant than Bcl-$x_L$.

Cloning and sequencing of the two cDNA products obtained by RT-PCR demonstrated that the longer product matched the full length Mcl-1 sequence, while the shorter product contained the internal deletion of nucleotides 749 to 996. This deletion lies within the protein coding sequence (nucleotides 61 to 1110 of the full length Mcl-1 cDNA; GenBank Accession No. L08246; see, also, U.S. Pat. No. 5,470,955, which is incorporated herein by reference). Both the shorter and the longer product contained the Mcl-1 translation start site, as well as a STOP codon (determined by sequencing the products obtained with primers F5 and R7, representing regions upstream (F5) and downstream (R7) of the Mcl-1 coding sequence). These results demonstrate that an mRNA containing a 248 bp deletion within the coding sequence of Mcl-1 is expressed in cells and can encode an Mcl-1 variant polypeptide.

Except for the 248 bp deletion, the nucleotide sequence of the variant Mcl-1 matches that of the full length cDNA. However, the sequence downstream of the deletion is in a different reading frame in the variant. As a result, the predicted amino acid sequence for the Mcl-1 variant polypeptide is identical to that of the full length Mcl-1 upstream of the deletion, but differs at the C-terminus (see FIG. 4A). Specifically, the first 229 amino acid residues of the 271 amino acid internally deleted Mcl-1 variant are identical to full length Mcl-1, while the C-terminal 42 residues are not represented in the full length Mcl-1 (FIGS. 4A and 4B).

The deletion in the Mcl-1 variant does not affect the upstream portion of Mcl-1, which encodes the PEST sequences and the BH3 domain, but substantially affects the downstream portion, which, in full length Mcl-1, encodes the BH1, BH2, and TM domains (FIGS. 4A and 4B). The C-terminus of the deleted Mcl-1 gene product differs not only from the full length Mcl-1, but also does not match any other protein reported in databases. The internally deleted variant, which encodes a shorter protein with an altered C-terminus, was designated Mcl-1s/ΔTM, where "s" designates "short" and "ΔTM" designates the "deleted transmembrane (TM) domain."

The Mcl-1s/ΔTM variant is similar in some respects to pro-apoptotic Bcl-$x_s$ which retains the BH3 domain, but not the BH1 and BH2 domains. However, the Mcl-1s/ΔTM variant is different in that the splicing that yields Bcl-$x_s$ does not affect the reading frame and, therefore, does not affect the C-terminal TM domain. The Mcl-1s/ΔTM variant is similar to other pro-apoptotic family members, including Bid and Bad, which contain the BH3 domain, but not the BH1, BH2, or TM domains. These results indicate that the Mcl-1s/ΔTM variant shares characteristics of pro-apoptotic Bcl-2 family members.

2. The Mcl-1s/ΔTM variant is formed due to skipping of a central coding exon delineated by an intron downstream of BH3 along with the conserved intron in BH1

The splicing that yields Bcl-$x_s$ results from the use of an alternate upstream splice donor site lying within the first coding exon (Boise et al., supra, 1993); Bcl-x, like other anti-apoptotic family members, contains a single intron in the protein coding region (see, for example, Boise et al., supra, 1993; Gibson et al., supra, 1996; Seto et al., supra, 1988).

A determination as to how the Mcl-1s/ΔTM variant arises was made by examining approximately 30 kb of the Mcl-1 human genomic locus. In contrast to other anti-apoptotic family members, Mcl-1 contained three coding exons (FIG. 5A), and contains an intron just downstream of BH3 as well as an intron further downstream in BH2 that is conserved among the apoptotic protein family members (Muchmore et al., supra, 1996). Exon 1 is G/C-rich and encodes the first 229 amino acid residues, including the PEST sequences and the BH3 domain; exon 2 encodes BH1 and a portion of BH2; and exon 3 encodes the remainder of BH2 and the C-terminal TM domain (FIG. 5A).

Figure 5B:
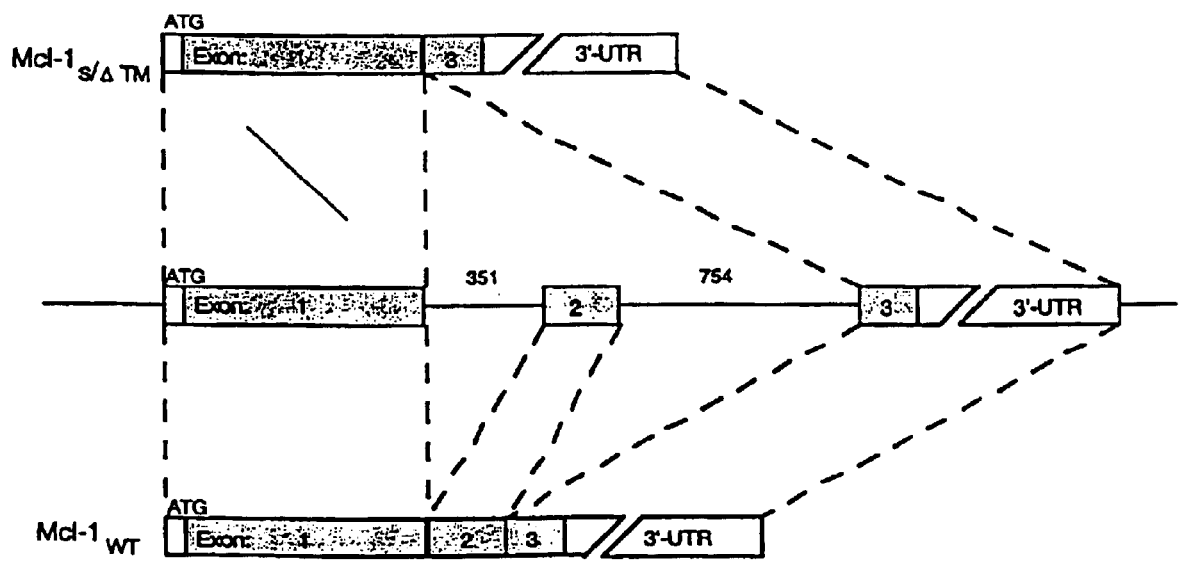

The Mcl-1s/ΔTM variant represents exon 1 joined to exon 3, with skipping of exon 2 (FIG. 5B). Exons 2 and 3 are not in the same phase, thus accounting for the shift in reading frame at the C-terminus of Mcl-1s/ΔTM as compared to Mcl-1. The other anti-apoptotic family members do not contain an intron comparable to Mcl-1 intron 1. However, an intron is present at this location in the gene encoding the pro-apoptotic Bax polypeptide (Bax intron 3; Oltvai et al., supra, 1993).

3. Mcl-1 transcription initiation sites lie directly upstream of the first coding exon Both Bcl-2 and Bcl-x contain upstream untranslated exons in addition to the two coding exons (see, for example, Grillot et al., supra, 1997). The presence of corresponding upstream exons and the transcription stat site of Mcl-1 was examined by primer extension analysis and S1 nuclease mapping. By primer extension, the most abundant of the products extended to about 70 bp upstream of the Mcl-1 translation start site (see FIG. 3B), and an additional product extended 10 bp further upstream. These results indicated that transcription initiated in the region of two tandem initiator sequences (see Example I; see, also, Liston and Johnson, *Mol. Cell. Biol.* 19:2380–2388 (1999)) present at this location in the immediate 5'-flanking sequence of the Mcl-1 gene.

The primer extension analysis did not specify initiation exclusively at a single nucleotide within the region of the Mcl-1 containing the tandem initiator sequences, but, instead, indicated that the Mcl-1 gene contains two initiator sequences, such that translation is initiated within an approximately 10 bp sequence of the Mcl-1 gene. S1 nuclease mapping also yielded a protected fragment indicative of transcriptional initiation in the region of the initiator sequences. The longest fragment obtained upon S1 nuclease mapping corresponded most closely to the more downstream of the sites identified by primer extension. Additional shorter fragments also were present, but can be a result of incomplete protection from S1 nuclease digestion. The failure to detected the more upstream site by S1 nuclease mapping may be related to the fact that it was associated with less abundant primer extension products. It could also relate to the presence of a repeated CACTTC sequence in the tandem initiators that may allow the formation of a loop upon binding to the probe. Nevertheless, both mapping methods indicated that a majority of Mcl-1 transcripts initiated from the more downstream of the two initiator sequences. Accordingly, this location was designated as position +1 (see FIG. 3B).

FIG. 3B shows the position of the initiator sequences relative to other features of the immediate 5'-flanking sequence of the Mcl-1 gene. Upstream from the initiator sequences lie the Ets and SRF binding elements involved in transcriptional regulation of the human Mcl-1 gene (see Example I). Elements similar to these transcription factor binding sites, as well as a potential initiator sequence, also are present in the 5'-flanking sequence of the mouse Mcl-1 gene (Wang et al., supra, 1999; Chao et al., *Mol. Cell. Biol.* 18:4883–4898 (1998), although the mouse Mcl-1 sequence only demonstrates about 56% sequence identity with the 5'-flanking region of human Mcl-1. These conserved elements may function similarly in the two species, as mutations affecting this region also affect transcription from the mouse Mcl-1 promoter (Wang et al., supra, 1999). Further upstream, the human Mcl-1 gene also contains a GGCCCC repeat region within a G/C-rich region (see FIG. 5A). Thus, the initiator sequences that mark the sites of Mcl-1 transcription lie in a region located between an upstream G/C-rich region and the downstream G/C-rich first coding exon.

The primer extension assay also revealed a very faint product extended approximately 25 nucleotides upstream of the other 2 sites, to about 155 bp from the #105C primer. This product indicates that transcription can also initiate further upstream, and is consistent with the observation that several EST clones present in the databases extend to near the two initiator sequences (see, for example, GenBank Accession Nos. AI1204385, AI1202072, AA776756, and AI1340205), while other EST clones contain additional upstream sequence (see, for example, GenBank Accession Nos. AI439001, AA884201, and AA453505). However, in the latter three clones, the upstream sequence is colinear with Mcl-1 genomic DNA, rather than containing a large gap. Thus, while the upstream portion of Mcl-1 contains regions that can be candidate splice donor and acceptor sequences, an upstream untranslated exon has not been identified. These results indicate that human Mcl-1 is transcribed from a region of the Mcl-1 gene containing tandem initiator sequences that lies 69 to 82 bp directly upstream of the coding sequence.

4. Transfection with the Mcl-1s/ΔTM variant results in cell death

The results discussed above indicate that the internally deleted Mcl-1 variant displays features similar to pro-apoptotic family members Bid and Bad, which contain only the BH3 domain. Accordingly, the ability of Mcl-1s/ΔTM to induce apoptosis was examined in mammalian epithelial cells.

Transient transfection assays were performed in Hela cells by co-transfecting a pCR3.1-Mcl-1s/ΔTM construct with pCMV-βgal as a marker for transfected cells. In control cells transfected with the insertless vector (pCR3.1; negative control), the majority of cells expressing the βgal marker remained morphologically normal and viable. In cells transfected with a Bax expression vector (positive control), the majority of transfected cells underwent cell death, as expected. Cell death was prominent in HeLa cells transfected with pCR3.1-Mcl-1s/ΔTM, with the transfected cells rounding up, and undergoing cell shrinkage and blebbing. Parallel cultures transfected with full length Mcl-1 (pCR3.1-Mcl-1) did not exhibit these morphological changes, in agreement with previous experiments in which Mcl-1 promoted viability of cells exposed to apoptosis-inducing stimuli without producing untoward effects in cells not exposed to such stimuli (Zhou et al., supra, 1997). These results indicate that Mcl-1s/ΔTM causes cell death, with the dying cells exhibiting the typical morphologic features of apoptosis.

The effect of the Mcl-1s/ΔTM on cell death was quantitated by counting all blue staining cells and scoring them, in a double blind manner, as either having a "normal," viable morphology (flat, healthy cells) or an "abnormal" morphology characteristic of cells dying by apoptosis (dense, rounded, detaching cells). This analysis showed that expression of the Mcl-1s/ΔTM isoform was as effective as Bax in killing Hela cells. Similar results were obtained when these constructs were transfected into A549 airway epithelial cells, thus confirming that transient expression of the Mcl-1 variant promoted apoptotic cell death.

The effect of Mcl-1s/ΔTM on cell death also was assessed using expression constructs in which the Mcl-1 isoforms expressed from the vector pEGFP-C1 as GFP fusion proteins. This study was carried out using A549 cells, which, as discussed above, demonstrated a cell death response following transient transfection with pCR3.1-Mcl-1s/ΔTM. Cells expressing the full length Mcl-1-EGFP fusion protein, or EGFP alone, exhibited no change in morphology. In contrast, cells expressing the Mcl-1s/ΔTM-EGFP fusion construct exhibited the morphological features of apoptosis, including nuclear condensation and cytoplasmic blebbing. These results demonstrate that Mcl-1s/ΔTM isoform expression induced apoptosis in various cell types.

Although the invention has been described with reference to the above examples, it will be understood that modifications and variations are encompassed within the spirit and scope of the invention. Accordingly, the invention is limited only by the following claims.

What is claimed is:

1. A purified Mcl-1 gene regulatory element, comprising a sequence of at least about twenty contiguous nucleotides of a nucleotide sequence set forth as nucleotides 1495 to 1657 of SEQ ID NO: 1.

2. The Mcl-1 gene regulatory element of claim 1, comprising nucleotides 1513 to 1564 of SEQ ID NO: 1.

3. The Mcl-1 gene regulatory element of claim 1, comprising a nucleotide sequence selected from the group consisting of:

nucleotides 1495 to 1550 of SEQ ID NO: 1;

nucleotides 1495 to 1564 of SEQ ID NO: 1;

nucleotides 1495 to 1606 of SEQ ID NO: 1;

nucleotides 1513 to 1550 of SEQ ID NO: 1;

nucleotides 1513 to 1564 of SEQ ID NO: 1; and nucleotides 1513 to 1606 of SEQ ID NO: 1.

4. The Mcl-1 gene regulatory element of claim 1, comprising a nucleotide sequence selected from the group consisting of:

nucleotides 1550 to 1657 of SEQ ID NO: 1; and nucleotides 1606 to 1657 of SEQ ID NO: 1.

5. The Mcl-1 gene regulatory element of claim 1, comprising nucleotides 1495 to 1657 of SEQ ID NO: 1.

6. A vector, comprising the Mcl-1 gene regulatory element of claim 1.

7. The vector of claim 6, which is an expression vector.

8. The vector of claim 6, further comprising a heterologous nucleic acid molecule operatively linked to said Mcl-1 gene regulatory element.

9. An isolated host cell containing the vector of claim 6.

10. A purified nucleic acid molecule encoding an Mcl-1 polypeptide, the nucleic acid molecule comprising nucleotides 1727 to 3884 of SEQ ID NO: 1; or a nucleic acid molecule fully complementary thereto.

11. The nucleic acid molecule of claim 10, comprising nucleotides 1657 to 3884 of SEQ ID NO: 1.

12. The nucleic acid molecule of claim 10, comprising nucleotides 1495 to 3884 of SEQ ID NO: 1.

13. The nucleic acid molecule of claim 10, comprising nucleotides 1 to 8253 of SEQ ID NO: 1.

14. A purified polynucleotide encoding the Mcl-1s/ΔTM amino acid sequence as set forth in SEQ ID NO: 3; or a polynucleotide fully complementary thereto.

15. The polynucleotide of claim 14, comprising nucleotides 1727 to 2414 of SEQ ID NO: 1 operatively linked to nucleotides 3768 to 3884 of SEQ ID NO: 1.

16. A vector comprising the polynucleotide of claim 14.

17. The vector of claim 16, which is an expression vector.

18. An isolated host cell, which contains the vector of claim 16.

19. The polynucleotide of claim 14, which is a polyribonucleotide.

20. A purified oligonucleotide, comprising at least fifteen contiguous nucleotides that are complementary to and hybridize specifically to an Mcl-1s/ΔTM splice junction comprising a nucleotide sequence of SEQ ID NO: 1 selected from the group consisting of:

a nucleotide sequence comprising nucleotide position 2414 of SEQ ID NO: 1;

a nucleotide sequence comprising nucleotide position 2766 of SEQ ID NO: 1;

a nucleotide sequence comprising nucleotide position 3013 of SEQ ID NO: 1; and a nucleotide sequence comprising nucleotide position 3786 of SEQ ID NO: 1, wherein at least three nucleotides of said oligonucleotide hybridize to a nucleotide sequence of SEQ ID NO:1 that is 5' and contiguous to said nucleotide position, and wherein at least three nucleotides of said oligonucleotide hybridize to a nucleotide sequence of SEQ ID NO:1 that is 3' and contiguous to said nucleotide position;

or a polynucleotide fully complementary to said substantially pure oligonucleotide.

21. A substantially pure oligonucleotide, comprising at least fifteen contiguous nucleotides that are complementary to and hybridize specifically to an Mcl-1s/ΔTM splicing junction comprising a nucleotide sequence of SEQ ID NO: 1 comprising nucleotides 2412 to 2414 of SEQ ID NO.1 operatively linked and contiguous to nucleotides 3768 to 3770 of SEQ ID NO: 1; or a polynucleotide fully complementary to said substantially pure oligonucleotide.

* * * * *